(12) United States Patent
Hartley et al.

(10) Patent No.: US 11,318,315 B2
(45) Date of Patent: May 3, 2022

(54) DEVICES AND METHODS FOR POSITIONING EXTERNAL DEVICES IN RELATION TO IMPLANTED DEVICES

(71) Applicant: Nalu Medical, Inc., Carlsbad, CA (US)

(72) Inventors: Lee Fason Hartley, Carlsbad, CA (US); Christopher Linden, Vista, CA (US); Daniel M. Pivonka, Encinitas, CA (US); Ji-Jon Sit, Carlsbad, CA (US); Lakshmi Narayan Mishra, Carlsbad, CA (US); Logan Palmer, Santa Monica, CA (US); Brett Daniel Schleicher, San Francisco, CA (US); Mark David Londborg, Woodland Hills, CA (US); James Goodman, Shorewood, MN (US); James C. Makous, Encinitas, CA (US); Andre Castillo, Encinitas, CA (US)

(73) Assignee: NALU MEDICAL, INC., Carlsbad, CA (US)

( * ) Notice: Subject to any disclaimer, the term of this patent is extended or adjusted under 35 U.S.C. 154(b) by 397 days.

(21) Appl. No.: 16/111,868

(22) Filed: Aug. 24, 2018

(65) Prior Publication Data
US 2019/0009097 A1    Jan. 10, 2019

Related U.S. Application Data

(63) Continuation of application No. PCT/US2017/023400, filed on Mar. 21, 2017.
(Continued)

(51) Int. Cl.
*A61N 1/372* (2006.01)
*A61N 1/378* (2006.01)
(Continued)

(52) U.S. Cl.
CPC ........ *A61N 1/37229* (2013.01); *A61N 1/025* (2013.01); *A61N 1/3787* (2013.01);
(Continued)

(58) Field of Classification Search
CPC combination set(s) only.
See application file for complete search history.

(56) References Cited

U.S. PATENT DOCUMENTS 5,201,312 A * 4/1993 Schenck ................ A61B 3/125
324/318
6,058,331 A * 5/2000 King .................... A61N 1/3605
607/2
(Continued)

FOREIGN PATENT DOCUMENTS

WO    WO-2014071079 A1    5/2014
WO    WO-2014205129 A1    12/2014
(Continued)

OTHER PUBLICATIONS

PCT/US2017/023400 International Search Report dated May 23, 2017.
(Continued)

*Primary Examiner* — Shirley X Jian
(74) *Attorney, Agent, or Firm* — Wilson Sonsini Goodrich & Rosati

(57) ABSTRACT

A stimulation system for a patient is provided. The system comprises: at least one implantable device comprising at least one implantable antenna; and an external device comprising at least one external antenna, wherein the at least one external antenna transfers power to the at least one implantable antenna. The at least one implantable device delivers therapy to the patient. A patient attachment device or body covering positions the at least one external antenna relative to the patient.

24 Claims, 29 Drawing Sheets

Related U.S. Application Data

(60) Provisional application No. 62/311,297, filed on Mar. 21, 2016.

(51) Int. Cl.
  *H02J 50/00* (2016.01)
  *A61N 1/02* (2006.01)
  *A61N 1/36* (2006.01)

(52) U.S. Cl.
  CPC ..... *A61N 1/37247* (2013.01); *A61N 1/37258* (2013.01); *H02J 50/00* (2016.02); *A61N 1/36071* (2013.01); *A61N 1/36125* (2013.01); *A61N 1/37235* (2013.01)

(56) References Cited

U.S. PATENT DOCUMENTS

| | | | |
|---|---|---|---|
| 6,516,227 B1* | 2/2003 | Meadows | A61N 1/36071 607/46 |
| 7,346,391 B1* | 3/2008 | Osorio | A61B 5/0476 607/2 |
| 7,925,357 B2* | 4/2011 | Phillips | A61N 1/3787 607/61 |
| 7,991,479 B2 | 8/2011 | Phillips et al. | |
| 8,280,517 B2* | 10/2012 | Skelton | A61N 1/37264 607/48 |
| 8,388,555 B2* | 3/2013 | Panken | A61B 5/7282 600/587 |
| 8,401,666 B2* | 3/2013 | Skelton | A61B 5/1116 607/62 |
| 8,504,138 B1 | 8/2013 | Pivonka et al. | |
| 8,504,150 B2* | 8/2013 | Skelton | A61B 5/103 607/17 |
| 8,579,834 B2* | 11/2013 | Davis | A61N 1/37247 600/595 |
| 8,612,015 B2* | 12/2013 | Knifong, Sr. | A61N 1/3787 607/61 |
| 8,626,297 B2* | 1/2014 | Jaax | H02J 7/007192 607/33 |
| 8,634,928 B1* | 1/2014 | O'Driscoll | A61N 1/3787 607/61 |
| 8,758,274 B2* | 6/2014 | Sahasrabudhe | A61B 5/7264 600/595 |
| 8,834,392 B2* | 9/2014 | Panken | A61B 5/369 600/595 |
| 9,149,210 B2* | 10/2015 | Sahasrabudhe | G16H 40/67 |
| 9,173,811 B2 | 11/2015 | Greiner et al. | |
| 9,272,081 B2* | 3/2016 | Cameron | A61M 1/127 |
| 9,433,750 B2 | 9/2016 | Pivonka et al. | |
| 9,440,084 B2* | 9/2016 | Davis | G16H 20/10 |
| 9,463,318 B2 | 10/2016 | Mashiach et al. | |
| 9,622,700 B2* | 4/2017 | Sahasrabudhe | G16H 40/67 |
| 9,919,159 B2* | 3/2018 | Skelton | G16H 40/63 |
| 10,207,118 B2* | 2/2019 | Skelton | G16H 20/30 |
| 10,238,872 B2 | 3/2019 | Pivonka et al. | |
| 10,320,232 B2 | 6/2019 | Pivonka et al. | |
| 10,335,596 B2 | 7/2019 | Yakovlev et al. | |
| 10,411,760 B2 | 9/2019 | Yakovlev et al. | |
| 10,644,539 B2 | 5/2020 | Pivonka et al. | |
| 10,682,521 B2* | 6/2020 | Jiang | A61N 1/3787 |
| 10,967,183 B2 | 4/2021 | Yakovlev et al. | |
| 2005/0075696 A1* | 4/2005 | Forsberg | A61M 5/1723 607/61 |
| 2009/0082835 A1* | 3/2009 | Jaax | H02J 7/007192 607/61 |
| 2009/0224361 A1* | 9/2009 | Liu | H01L 23/66 257/531 |
| 2010/0010383 A1* | 1/2010 | Skelton | A61B 5/103 600/587 |
| 2010/0010392 A1* | 1/2010 | Skelton | G16H 40/67 600/595 |
| 2010/0076525 A1* | 3/2010 | Skelton | A61N 1/37264 607/63 |
| 2011/0172562 A1* | 7/2011 | Sahasrabudhe | A61B 5/7282 600/587 |
| 2011/0172743 A1* | 7/2011 | Davis | A61B 5/1118 607/62 |
| 2012/0012630 A1* | 1/2012 | Lui | A41F 9/002 224/660 |
| 2012/0179071 A1* | 7/2012 | Skelton | G16Z 99/00 600/595 |
| 2013/0215979 A1 | 8/2013 | Yakovlev et al. | |
| 2013/0331638 A1 | 12/2013 | Cameron et al. | |
| 2014/0025140 A1* | 1/2014 | Lui | A61N 1/3787 607/61 |
| 2014/0180365 A1* | 6/2014 | Perryman | H01Q 1/273 607/60 |
| 2015/0335285 A1 | 11/2015 | Poon et al. | |
| 2016/0036261 A1* | 2/2016 | Lenive | H02J 7/025 320/108 |
| 2016/0331956 A1 | 11/2016 | Yakovlev et al. | |
| 2017/0095667 A1* | 4/2017 | Yakovlev | A61N 2/006 |
| 2018/0028824 A1 | 2/2018 | Pivonka et al. | |
| 2018/0256906 A1 | 9/2018 | Pivonka et al. | |
| 2018/0368875 A1 | 12/2018 | Castillo et al. | |
| 2019/0001139 A1* | 1/2019 | Mishra | A61N 1/37205 |
| 2019/0009097 A1* | 1/2019 | Hartley | H02J 50/12 |
| 2019/0151659 A1 | 5/2019 | Mishra et al. | |
| 2019/0269913 A1 | 9/2019 | Pivonka et al. | |
| 2019/0374776 A1 | 12/2019 | Mishra et al. | |
| 2020/0139138 A1 | 5/2020 | Sit et al. | |
| 2020/0204209 A1 | 6/2020 | Yakovlev et al. | |
| 2020/0222000 A1 | 7/2020 | Poon et al. | |
| 2020/0306528 A1 | 10/2020 | Linden et al. | |
| 2020/0398058 A1 | 12/2020 | Pivonka et al. | |
| 2021/0099015 A1 | 4/2021 | Pivonka et al. | |
| 2021/0196957 A1 | 7/2021 | Yakolev et al. | |

FOREIGN PATENT DOCUMENTS

| | | |
|---|---|---|
| WO | WO-2015139053 A1 | 9/2015 |
| WO | WO-2015196164 A3 | 2/2016 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |
| WO | WO-2021003439 | 1/2021 |
| WO | WO-2021067873 | 4/2021 |
| WO | WO-2021/133947 | 7/2021 |

OTHER PUBLICATIONS

EP17770982.1 Extended European Search Report dated Sep. 26, 2019.

* cited by examiner

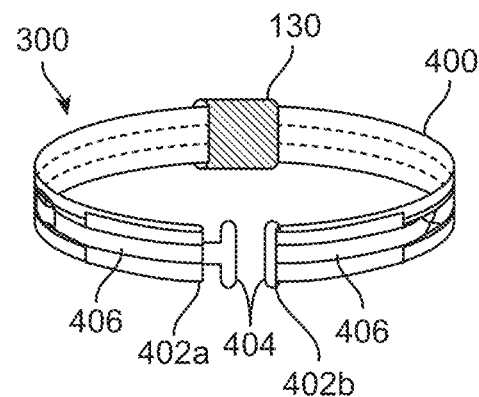
FIG. 11A
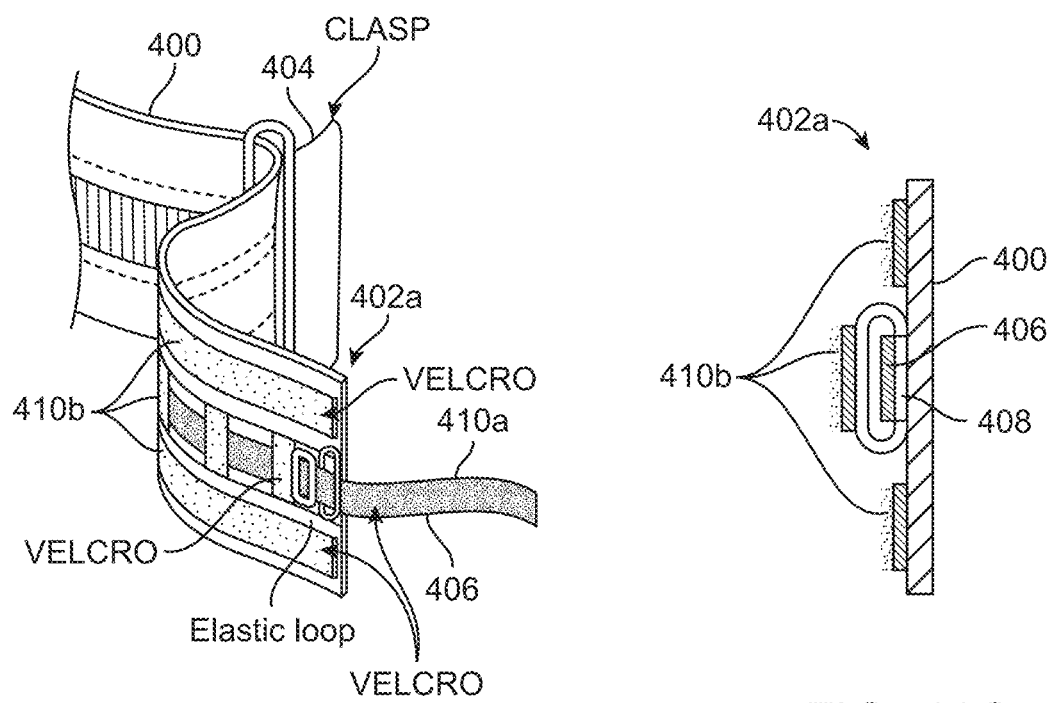
FIG. 11B
FIG. 11C

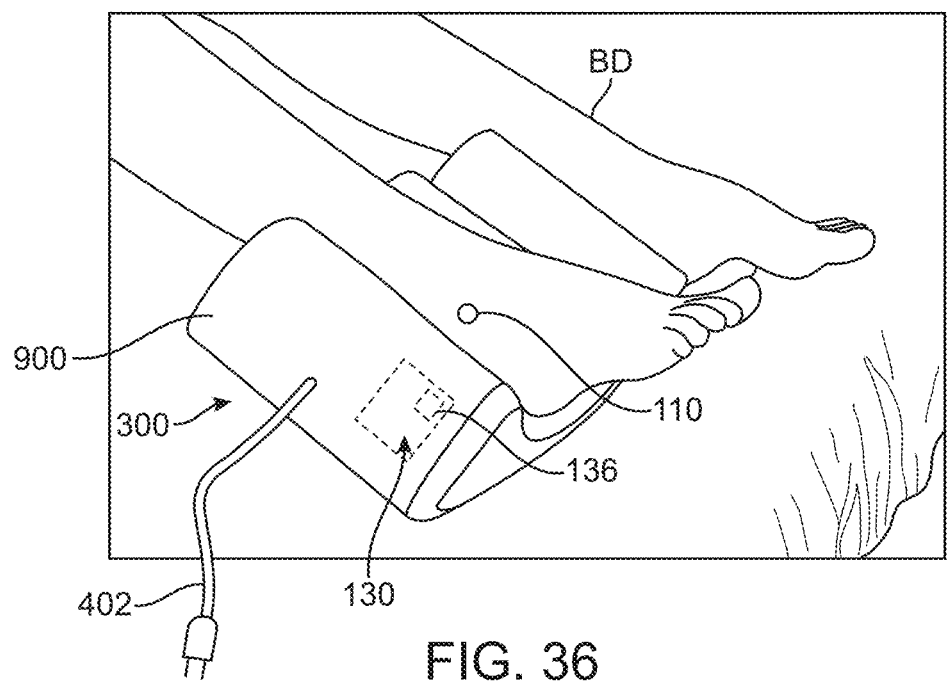
FIG. 36
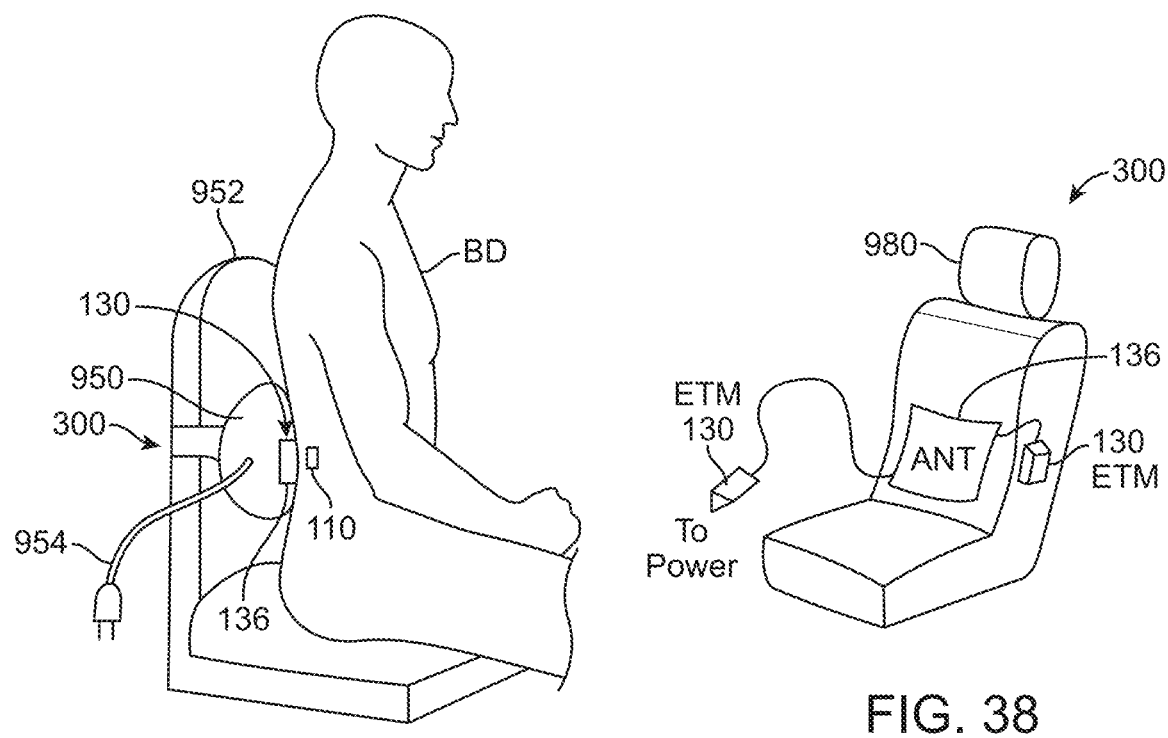
FIG. 37
FIG. 38

DEVICES AND METHODS FOR POSITIONING EXTERNAL DEVICES IN RELATION TO IMPLANTED DEVICES

CROSS REFERENCE

This application is a continuation of PCT Application No. PCT/US2017/023400, filed Mar. 21, 2017, which claims priority to U.S. Provisional Application No. 62/311,297, filed Mar. 21, 2016, the content of which is incorporated herein by reference in its entirety for all purposes.

SUMMARY OF THE INVENTION

The present inventions relate to neuromodulation methods, systems, devices and accessories for the treatment of acute and chronic pain conditions and pelvic disorders as well as other conditions or disorders. Chronic pain may include but is not limited to lower back and leg pain, migraine headaches, neuropathic pain, pain associated with herniated discs, muscle spasm or pinched nerve anywhere in the body, foot pain such as plantar fasciitis, plantar fibroma, neuromas, neuritis, bursitis, and ingrown toenails. Also addressed may be pain associated with malignant tumors. Acute pain may include but is not limited to postsurgical pain such as pain associated with thoracotomy or inguinal hernia repair, pain associated with procedures where an epidural block is used. This may be particularly and uniquely applicable in pregnancy to preliminarily disable the sensory nerves without the use of drugs and prior to delivery to avoid the potential for missing the window of time where an epidural can be administered. Pelvic disorders may include fecal incontinence; overactive bladder; urinary incontinence pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of the these.

Such neuromodulation involves precise, controlled modulation of specific nerves or tissues to induce physiological effects for therapies. In some instances, modulation is accomplished with a minimally invasive neuromodulation system that can target specific nerves with configurable modulation parameters and/or sensors for diagnostics or adaptations to the therapy. The neuromodulation system includes at least one implanted device, that serves as one or more modulators, and at least one external device that communicates or interfaces with the implanted device(s). The one or more modulators provides modulating energy that directly or indirectly effects the composition or behavior of the targeted nerve or tissue. Specific parameters of the modulating energy may be chosen for different treatment modalities. The one or more modulators are positioned in, on, around, or in the proximity of nerves or tissues to be influenced and are typically delivered in a minimally invasive manner through an introducer with anatomical guidance. The one or more modulators may be directly or indirectly attached to the nerves through a variety of methods based on the specific type of nerve or tissue as well as the intended therapy. Close proximity to nerves can reduce energy requirements and can eliminate unwanted stimulation of surrounding nerve tissue. The one or more modulators may be placed at a multitude of locations and configured with multiple parameters to increase the configurability of the treatment. For example, high frequency stimulation can block signals, while low frequency stimulation can mask symptoms. Multiple nerves can be stimulated in coordination, which may be provided with multiple modulators or interfaces. Real-time information, which may be provided by sensors in the devices or apparatuses, can further enhance the efficacy of therapy and may be applied for guided placement of an interface.

As mentioned, the at least one external device is disposed outside of the patient body and is positioned in communication range with the implanted device. Appropriate positioning of the external device is critical for optimal communication. Typically, the external device is disposed near the skin, such as against or on the skin or within a close distance. To assist in such positioning, the external device may be mounted on and/or embedded in an attachment assembly or body covering (also referred to as "positioning device" herein). The body covering covers a portion of the body, either against a surface of the body (such as adhered to the skin or held against the skin by fastening around a portion of the body), or at a distance from the surface of the body (such as separated by clothing, padding, comfort layers, additional devices or air gaps). Various embodiments of the body covering 300 will be described in detail herein.

The body coverings, accessories and other devices and methods of use described herein may be used with a variety of neuromodulation systems that include at least one implanted device that serves as one or more modulators and at least one external device that interfaces with the implanted device(s). In addition to those described herein, other compatible neuromodulation systems are further described in PCT/US2015/036821 entitled "METHOD AND APPARATUS FOR NEUROMODULATION TREATMENTS OF PAIN AND OTHER CONDITIONS", PCT/US2015/020808 entitled "METHOD AND APPARATUS FOR VERSATILE MINIMALLY INVASIVE NEUROMODULATORS", PCT/US2016/016888 entitled "MEDICAL APPARATUS INCLUDING AN IMPLANTABLE SYSTEM AND AN EXTERNAL SYSTEM" and U.S. Provisional Patent Application No. 62/217,356 entitled "APPARATUS FOR PERIPHERAL OR SPINAL STIMULATION", each of which are incorporated herein by reference for all purposes.

According to a first aspect of the invention, a stimulation system for a patient comprises: at least one implantable device comprising at least one implantable antenna; and an external device comprising at least one external antenna, wherein the at least one external antenna transfers power to the at least one implantable antenna. The at least one implantable device delivers therapy to the patient.

In some embodiments, the system is defined by a Z-parameter matrix including cross terms, the at least one implantable antenna and the at least one external antenna each comprise an impedance, the cross terms represent coupling between the antennas, and the power transfer is optimized based on the antenna impedances and the cross terms.

In some embodiments, the system is defined by a Z-parameter matrix, variation of the matrix is due to lateral displacement, rotational displacement, and/or depth displacement between the external device and at least one implantable device.

In some embodiments, the at least one external antenna comprises a single-turn loop antenna with an impedance and the at least one implantable antenna comprises a single-turn loop antenna with an impedance, the system is defined by a Z-parameter matrix including values representing the antenna impedances and the coupling between the at least one external antenna and at least one implantable antenna, and the system is configured to maintain a high power transfer efficiency and maximized bandwidth by performing an optimization of the Z-parameter matrix.

In some embodiments, the at least one implantable device comprises a power harvesting circuit configured to de-sensitize the system to coupling.

In some embodiments, the at least one implantable antenna and/or the at least one external antenna is tuned based on an anticipated implantation depth of the at least one implantable antenna.

In some embodiments, the at least one external antenna and/or the at least one implantable antenna is configured to be adjustably tuned. The at least one external antenna can comprise a larger size than the at least one implantable antenna, and the external antenna can be configured to be adjustably tuned.

In some embodiments, the at least one external antenna comprises a quality factor configured to be adjusted. The external device can be further configured to transfer data to the at least one implantable device, and the external device can comprise a matching network configured to increase the bandwidth during periods of data transfer by reducing the quality factor. The external device can be configured to increase the quality factor during periods of power transfer without data transfer.

In some embodiments, the at least one implantable antenna and/or the at least one external antenna comprises a backing comprising magnetic material. The backing can be configured to minimize sensitivity of the at least one implantable antenna and/or the at least one external antenna to metallic objects proximate the backing. The at least one external antenna can comprise the backing, and the backing can be configured to radiate magnetic energy preferentially toward the implanted device. The at least one implantable antenna and/or the at least one external antenna can further comprise a lossy material and/or a ground plane configured to absorb RF radiation.

In some embodiments, the at least one implantable device further comprises a power harvesting circuit comprising variable loading and configured to recover low voltage signals.

In some embodiments, the at least one external antenna comprises a single loop antenna with a first size, the at least one implantable antenna comprises a single loop antenna with a second size, and the first size is greater than the second size.

In some embodiments, the at least one external antenna comprises a major axis with a length between 2 cm and 10 cm, and the at least one implantable antenna comprises a major axis with a length less than 2 cm. The at least one external antenna can comprise a major axis with a length between 4 cm and 7 cm, and wherein the at least one implantable antenna comprises a major axis with a length less than 1.2 cm.

In some embodiments, the at least one external antenna transmits signals with a frequency between 1 MHz and 1 GHz. The at least one external antenna can transmit signals with a frequency between 30 MHz and 300 MHz. The at least one external antenna can transmit signals with a frequency between 40.66 MHz and 40.7 MHz. The at least one external antenna can transmit signals with a frequency of approximately 40.68 MHz.

In some embodiments, the at least one external antenna and/or at least one internal antenna comprises an array of antennas with different drive configurations and configured to: reduce positional sensitivity; improve efficiency; decrease SAR; and/or decrease emissions.

In some embodiments, the at least one external antenna comprises an array of antennas, and the external device is configured to precisely control the magnitude and/or phase of signals provided to each antenna of the array.

In some embodiments, the external device comprises one or more transmitters, the at least one external antenna comprises a switch array comprising multiple antennas and configured to multiplex the one or more transmitters and the multiple antennas. The external device can be configured to perform a function selected from the group consisting of: time multiplexing of RF power to two or more of the multiple antennas; ratiometric multiplexing of RF power to two or more of the multiple antennas; and/or provide phase delay to one or more of the multiple antennas.

In some embodiments, the at least one external antenna comprises an antenna array, a Z-parameter and/or S-parameter matrix describes coupling parameters of the antenna array and the at least one implanted device in a desired operating environment, and the system is configured to optimize amplitude, phase, and/or other transmission parameters based on the coupling parameters. The system can be configured to perform the optimization using: a multi-dimensional gradient search technique; measurements; a lookup table; calculations; algorithms; and/or weighted averages. The system can be configured to perform the optimization using a scan and/or measurement that provides location and/or coupling characteristic information of the at least one implantable device. Entries of a Z-parameter and/or an impedance matrix can be updated based on the scan and/or measurement.

In some embodiments, the at least one external antenna comprises multiple external antennas that communicate with the at least one implantable antenna, and the multiple external antennas are constructed and arranged based on the at least one implantable antenna.

In some embodiments, the at least one implantable device is configured to transmit data to the external device. The at least one implantable device can be configured to transmit data to the external device via: load modulation; backscattering; and/or skin contact. The data transmissions can be performed at a rate of between 0.25 Mbps to 4 Mbps. The data transmissions received by the external device can be used to determine coupling, measure and/or sense an at least one implantable device parameter, and/or monitor therapy status.

In some embodiments, the at least one external antenna further transfers data to the at least one implantable antenna, and the power and data are transferred in combination and/or asynchronously.

In some embodiments, the external device comprises a first external device, the system further comprises at least a second external device comprising at least one external antenna, and the multiple external devices are configured to make a patient-position based therapy adjustment and/or a situation-based therapy adjustment.

In some embodiments, the system further comprises cloud storage configured to store and/or analyze patient payment information.

In some embodiments, the system further comprises a sensor configured to produce a signal related to patient location and/or position, and the system is configured to make a therapy adjustment based on the signal. The sensor can comprise a sensor selected from the group consisting of: accelerometer; GPS sensor; Bluetooth low energy sensor; and combinations thereof.

In some embodiments, the system is configured to make a therapy adjustment based on an impedance measurement and/or measurement of a physiologic parameter.

In some embodiments, the system comprises an electromechanical connector configured to produce a signal, and the system is configured to activate and/or deactivate therapy based on the signal.

In some embodiments, the system comprises a skin contacting sensor configured to produce a signal, and the system is configured to activate and/or deactivate therapy based on the signal.

In some embodiments, the system further comprises a positioning device configured to desirably position the at least one external antenna in relation to the patient, the positioning device further configured to allow adjustment of the position of the at least one external antenna. The positioning device can comprise an adjustable harness. The positioning device can comprise a rack and pinion mechanism. The positioning device can comprise a flexible, sliding straps mechanism. The positioning device can comprise a lateral adjustment strap and a vertical adjustment strap. The positioning device can comprise a hook and loop attachment mechanism. The external device can comprise multiple discrete components, and the positioning device can position the multiple discrete components. The positioning device can comprise a clip with an adhesive portion. The positioning device can comprise a clip comprising a housing defining a cavity, and the cavity can be constructed and arranged to slidingly receive the external device. The external device can comprise at least one control, the positioning device can comprise a clip comprising a housing including an opening, and the opening can be constructed and arranged to provide access to the at least one control.

In some embodiments, the at least one external antenna comprises multiple antennas, and the external device comprises a transmitter operatively connected to the multiple antennas.

In some embodiments, the at least one external antenna and/or the at least one implantable antenna comprises an array of antennas configured to reduce sensitivity to alignment and/or rotation between the at least one external antenna and the at least one implantable antenna.

In some embodiments, the system further comprises a feedback element configured to notify the patient that repositioning of the at least one external antenna is desired. The feedback element can comprise an element selected from the group consisting of: a visual feedback element; an LED; an acoustic feedback element; a buzzer; a tactile feedback element; a haptic transducer; modified stimulation; paresthesia-causing stimulation; and combinations thereof.

In some embodiments, the system further comprises a positioning device configured to desirably position the at least one external antenna in relation to the patient, and the positioning device is configured to temporarily or permanently position the at least one external antenna. The positioning device can comprise at least one of an adhesive or a clip.

In some embodiments, the system further comprises a positioning device configured to desirably position the at least one external antenna in relation to the patient, and the positioning device comprises a tab configured to adhesively attach to the skin of the patient.

In some embodiments, the system further comprises a positioning device configured to desirably position the at least one external antenna in relation to the patient, and the positioning device provides a pressure-applying force between the at least one external device and the patient. The positioning device can position the at least one external antenna proximate an implant incision site. The positioning device can comprise a sterile bandage.

In some embodiments, the system further comprises a positioning device configured to desirably position the at least one external antenna in relation to the patient, and the positioning device comprises a raised edge for guiding placement of the at least one external antenna.

In some embodiments, the system further comprises a positioning device configured to desirably position the at least one external antenna in relation to the patient, and the positioning device comprises a raised disc over which an antenna is placed.

In some embodiments, the system further comprises a positioning device configured to desirably position the at least one external antenna in relation to the patient, and the positioning device comprises a transcutaneous anchor. The anchor can comprise biodegradable suture.

In some embodiments, the system further comprises a positioning device configured to desirably position the at least one external antenna in relation to the patient, and the positioning device comprises at least an implantable portion. The positioning device can comprise an implantable portion comprising a first magnet and an external portion comprising a tether retention device including a second magnet. The first magnet can be positioned in the at least one implantable device. The first magnet can be configured to absorb RF radiation of the at least one implantable device.

In some embodiments, the at least one implantable device comprises a locating element. The locating element can comprise an element selected from the group consisting of: ring-shaped element; a cavity; a dome; and combinations thereof.

In some embodiments, a component of the system is affixed to the patient at a first skin location for a first time period, and at a second skin location for a second time period. The system can further comprise an adhesive coupling mechanism comprising multiple adhesive elements configured to be serially exposed adhesive elements. The adhesive coupling mechanism can further comprise an orientation marker. The adhesive coupling mechanism can comprise a tear-away adhesive strip configured to be deployed after proper positioning of the external device. The adhesive coupling mechanism can comprise a body marking applied to the skin of the patient and configured to indicate the location of the at least one implantable device and/or the location on the skin at which the external device should be aligned.

In some embodiments, the system further comprises an external sensor and/or mechanism configured to determine the implantable device implant location. The external sensor and/or mechanism can comprise an electrical, magnetic and/or mechanical sensor. The external sensor and/or mechanism can be configured to determine the implantable device implant location using power transfer parameters and/or coupling coefficients. The external sensor and/or mechanism can be configured to determine the implantable device implant location using: received power; RF signal strength; and/or supply voltage measurements made by the implanted system and communicated to the external system, through a data back channel. The external sensor and/or mechanism can be configured to determine the implantable device implant location using: parameters sensed by the external system by detecting changes in loading that indicate received power of the internal system, mutual inductances, and/or backscattered electromagnetic fields.

In some embodiments, the system further comprises an absorbent material configured to displace and/or reduce sweat of the patient. The absorbent material can comprise washable, reconditionable, and/or multi-use absorbent material.

In some embodiments, the system further comprises a positioning device configured to desirably position the at least one external antenna in relation to the patient, the positioning device comprising a pillow, a cushion, a pad, a foot rest, and/or a lumbar support device.

In some embodiments, the system further comprises a positioning device configured to desirably position the at least one external antenna in relation to the patient, and the positioning device comprises a chair configured to surround the at least one external antenna.

In some embodiments, the system further comprises an applicator and a positioning device configured to desirably position the at least one external antenna in relation to the patient, and the applicator is configured to assist in positioning the positioning device on the patient. The applicator can be configured to be positioned on a chair.

In some embodiments, the system further comprises a battery socket constructed and arranged to receive multiple different battery types.

In some embodiments, the external device comprises a permanent rechargeable battery configured to be charged via wired or wireless energy transfer.

In some embodiments, the external device comprises at least two batteries, and the external device is configured to operate properly using energy from a single battery.

In some embodiments, the external device comprises a permanently integrated battery and a removable battery.

In some embodiments, the external device comprises a magnetic material and/or RF absorbent material that is configured to prevent the at last one external antenna from radiating into free space.

In some embodiments, the external device comprises a magnetic material and/or RF absorbent material that is configured to shield the at least one external antenna from being de-tuned.

Embodiments of the present invention are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which:

FIGS. 11A-11C illustrate another embodiment of a body covering having an external device whose position is finely adjustable in relation to the patient's body while the patient is wearing the body covering.

FIG. 36 illustrates an embodiment of a body covering accessory having the form of a pillow, cushion or pad.

FIG. 37 illustrates another embodiment of a body covering accessory having the form of a pillow, cushion or pad.

FIG. 38 illustrates an embodiment of a body covering accessory having the form of a therapeutic chair.

DETAILED DESCRIPTION OF THE INVENTION

Specific embodiments of the neuromodulation methods, systems, and devices for the treatment of acute and chronic pain conditions, as well as other conditions or disorders, will now be described with reference to the drawings. Nothing in this detailed description is intended to imply that any particular component, feature, or step is essential to the invention.

Figure 1:
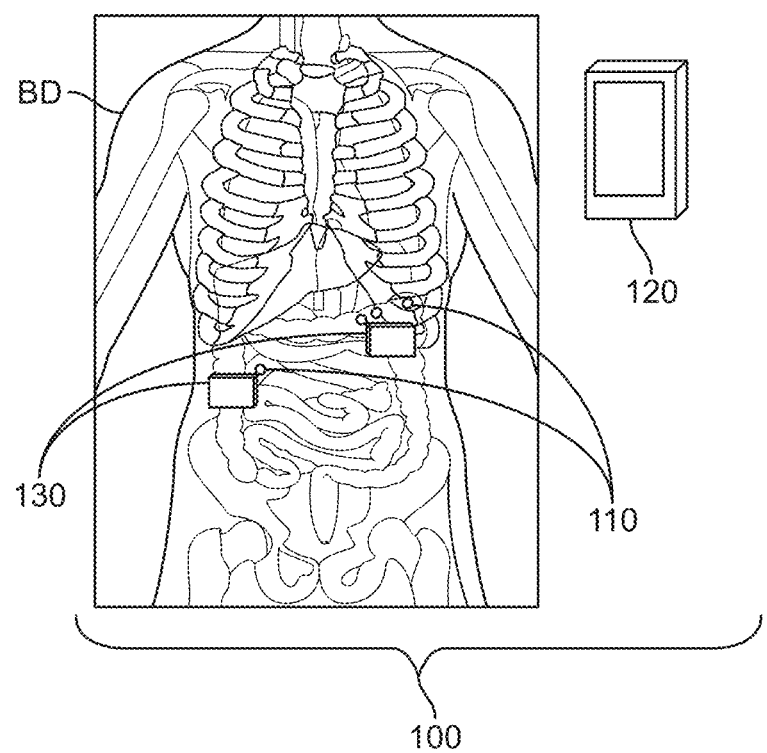
FIG. 1 schematically illustrates example external devices positioned outside the body, wherein each external device interfaces with one or more implanted devices or modulators.

Neuromodulation is achieved with the use of at least one external device that interfaces with one or more implanted modulators. The at least one external device provides power and optionally controls the operation of the implanted modulator and/or gathers information regarding the implanted modulator and/or the patient. One or more of the external devices can also provide an interface for a patient or a clinician to control the therapy and monitor its effectiveness. FIG. 1 schematically illustrates example external devices 130 positioned outside the body BD, wherein each external device 130 interfaces with one or more implantable devices 110 or modulators. In some instances, the elements of the overall system 100 can allow for miniaturized implanted devices 110 in the cm, mm and sub-mm size range. This miniaturization can be accomplished in part by the ability of the overall system 100 to utilize a variety of different antennas and an on-board intelligent power management system. The external device 130 may include components for power transfer, power storage (e.g. battery), battery management, data transfer, programmability, data management (including processing and visualization) and a user interface for clinicians and/or patients. The user interface could consist of button(s), a touchscreen display, knob(s), keyboard, keypad, display, microphone, light, speaker and/or other component configured for user input and/or user output. Optionally, some of these components can be disposed in a handheld interface 120, such as a programmer.

Figure 2:
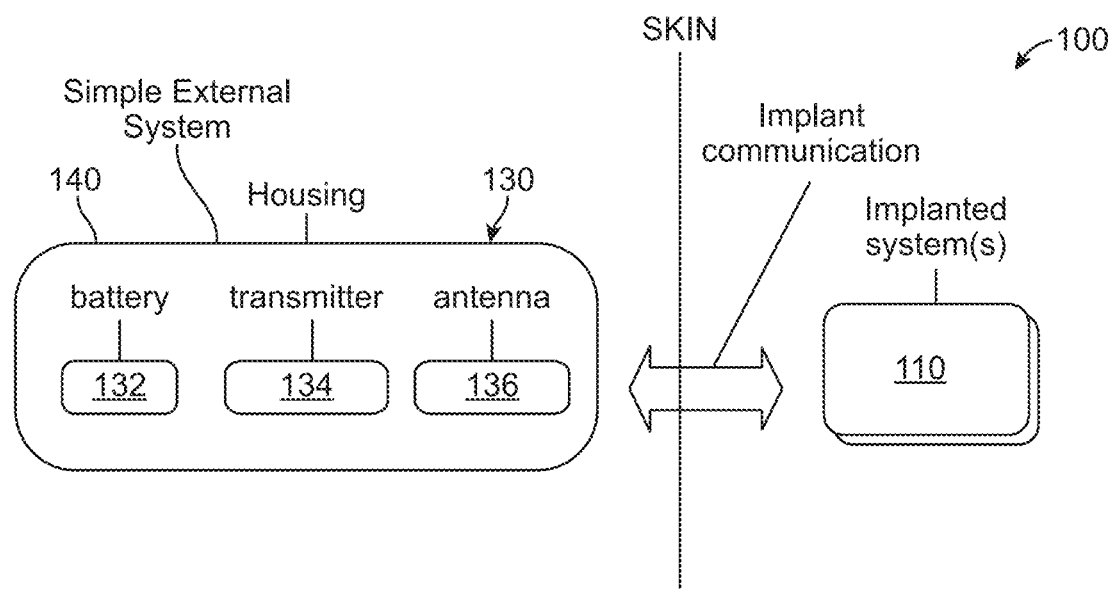
FIG. 2 schematically illustrates an example system comprising an implanted device and a simple external device.

FIG. 2 schematically illustrates an example system 100 comprising an implantable device 110 and a simple external device 130. Here, the external device 130 comprises a battery 132, a transmitter 134 and an antenna 136 for the purpose of exciting an implantable device 110 that has permanently established functional parameters (e.g. stimulation amplitudes, rates, duty cycles, contacts, etc.). Such an external device 130 may be disposable or single use or rechargeable. Such single use or disposable embodiments may contain primary cell batteries (e.g. alkaline, lithium, Zn-Air) and rechargeable embodiments may contain rechargeable batteries (NiMH, lithium-ion, lithium-polymer) or chargeable/precharged supercaps. Rechargeable batteries may be removable or permanently integrated. In certain embodiments, such simple external devices may be targeted to be single use, short term use or long term reusable. Since such devices are free of advanced complexity, they can be smaller in size and very robust. In some embodiments, the external device 130 includes a housing 140 which may be hermetically or non-hermetically sealed. In some instances, the housing 140 is waterproof or water resistant, such as to facilitate use by patients during activities such as swimming or working in unusually dirty areas or during particularly strenuous activities (e.g. playing sports).

Figure 3:
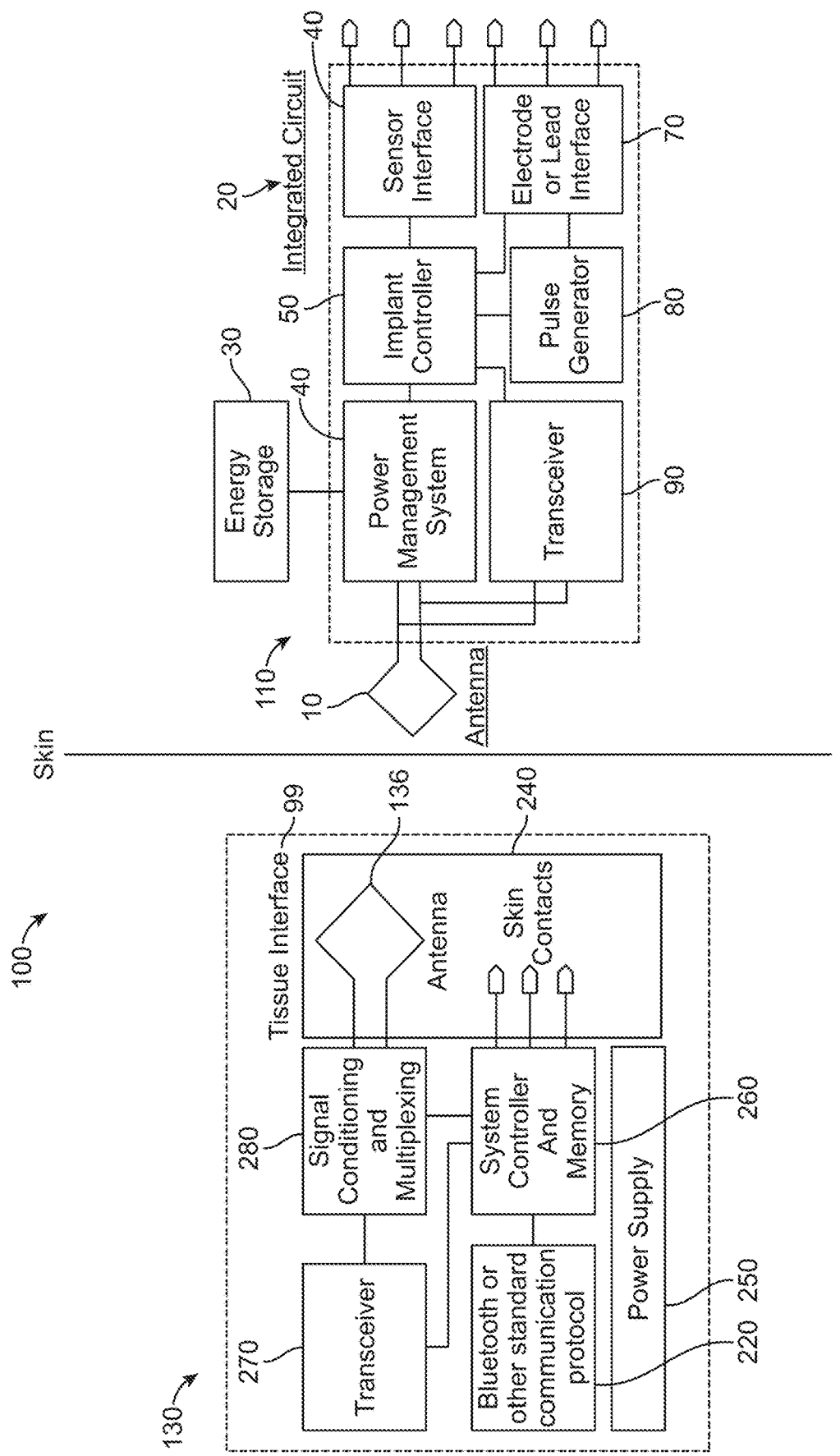
FIG. 3 schematically illustrates an example system comprising an implanted device and a more complex external device.

FIG. 3 schematically illustrates an example system 100 comprising an implantable device 110 and a more complex external device 130. In this embodiment, the external device 130 includes at least one transmission antenna 136 that is placed near the surface of the skin in close proximity to the antenna 10 of the implantable device 110. The tissue interface 99 may include impedance matching materials that may contain gels or other electrically active interface materials. This link can transfer both power and data to the implantable device 110. In this embodiment, the implantable device 110 further comprises an integrated circuit 20 and an energy storage unit 30 (such as a battery) coupled to the integrated circuit 20. In this embodiment, the integrated circuit 20 comprises a power management subsystem 40 coupled to the energy storage unit 30, an implant controller 50 coupled to the power management sub-system 40, a sensor interface 60 coupled to the implant controller 50, an electrode or lead interface 70, a pulse generator 80 coupled to the implant controller 50 and the electrode or lead interface 70, and a transceiver 90 coupled to the at least one antenna 10, the power management sub-system 40, and the implant controller 50.

In this embodiment, the external device 130 includes a tissue interface 135 which comprises the antenna 136 and skin contacts 240. Here, the external device 130 further comprises a power supply 250, a system controller (which may include user accessible controls) and memory 260 which may be coupled to a Bluetooth or other standard communication protocol 220, a transceiver 270 coupled to the system controller and memory 260, and a signal conditioner and multiplexer 280 coupled to the transceiver 270 and the system controller and memory 260. Skin contacts 240 may be used to communicate with the implant, or to sense skin contact as an interlock to enable therapy, or to sense stimulation as an operational monitor or diagnostic.

As illustrated, the external device 130 includes a transmission antenna 136 that is placed near the surface of the skin in close proximity to the antenna 10 of the implantable device 110. As mentioned, this link can transfer both power and data to the implantable device 110. The external device 130 can also receive information from the implantable device 110 via several methods depending on the data protocols of the implantable device 110. This communication may include a load modulation sub-system in which antenna impedances are sensed, back-scattering modulation in which reflected electromagnetic waves are detected, or tissue conduction in which small electrical signals are transferred through the tissue itself to the skin contacts 240. The external device 130 can operate with either batteries or with external power. The external device 130 may also have a separate communication protocol 220, such as Bluetooth, for interfacing with computers, smart phones, or other devices. The external device 130 can include an information display with information about the device performance, information about the therapy, or controls for adapting parameters. Data can be transferred at speeds up to and exceeding 20 Mbps to accommodate configuration and control of the external device 130 as well as real-time treatment adjustments, such as in the range of 10 Hz-40 kHz, or 10 kbps-20 Mbps, or in the range of 0.25 Mbps-4 Mbps, or 0.5-4 Mbps. Data and power can also be transferred to multiple implantable devices 110 simultaneously and the high-speed of communication allows for several devices to adapt and adjust in real-time. Sensors can be incorporated with the external device 130 and also make use of the high-speed communication system for diagnostics or real-time feedback of physiological parameters to inform the clinician or patient of the functionality of the device or to provide feedback to the system to adapt the treatment. This information can be stored locally or transferred securely to other devices or to the cloud where it is accessible from the internet. Data processing and visualization can also be performed locally or on other devices.

The external device 130 can wirelessly power implantable devices 110 via either electromagnetic coupling or through a mechanical transfer, such as via an ultrasonic signal. Depending on the application, patient, frequency, number of implants, depth of implants, and other factors, the external device 130 can operate with a variety of antennas or transmitters of different sizes. The external device 130 can interface with one or more antennas via RF signal generation and conditioning circuits and matching network which can accommodate a variety of such antennas and operating frequencies. Moreover, the external device 130 can adjust how much power is transferred to one or more implantable devices 110 based on feedback from the implants and/or based on externally sensed quantities, such as tissue and system temperature.

For wireless powering and communication using electromagnetic energy the external device 130 uses one or more antennas 136. The one or more antennas 136 can be implemented on a printed circuit board comprising one or more rigid and/or flexible substrates. Alternatively, textile substrates can be used to implement one or more such antennas. Also, multiple external antennas 136 can be used simultaneously or exclusively in order to provide better coupling between the implantable and external antennas 10, 136.

High-speed, efficient communication can be accomplished by combining data transfer into the power signal. This combination can be non-trivial, especially at high frequencies because most modulation methods can have a significant effect on power transfer and using a separate communication system would result in large interference. Asynchronous methods can dramatically reduce system requirements, and power transfer can remain uninterrupted by employing methods that minimally modulate the amplitude. These data transfer methods could also operate with multiple devices simultaneously by assigning each device a specific address or ID. The communication methods described can use encoding and encryption to improve reliability, safety, and security.

The external device 130 can rely on data from the implantable device 110 for multiple purposes. These purposes include improved positioning of the external device 130 to improve coupling between external and implant antennas 136, 10, monitoring of various sensed quantities by the implantable device 110, monitoring of implant status and therapy status. One or more of these sets of data can be used to re-adjust the therapy either in closed-loop or via user input. The reverse data link from the implantable device 110 to the external device 130 can be non-trivial and can be accomplished via a variety of methods. Some methods may rely on backscattering signal transmitted by the external device(s) to the implantable device(s) by modulating load on the implant antenna. Other methods may rely on implantable device 110 having a transmitter circuit which generates a carrier signal and transmits it to the external device 130. Other methods may include implantable device 110 relying on volume conduction to communicate with the external device by modulating voltage or current through electrodes connected to tissue. Depending on the selected communication scheme, the external device can be configured to receive and demodulate this signal from one or more implants.

The external device 130 may also keep track of the desired therapy program and actual applied therapy to the patient. The external device 130 can collect data from embedded sensors, patient input, and/or one or more implants, and store the data in embedded memory and/or upload it to external storage such as a phone or cloud storage system. The external device 130 can also issue one or more notifications to the patient, clinician, or even emergency dispatch personnel, based on this sensed and stored data.

Treatment parameters can be controlled remotely via the external device 130 and adapted based on performance or changes in the patient's condition. The external device 130 can be controlled by a clinician, the patient, or some combination of the two depending on the intended use. Therefore, the overall system 100 can accommodate a variety of interface with external infrastructure via existing protocols such as Bluetooth, ZigBee, WiFi, 2net platform interface, and other wireless and wired general or medical protocols and interfaces. These interfaces can rely on built-in encryption or privacy or can incorporate additional custom encryption and error detection and correction encoding.

Figure 4:
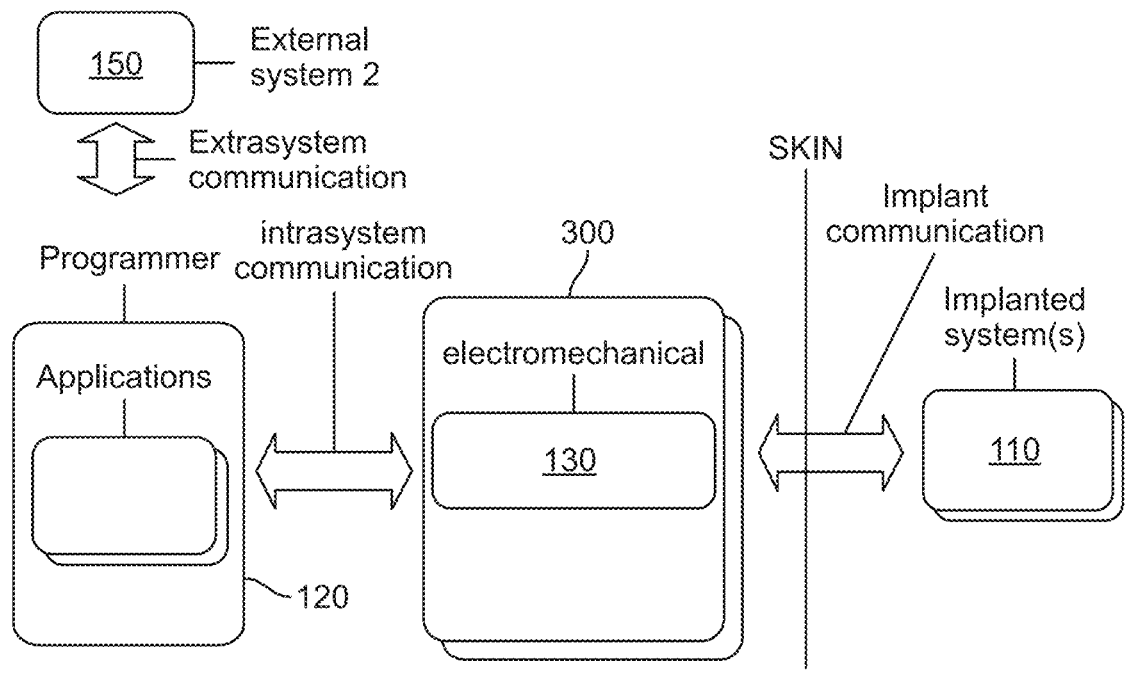
FIG. 4 schematically illustrates a system having an external device and a body covering along with additional external devices, including a handheld interface and a standalone device.

As mentioned, the external device 130 is disposed outside of the skin of the patient body BD and is positioned in communication range with the implanted device 110. Appropriate positioning of the external device 130 is critical for optimal communication. Typically, the external device 130 is disposed near the skin, such as against or on the skin or within a close distance. To assist in such positioning, the external device 130 may be mounted on and/or embedded in a positioning device, body covering 300, such as schematically illustrated in FIG. 4. Various embodiments of the body covering 300 will be described in detail herein.

In some embodiments, the system 100 further includes one or more additional external devices, such as a handheld interface 120 and a stand-alone device 150, as schematically illustrated in FIG. 4. Here, the implantable device 110 may be bi-directionally or uni-directionally interfaced with from one or more of the additional external devices 120, 130, 150 directly or by way of a relayed interface such as 150 to 120 to 130 to implantable device 110, or such as 150 to 130 to implantable device 110, or other combinations by extension. The external device 130 and the handheld interface 120 may interface with each other (intrasystem communication in FIG. 4). Furthermore, the stand-alone device 150 may interface with the handheld interface 120 and/or external device 130 (intersystem communication in FIG. 4), possibly interfacing to the same or different implantable devices 110. It may be appreciated, that the components of the external device 130 and the additional external devices 120, 150 may be arranged in a variety of combinations wherein one or more components described as part of any of these devices may be disposed on any other of the devices. For example, the components of the external device 130 and the handheld interface 120, such as those of the programmer, applications and transmitter system, may be assembled monolithically wherein the depicted intrasystem communication is implemented on a single integrated circuit, via connections on a discretely populated printed circuit board or between software application modules. Conversely, any external components may be comprised of discrete components or subassemblies arranged to meet the needs of different patients, applications or environments.

For any external system embodiment, communication with one or more implantable devices 110 may occur simultaneously or in a time division multiplexed manner or under a manually (e.g. patient) controlled manner. External systems, depending on their function, may not require all system components; for example, certain external systems may not communicate directly with an implantable device 110, rather they only do so via communication with an intermediary external system equipped with the necessary subsystem components (e.g. transmitter and antenna) to conduct implant communications. Multiple external systems may be deployed with a patient and can be able to interact with one another via extrasystem communication which may comprise the sharing of power, data and control via wired, wireless, solid state or cloud based means. In some embodiments, multiple external devices cooperatively interact such as to make a patient-position based therapy adjustment and/or a situation-based therapy adjustment as described herebelow. As an example, an external system positioned on a patient's ankle may communicate (e.g. cooperatively communicate) with an external system on a patient's abdomen and together determine that the patient is sitting, walking or lying down and take measures to adjust some aspect of system function accordingly. In another embodiment, an external system may interact (e.g. cooperatively interact) with a non-patient worn external system that is kept bedside or in a vehicle to notify the system of the surroundings and adjust some aspect of system function accordingly. In another embodiment, to restore therapy, an external system given to a patient to replace a previously lost external system may interact with another external system connected to a cloud storage media for the retrieval of the patient's preferences, habits and programs to replace the lost external system. Alternatively, the cloud storage may check (e.g. store and/or analyze) account status (e.g. payments, such as in a "pay-per-use" arrangement) or prescribed treatments (prescriptions), etc. so as to mediate the delivery of therapy to a patient under the direction of a service provider (selling stimulation tokens) or a physician (prescribing specific treatment paradigms). As such, an external system may be a fully functional standalone external system comprised of one or more independent elements, at least one of which can communicate with an implant, or it may simply be a commercially available piece of technology (i.e. a smartphone or a computer) with internet connection and requisite application support, a FLASH memory stick with stored application code or data, a simple configurable or preconfigured location beacon (e.g. RFID), or it may be a hybrid multi-component of elements similar in kind to those described herein. External systems, whether highly integrated or discretely assembled, that are custom designed to communicate with implantable devices 110 will implement all or some elements of programmer, application, electromechanical and appropriate positioning in order to ensure usability by the patient.

Figure 5:
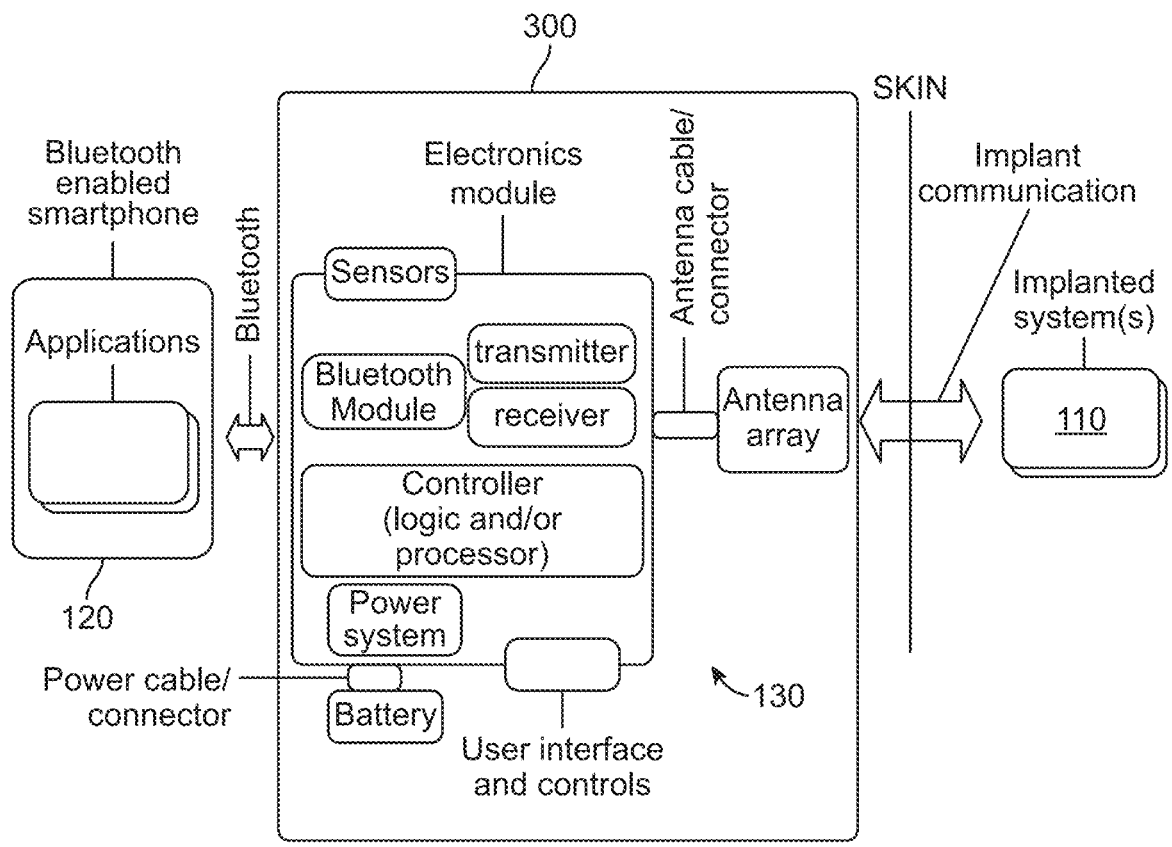
FIG. 5 schematically illustrates a system which includes a smartphone running a custom software application responsible for configuring a wirelessly connected external device incorporated in a body covering.

FIG. 5 schematically illustrates a system 100 which includes a smartphone or computer running a custom software application responsible for configuring (programming, changing settings, etc.) a wirelessly (e.g. WiFi, Bluetooth) connected external device 130 incorporated in a body covering 300. The external device 130 includes one or more interconnected electromechanical components (e.g. housings, connectors, cables, batteries, printed circuit boards, etc.) that are suitably arranged for communication with the patient implantable device 110 and held comfortably and reliably in place by a body covering 300 custom designed for the required anatomy.

It may be appreciated that connections between submodules may vary by embodiment. For example, for the connection between the antenna or antenna array and transmitter 134, also referred to as the external transmitter module (ETM), in different embodiments it may be advantageous to have connectors on one end (e.g. antenna only), the other end (e.g. ETM only), both ends or neither end (e.g. permanent connection). It may also be appreciated that the smartphone or computer may alternatively be a hardwired (e.g. SPI, I2C, Ethernet or USB) to the external device 130.

For reliable operation, acceptable external battery life and an overall suitable patient experience, adequate proximity between the implantable device 110 and the external device 130 must be ensured through the placement and retention of the external device 130 during normal patient activity. Link integrity between the external device 130 and the implantable device 110 is influenced by the displacement between the antenna or antenna array of external device 130 and the implantable device 110. Factors such as physical distance, alignment, planarity and intervening material properties, among others, may play a role. As with any antenna system, whether for the transfer of power or the transfer of data or both, the design of, coupling between and matching of the respective transmit and receive antennas is of the utmost importance. To ensure appropriate placement of the external device 130 in relation to the associated implanted device 110, the external device 130 can be incorporated into a body covering 300 designed to cover the portion of the patient body BD having the implantable device 110 disposed therein. The body covering 300 is designed to appropriately maintain position of the external device 130, such as in terms of distance, alignment and planarity, in relation to the implantable device 110 so as to maximize or at least increase ("maximize" herein) the link integrity. For example, if the implantable device 110 is located in the thorax/torso/abdomen/groin region, the body covering 300 may comprise a belt, a bra, a shirt, a jacket, a harness, a vest, a shoulder brace, suspenders, a holster, a back brace, a necklace, a lanyard, underwear, a jock strap, a feminine napkin, pants, a body cavity insert, a garter belt, or an elastic band, to name a few. If the implantable device 110 is located in an upper limb, the body covering 300 may comprise an arm band, a bracelet, a glove, an elbow brace, or a sleeve, to name a few. If the implantable device 110 is located in a lower limb, the body covering 300 may comprise an ankle brace, a knee brace, an ankle bracelet, a shoe, a boot, a slipper, a sock, or a pant leg, to name a few. If the implantable device 110 is located in the head, the body covering 300 may comprise a hat, a hair clip, a tiara, glasses, earrings, nose rings, other piercings, devices worn behind the ear, a bandana, a sweat band, a headband, helmet, goggles, a ski mask or a dental appliance, to name a few. It may be appreciated that the body covering 300 may be worn or positioned over a portion of the body for an extended period of time or a short duration of time. Body coverings 300 utilized for an extended period of time may resemble conventional garments for comfort and ease of use or may comprise straps or braces to minimize or at least reduce ("minimize" herein) visibility under clothing. Likewise, body coverings 300 may be designed to attach to conventional garments so as to utilize existing portions of the garment as part of the body covering 300. Body coverings 300 utilized for short durations of time may be more bulky or may optionally include quick-release features. Such a body covering 300 may comprise a snap-on or friction based or magnetic or spring-loaded feature to allow the covering 300 to be easily applied and removed for short periods of time. Similarly, such snap-on or spring-loaded coverings 300 may only wrap partially around the portion of the body (e.g. arm, leg, torso, head, etc.) in order to be sized or adjusted to the patient and held in place by spring tension. In such embodiments, the coverings 300 may be repositioned by partially wrapping around the same portion of the body from the other side, thus maintaining link integrity while relieving any potential discomfort to the body. It may also be appreciated that body coverings 300 utilized for short durations of time may also resemble conventional accessories, such as pillows or padded chairs, which are positionable against the body.

Figure 6A:
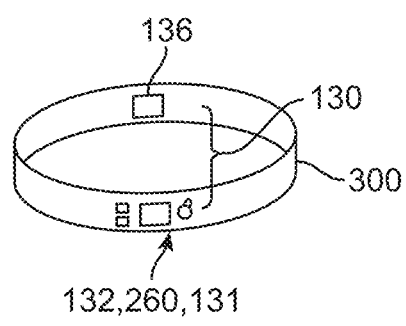
FIGS. 6A-6B illustrate embodiments of a body covering positionable in the region of the torso of the patient body.
Figure 6B:
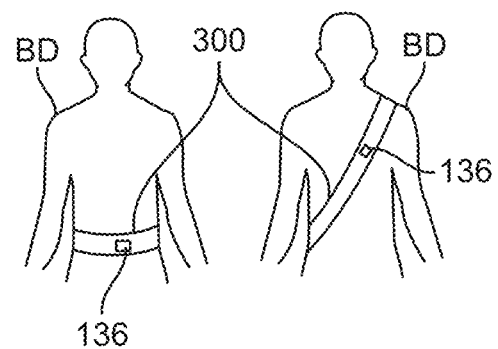

FIGS. 6A-6B illustrate embodiments of a body covering 300 positionable in the region of the torso of the patient body BD. FIG. 6A illustrates an embodiment of the body covering 300 having the form of a belt, band, strap, or other article of clothing and the external device 130 mounted thereon. In this embodiment, the external device 130 is shown as separate components, including a power supply 132 (e.g. a battery), a controller 260, and one or more antennas 136 integrated into the body covering 300. In this embodiment, the antenna 136 is disposed along the body covering 300 so that it resides in proximity to the surface of the skin at a designated location when the body covering 300 is worn appropriately. FIG. 6B illustrates the antenna 136 disposed in differing locations depending on how the body covering 300 is designed to be worn.

In this embodiment and in many of the embodiments described herein, the external device 130 includes a user interface 131 conveniently positioned along the body covering 300, allowing the user to view, interact, and/or adapt the operation of the overall system 100. Alternatively or additionally, user interface 131 can comprise an untethered handheld device (such as a key fob-like control, user controls in an application running on a smart phone or similar electronic device or custom programming device) for improved convenience of controlling the overall system 100, wirelessly coupled to communicate with the rest of the external system. In either case, the patient may utilize a variety of user interfaces (electrical, mechanical, acoustic, etc.) to use and configure the external device 130. For example, tactile pushbutton controls on the face of a body covering 300 may enable the user to select and configure operating modes of their device to suit their situation or their environment or the time of day or their activity level, etc. Examples may include increasing or decreasing therapy delivery (e.g. stimulation levels), changing programs, turning on/off therapy entirely. In other embodiments, controls may include capacitive touch sensors, including complex operations like swipes, taps, double taps, two-fingered taps, etc. to elicit different responses from the device. In such embodiments, means to prevent inadvertent activation of controls may include timeout features that disable the controls until enabling sequences of actions (e.g. specific gestures not readily executed by accident) are detected to re-enable the controls. In other embodiments, controls may include rotary or linear switches that have hard stop ranges (e.g. 0% and 100% for amplitude) or are relative in nature such as rotary switches that roll indefinitely in one direction or the other direction (no hard stops) to indicate an intention or "a direction" that is interpreted by the system controller. In other embodiments, control input to the device may be via voice.

In other embodiments, controls may be fully integrated and not require direct interaction with the user. Examples include smart sensors that detect (e.g. produce a signal related to) the location of the device (e.g. an accelerometer or a GPS sensor) and take action (e.g. make a therapy adjustment) immediately, such as a detected reclining position that activates a sleeping program. Such automated features may themselves be intelligent in nature. For example, smart sensors that detect the location of the device may do so by several means or combinations thereof. In some embodiments, this may be orientation alone via an accelerometer or other sensor that triggers the device to change the way the system is operating. In other embodiments, smart sensors (e.g. Bluetooth low energy, BLE sensor) or the detection of mated accessories may notify the system of the user's environment (e.g. the user is in their car) and adjust programs accordingly. More elaborately, such orientation may be combined with a proximity sensor established to further determine that a reclining position (detected by accelerometer) is in the location of the user's bed, or recliner. In other embodiments, time of day may be leveraged alone or in concert with other inputs to determine the nature of a change to make to the operation of the system in real time. In other embodiments, such transitions may be learned by way of the system acquiring data over time to determine the habits of patients and dynamically adjust therapy accordingly.

Still other fully integrated controls may involve the closed loop interrogation of the implant by the external to determine, for example, the level of impedances (or other device or physiological parameters) being observed by the implant and to adjust stimulation accordingly. Still other means for control may include skin contacting bioimpedance sensors that monitor for contact to skin to detect when the device has been properly attached and is ready for use. Still other means for control may include physiological parameters such as heartrate or blood pressure or respiration rate that are used to adjust stimulation accordingly. Other controls may be electromechanical in nature and provide features to automatically activate and deactivate the system during daily activities. For example, mating electromechanical latches or other electromechanical connectors (e.g. connectors comprising a sensor or otherwise configured to produce a signal) in an external system may close a circuit or activate a magnetic sensor to indicate the system has been connected and is fully ready for use. Conversely, un-mating such connectors intentionally or unintentionally can trigger safe shutdown of the system and entry in to low power mode to conserve battery life.

Referring back to the embodiments of FIG. 6A-6B, the body covering 300 having the form of a belt, band, strap, may have other forms. For example, in some embodiments, the antenna 136 is integrated into an inner belt with a Velcro® (or similar) exterior surface to which a mating outer belt is attachable or to which modular mating pockets are attachable. The outer belt includes the transmitter and battery. Thus, together the inner and outer belts complete the external device 130. Electrical connections could be made at a multitude of convenient contact sites or by cables or electrically active buttons or magnetically actuated connectors.

Figure 7A:
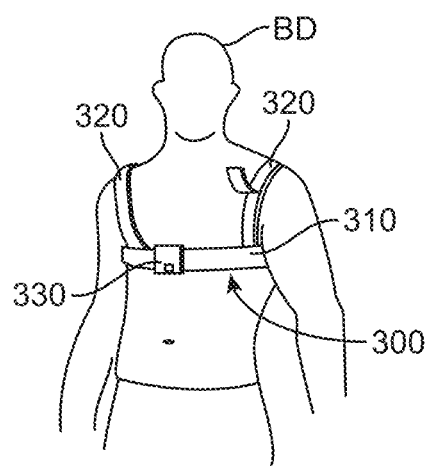
FIGS. 7A-7C illustrate a body covering in the form of a harness positionable over the torso.
Figure 7B:
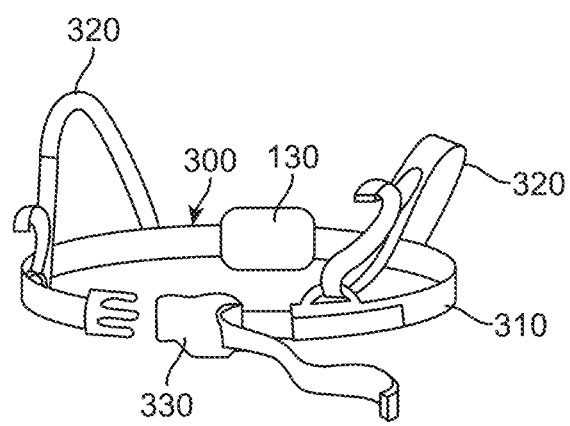

FIGS. 7A-7B illustrate a body covering 300 in the form of a harness positionable over the torso. In this embodiment, the body covering 300 includes a chest strap 310 that extends around the circumference of the chest of the patient's body BD and two shoulder straps 320 configured to extend over the shoulders of the patient's body BD when worn by the patient. The shoulder straps may be removable or fixed. The chest strap 310 clasps with a latch 330 disposed thereon. In this embodiment, the external device 130 is disposed along the chest strap 310 so as to reside on the patient's back when worn appropriately. In this embodiment, the position of the external device 130 can be adjusted by manipulation of the straps 310, 320. For example, the end portion of each shoulder strap 320 extends through a loop on the chest strap 310 and attaches back to itself such as by Velcro®. Each shoulder strap 320 may be shortened or lengthened individually, by repositioning the end portion along the Velcro®. Likewise, the end portion of the chest strap 310 extends through a loop on or near the latch 330 and attaches back on itself such as by Velcro®. The chest strap 310 can be shortened or lengthened by repositioning the end portion along its Velcro®. By desirably positioning the straps 310, 320 the external device 130 can be aligned so as to provide the optimal link integrity with the implantable device 110. Such alignment is then maintained each time the patient wears the body covering 300 since the straps 310, 320 maintain their position.

It may be appreciated that for reliable operation, acceptable external battery life and an overall suitable patient experience, adequate proximity between the implantable device 110 and the external device 130 must be ensured through the placement and retention of the body covering 300 during normal patient activity. Link integrity between the external device 130 and the implantable device 110 is influenced by the displacement between the external device 130 and the implantable device 110. As previously mentioned, factors such as physical distance, alignment, planarity and intervening material properties, among others, may play a role. As with any antenna system, whether for the transfer of power or the transfer of data or both, the design of, coupling between and matching of the respective transmit and receive antennas is of the utmost importance. In many embodiments, planar loop antennae are utilized for both the internal and the external antennae, optimized or at least improved ("optimized" herein) for the transmission and reception of RF energy in the MHz and low GHz regime. However, it may be appreciated that if different antenna topologies and/or frequencies of operation were chosen, many of the techniques described herein may be applied to similarly optimize performance for different antenna configurations (e.g. patch to patch, patch to dipole, dipole to dipole, patch to loop, dielectric gratings, optical systems), albeit with different results anticipated per technique owing to the physics involved (e.g. sensitivity to depth is a function of frequency and antenna topology, sensitivity to rotation in certain axes will be more significant with dipoles than with loops and less significant in other axes). Mechanisms to ensure link integrity between the external device 130 and implantable device 110 may be different depending on the site of implantation, the patient's activity level and the therapy's power profile.

Figure 7C:
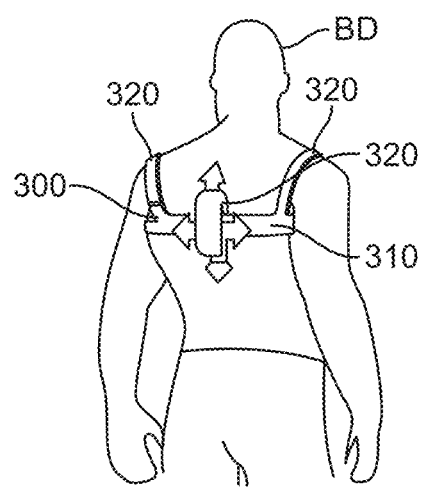

In some embodiments, the external device 130 is adjustably mounted on the body covering 300 to allow for fine adjustments while the patient is wearing the body covering 300. For example, FIG. 7C illustrates a body covering 300 in the form of an adjustable harness as in FIGS. 7A-7B. In this embodiment, the external device 130 is mounted on the chest strap 310 so that it can move relative to the chest strap 310 in a horizontal or vertical fashion as indicated by arrows. Such adjustment may be achieved with the use of a variety of mechanisms, such as sliders, gears, motors, magnetic positioners, rotators, Velcro® attachment sites, to name a few. Optionally, the mounted external device 130 can be removed from the body covering 300, such as for cleaning of the body covering 300. It may also be appreciated that in some embodiments the external device 130 is fixed to the body covering 300, even when external device 130 remains positionably adjustable.

Figure 8A:
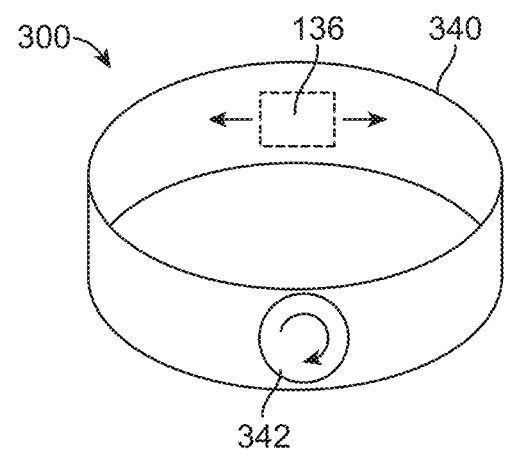
FIGS. 8A-8D illustrate embodiments of a body covering having an external device, particularly an antenna, whose position is finely adjustable in relation to the patient's body while the patient is wearing the body covering.
Figure 8D:
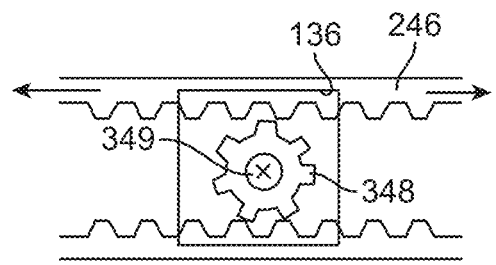
Figure 8C:
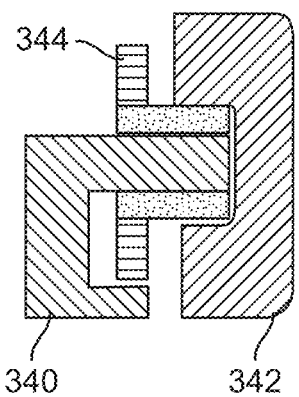
Figure 8B:
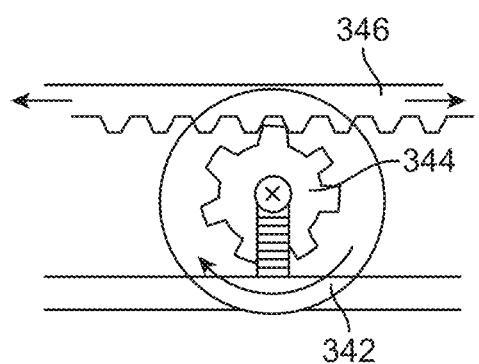
Figure 9A:
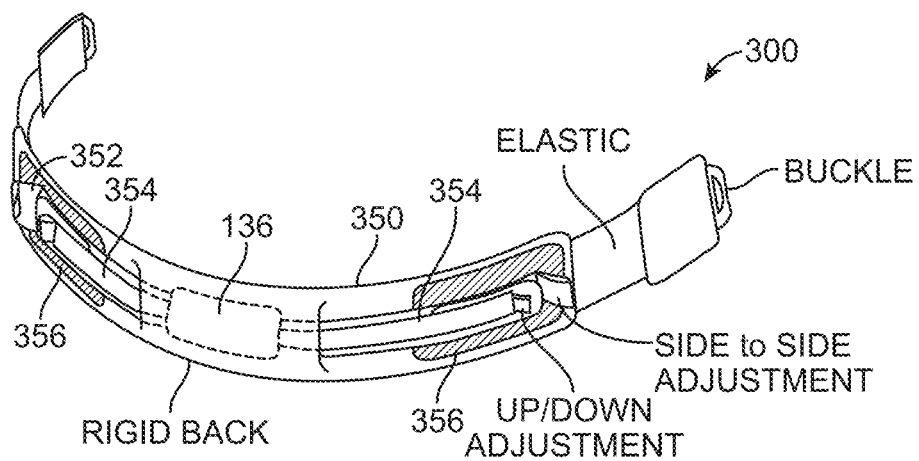
FIGS. 9A-9F illustrates another embodiment of a body covering having an external device, particularly an antenna, whose position is finely adjustable in relation to the patient's body while the patient is wearing the body covering.
Figure 9B:
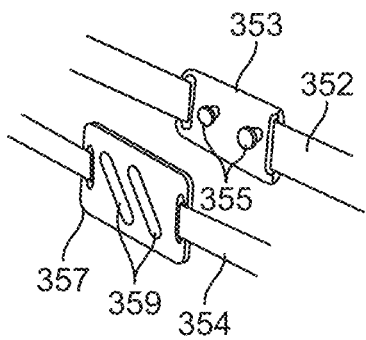
Figure 9E:
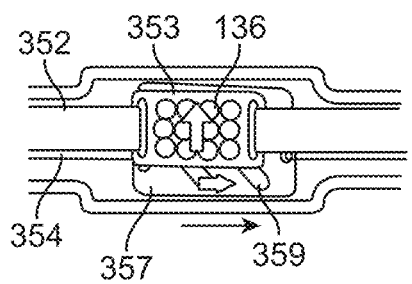
Figure 9C:
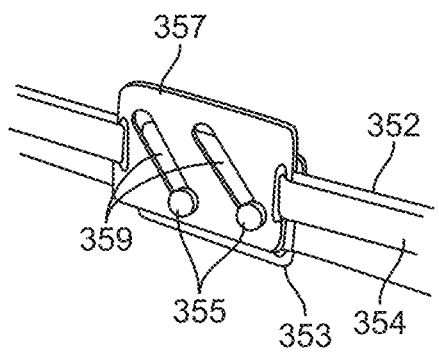
Figure 9F:
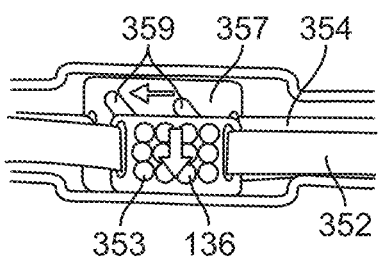
Figure 9D:
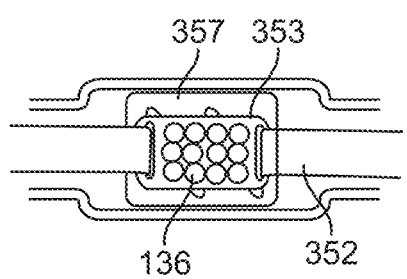

FIGS. 8A-8D illustrate embodiments of a body covering 300 having an external device 130, particularly an antenna 136, whose position is finely adjustable in relation to the patient's body BD while the patient is wearing the body covering 300. In this embodiment, as illustrated in FIG. 8A, the body covering 300 has the form of a slidable strap, strap 340, that may be positionable around any portion of the patient body BD, such as a chest, waist, arm, leg or head. Body covering 300 can comprise the rack and pinion mechanism shown in FIGS. 8B-D, including an adjustment knob 342 and gear 344. The strap 340 includes an antenna 136. When the strap 340 is worn as a belt, the knob 342 may appear as a belt buckle. Rotation of the knob 342 finely adjusts the position of the antenna 136 in relation to the strap 340 by moving the antenna 136 to the left or right, as indicated by arrows. FIG. 8B provides a close up illustration of the knob 342 which is attached to gear 344. The gear 344 engages a ripcord 346 so that rotation of the knob 342 causes the gear 344 to rotate, which in turn engages the ripcord 346 causing the ripcord 346 to move laterally along the strap 340, as indicated by arrows. FIG. 8C provides a cross-sectional view of the knob 342 of FIG. 8B. The ripcord 346 extends to at least the antenna 136. FIG. 8D provides a close up illustration of the antenna 136 which is attached to another gear 348, which in turn engages the ripcord 346. As the ripcord 346 moves, the gear 348 rotates and moves laterally in relation to the strap 340. Since the gear 348 is attached to the antenna 136 via a bearing 349, the antenna 136 does not rotate while the gear 348 rotates. Instead, the antenna 136 moves laterally or translates along the strap 340 along with the gear 348. This allows the lateral position of the antenna 136 to be finely adjusted by rotation of the knob 342. FIG. 9A illustrates another embodiment of a body covering 300 having an external device 130, particularly an antenna 136, whose position is finely adjustable in relation to the patient's body BD while the patient is wearing the body covering 300. In this embodiment, as illustrated in FIG. 9A, the body covering 300 has the form of a strap 350 that may be positionable around any portion of the patient body BD, such as a chest, waist, arm, leg or head. In this embodiment, the strap 350 includes an antenna 136 which is attached to a variety of adjustment straps, including a lateral adjustment strap 352 and a vertical adjustment strap 354. The adjustment straps 352, 354 extend along the strap 350 and are fastenable to the strap 350, such as by Velcro®. FIG. 9A illustrates a fastening area 356 to which the lateral adjustment strap 352 is attachable, such as by mating a section of small flexible hooks on one side of the lateral adjustment strap 352 to small flexible loops along the fastening area 356 (i.e. Velcro®). In this embodiment, the vertical adjustment strap 354 is attached to the lateral adjustment strap 352 by a similar mechanism. Thus, the vertical adjustment strap 354 is indirectly fastenable to the strap 350. To adjust the position of the antenna 136 laterally and/or vertically, the associated strap(s) are unfastened from the strap 350 and pulled laterally, along the length of the strap 350. FIGS. 9B-9F illustrate a mechanism for allowing such movement by pulling laterally. FIG. 9B shows the lateral adjustment strap 352 having a bracket 353 with studs 355. FIG. 9B also shows the vertical adjustment strap 354 having a bracket 357 with diagonal slats 359. The brackets 353, 357 are mateable by passing the studs 355 through the slats 359 as illustrated in FIG. 9C. The antenna 136 is disposed on the backside of the bracket 353, attached to the lateral adjustment strap 352, as illustrated in FIG. 9D. When the vertical adjustment strap 354 is pulled laterally to the right, as illustrated in FIG. 9E, the strap 354 pulls the bracket 357 to the right. The studs 355 on bracket 353 naturally rise within the diagonal slats 359, thereby moving the bracket 353 (and attached antenna 136) vertically upwards. When the vertical adjustment strap 354 is pulled laterally to the left, as illustrated in FIG. 9F, the strap 354 pulls the bracket 357 to the left. The studs 355 on bracket 353 naturally lower within the diagonal slats 359, thereby moving the bracket 353 (and attached antenna 136) vertically downwards. To move the antenna 136 laterally, the lateral adjustment strap 352 and the vertical adjustment strap 354 may be moved together to maintain vertical position while adjusting the lateral position. Once the desired positions are achieved, the straps 352, 354 are then reattached to the strap 350.

Figure 10A:
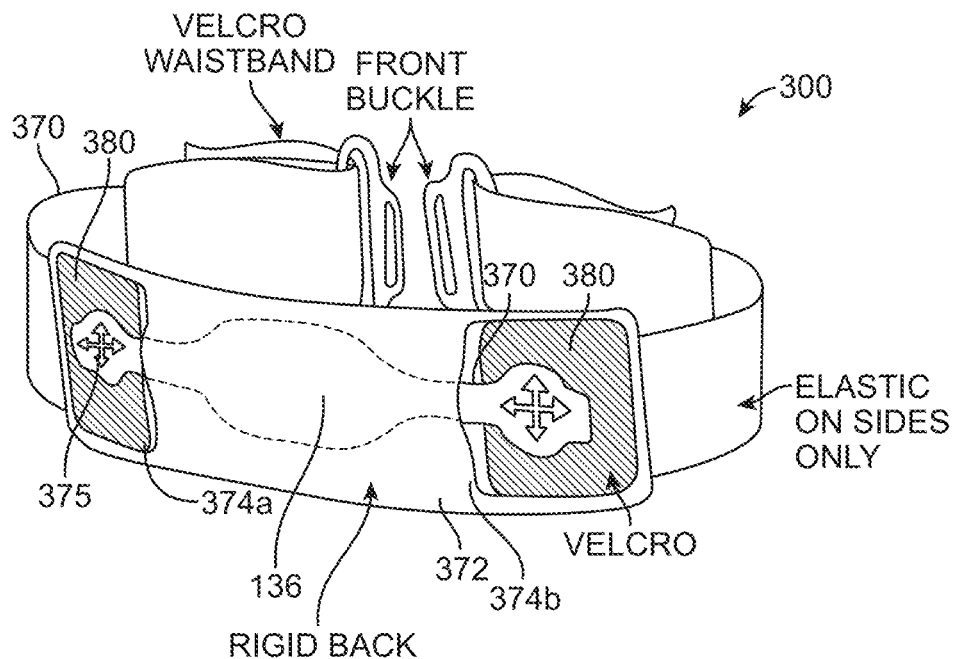
FIGS. 10A-10B illustrates yet another embodiment of a body covering having an external device, particularly an antenna, whose position is finely adjustable in relation to the patient's body while the patient is wearing the body covering.
Figure 10B:
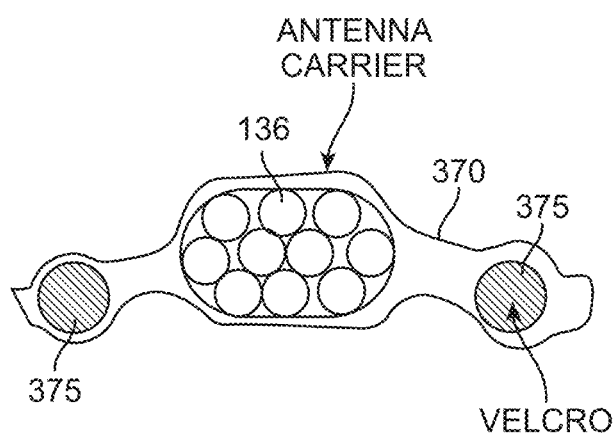

FIGS. 10A-10B illustrate another embodiment of a body covering 300 having an external device 130, particularly an antenna 136, whose position is finely adjustable in relation to the patient's body BD while the patient is wearing the body covering 300. In this embodiment, as illustrated in FIG. 10A, the body covering 300 has the form of a strap 370 that may be positionable around any portion of the patient body BD, such as a chest, waist, arm, leg or head. The strap 370 includes a sleeve 372 with openings 374a, 374b which allow passage of the antenna 136 therethrough. In this embodiment, the antenna 136 is mounted on a carrier 376, as illustrated in FIG. 10B. Thus, the carrier 376 and the associated antenna 136 are passable through the openings 374a, 374b and positionable within the sleeve 372. The carrier 376 includes at least one fastening area 375 which is attachable to a fastening area 380 on the strap 370. In this embodiment, the fastening area 375 comprises a portion of Velcro®, such as small flexible hooks, which attach to another portion of Velcro®, such as small flexible loops, on the fastening area 380 of the strap 370. Thus, to reposition the antenna 136, the carrier 376 is unfastened from the strap 370 (by removing the fastening area 375 from the fastening area 380), moved vertically and/or horizontally, and refastened to the strap 370 (by attaching the fastening area 375 to a new portion of the fastening area 380).

FIGS. 11A-11C illustrate another embodiment of a body covering 300 having an external device 130 whose position is finely adjustable in relation to the patient's body BD while the patient is wearing the body covering 300. In this embodiment, as illustrated in FIG. 11A, the body covering 300 also has the form of a strap 400 that may be positionable around any portion of the patient body BD, such as a chest, waist, arm, leg or head. The external device 130 is disposed along the length of the strap 400 while the two ends 402a, 402b of the strap join together, with the use of a clasp 404, forming a continuous loop. In this embodiment, the external device 130 is disposed midway along the length of the strap 400, opposite from the joined ends, so as to reside against a patient's back when the ends 402a, 402b are joined near the front of the patient's waist or chest. The external device 130 is attached (fixedly or removably) to a pull string 406 which extends along the strap 400. In this embodiment, the pull string 406 extends along the length of the strap 400 and is longer than the overall length of the strap 400. FIG. 11B provides a close-up illustration of one of the ends 402a of the strap 400 showing the pull string 406 extending beyond the end 402a. In this embodiment, the pull string 406 extends through an elongate cavity 408 which traverses the length of the strap 400. FIG. 11C provides a cross-sectional view of the end 402a illustrated in FIG. 11B, showing the pull string 406 within the cavity 408. When the pull string 406 is pulled from either end 402a, 402b, the attached external device 130 moves with the pull string 406 in relation to the strap 400, and therefore in relation to the portion of the patient's body that the strap 400 is covering. Once the external device 130 is desirably positioned, the location of the device 130 can be fixed in relation to the strap 400 by attaching the pull string 406 to the strap 400. The pull string 406 can be attached to the strap 400 by a variety of mechanisms, including hooks, snaps, claps, fasteners and adhesives, to name a few. In this embodiment, the pull string 406 is attached to the strap 400 by Velcro® 410, wherein a portion of the Velcro® 410a (such as the loops) are disposed on the pull string 406 and the other portion of the Velcro® 410b (such as the hooks) are disposed on the strap 400. The pull string 406 is then attached to the strap 400 by pressing the portion of the Velcro® 410 on the pull string 406 to the other portion of the Velcro® 410b on the strap 400. Additional adjustments can then be made by repeating the steps of pulling the pull string 406 and fixing the pull string 406 to the strap 400.

Figure 12:
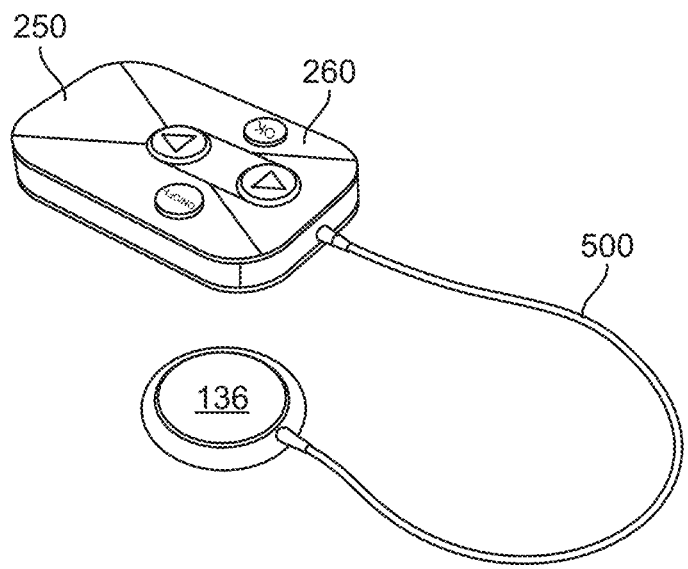
FIG. 12 illustrates an embodiment wherein the power source and controller are surrounded by a single enclosure, and an antenna is tethered to this enclosure via a wire.
Figure 13:
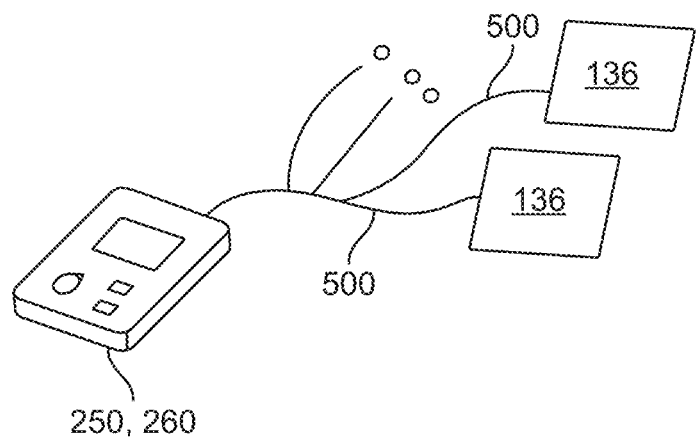
FIG. 13 provides a schematic illustration of an embodiment similar to FIG. 12 with two antennas.
Figure 14:
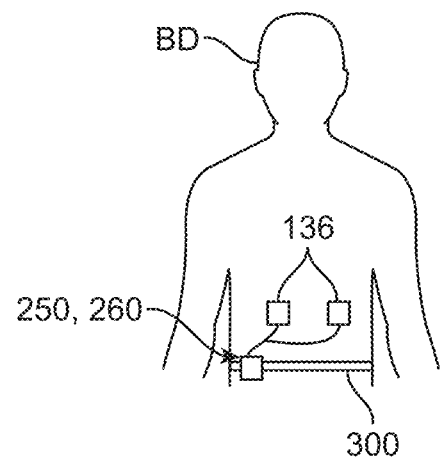
FIG. 14 illustrates the enclosure attached to a body covering which is extending around the patient's waist, and the antennas fixated to a portion of the patient's body which is not covered by the body covering.

As mentioned previously, the components of the external device 130, such as one or more antennas 136, a controller 260 (such as for controlling communications or other operations of the overall system, e.g. therapeutic parameters, neuromodulation parameters, closed-loop adaptation of therapy based on feedback from sensors), and a power source 250 such as a battery, can be combined into a single discrete component or divided into several components, optionally disposed on various external devices. It may also be appreciated that at least some of the components may be disposed on the body covering 300 while others are attached to the body covering 300 by cords or tethers allowing varied positioning of the components. FIG. 12 illustrates an embodiment wherein the power source 250 (e.g. battery) and controller 260 are surrounded by a single enclosure, and an antenna 136 is tethered to this enclosure via a wire (e.g. cable or interconnect 500). There, a user interface and/or display may be implemented (e.g. on the enclosure surrounding the power source and controller), allowing the user to view, interact, and/or adapt the operation of the overall system 100. The user interface could comprise button(s), a touchscreen display, knob(s), keyboard, keypad, display, microphone, light, speaker and/or other components configured for user input and/or user output. Depending on the intended use and application of the overall system 100, this user interaction with the system or apparatus can have varying levels of complexity. FIG. 13 provides a schematic illustration of a similar embodiment. In this embodiment, two antennas 136 are tethered to a single enclosure, housing portions of the external device 130 such as the power source 250 and controller 260. FIG. 14 illustrates the enclosure (housing portions of the external device 130) attached to a body covering 300 which is extending around the patient's waist, and the antennas 136 fixated to a portion of the patient's body which is not covered by the body covering 300. In this instance, the antennas 136 are fixated to the patient's back. The one or more antennas 136 could be attached to the skin of the patient directly through an adhesive, as illustrated. However, it may be appreciated that the antennas may be attached to another body covering 300 that covers another portion of the patient's body. In either case, the antenna 136 can be placed so as to optimize link integrity with the implantable device 110 while the bulk of the components of the external device are placed in a more comfortable or otherwise convenient location.

The antennas 136, adhesives, and/or other attachment elements can be designed to be disposable after several days, weeks, or months of operation. Alternatively, the antennas 136, adhesives or other attachment elements, or other component of the external device 130, can be more permanent, lasting years or longer. A battery (or a battery pack) can be charged while in the enclosure, it could be removable from the enclosure to be charged separately, or it could be removable primary cell battery so it can be replaced with another primary cell battery. These battery configurations would allow the user to have multiple batteries for the one external device and charge one battery while the other is in use with the external device.

Figure 15A:
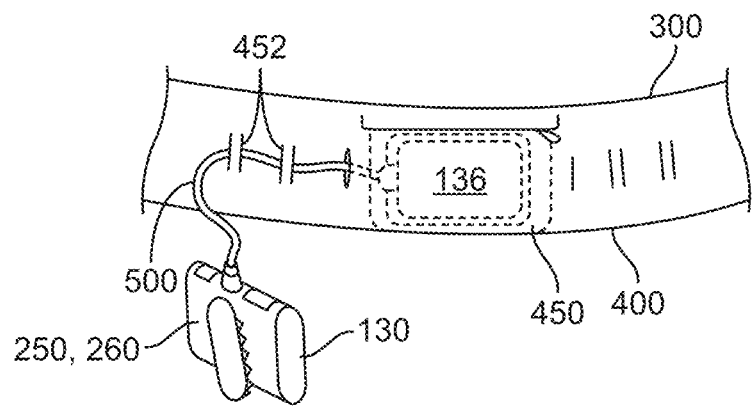
FIGS. 15A-15B illustrate an embodiment wherein an antenna is positioned along a body covering while the remainder of the external device is tethered thereto by a wire.
Figure 15B:
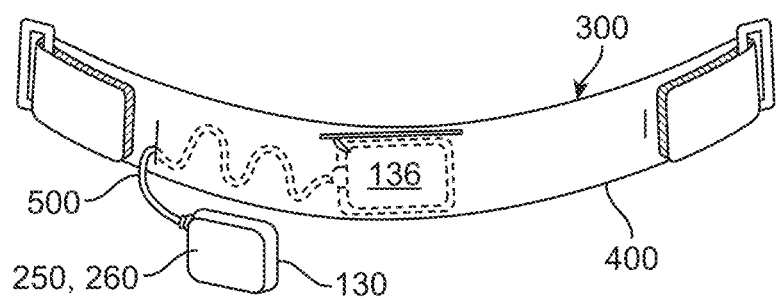
Figure 16:
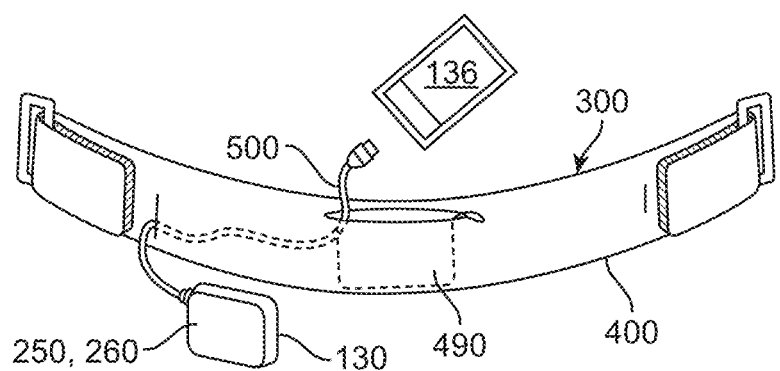
FIG. 16 illustrates disconnecting the wire from the antenna, or otherwise untethering the components.
Figure 53A:
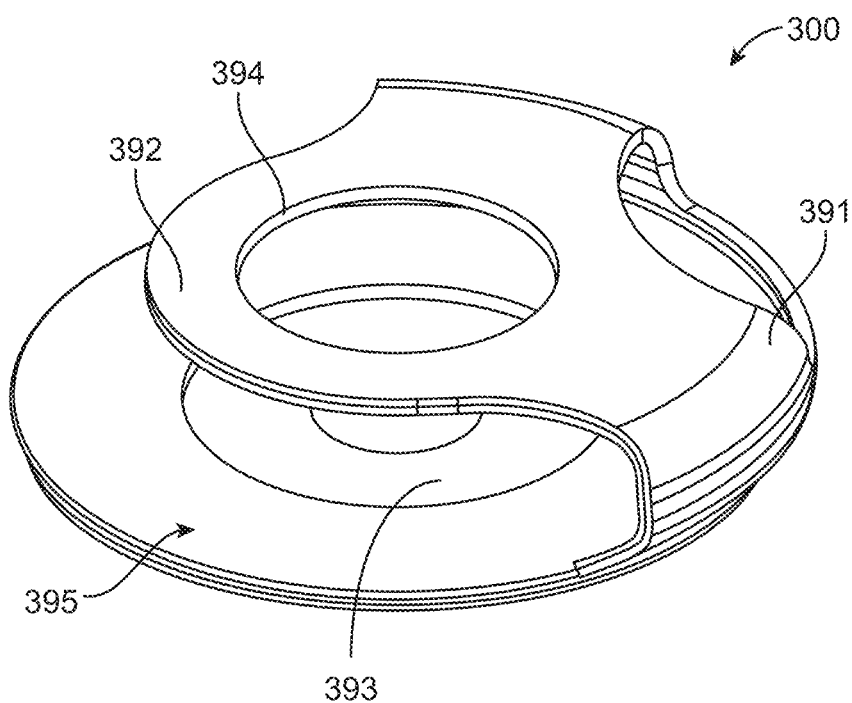
FIGS. 53A-53D illustrate an example embodiment of a body covering comprising a clip with an adhesive backing.
Figure 53B:
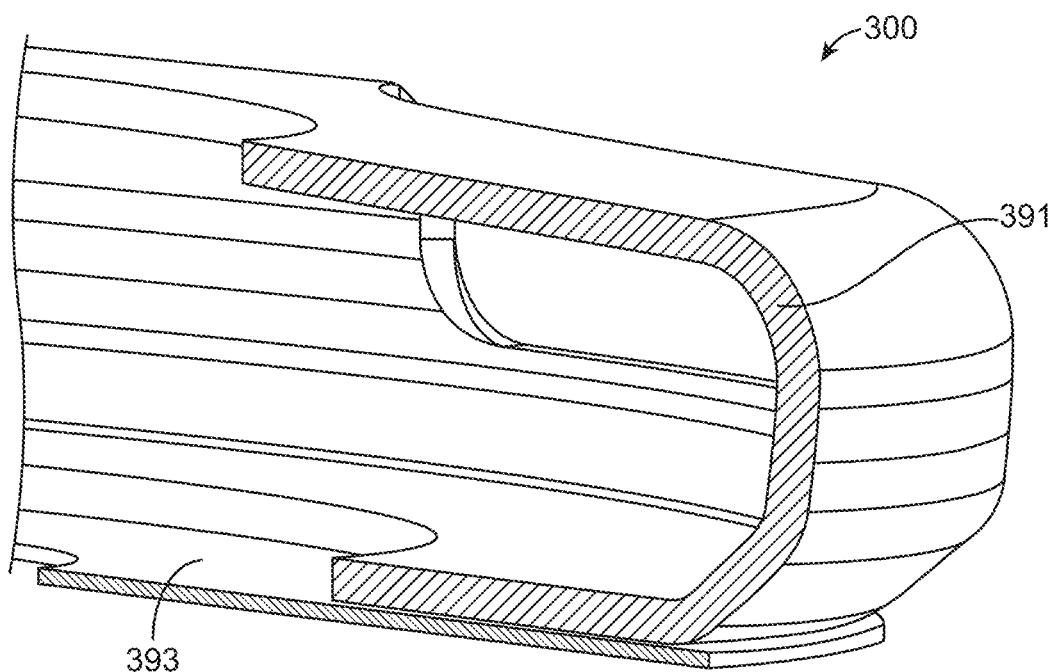
Figure 53C:
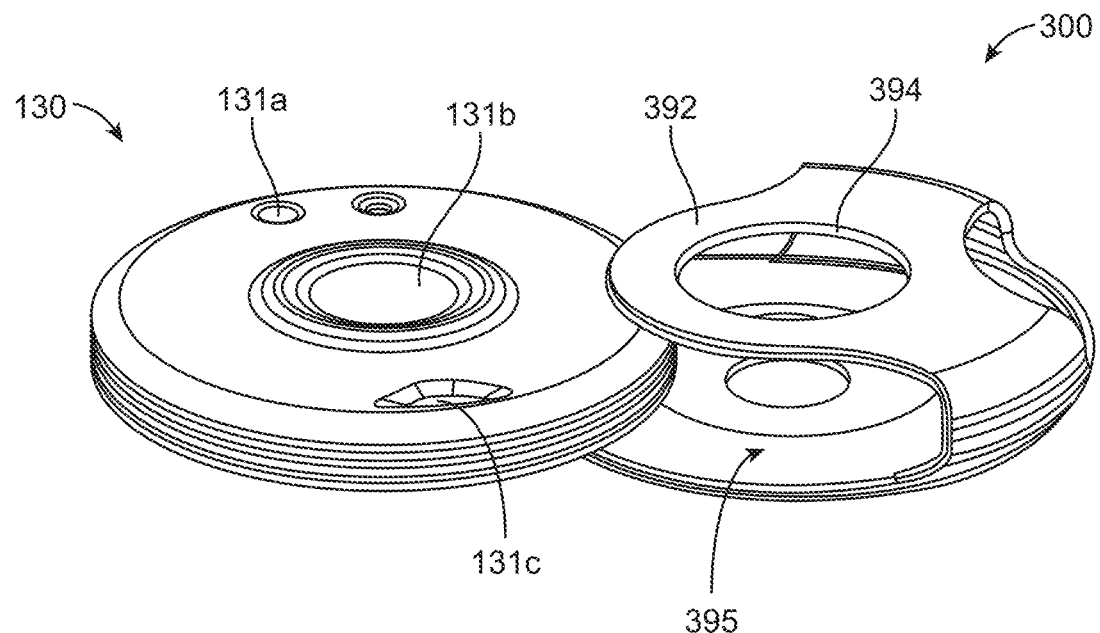
Figure 53D:
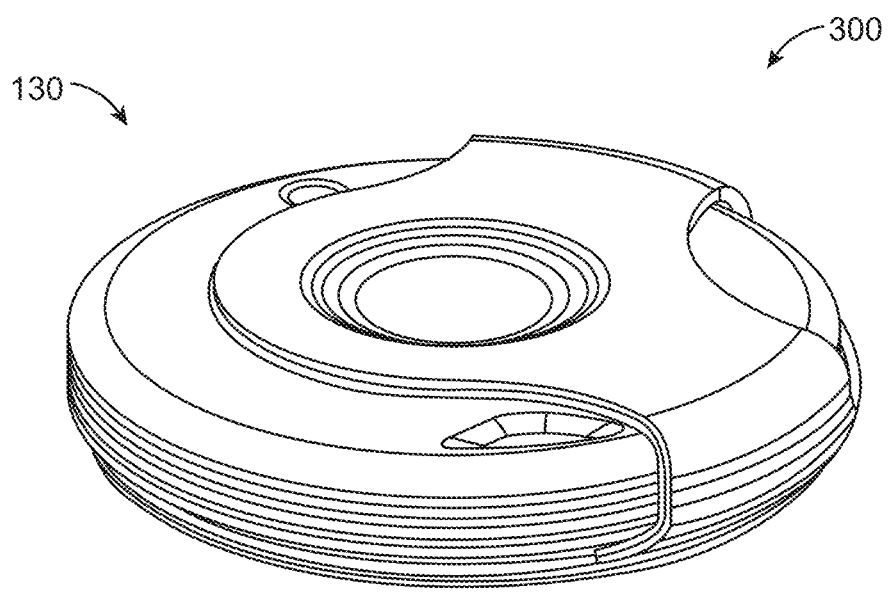

It may be appreciated that, alternatively, one or more antennas 136 may be held in place by a body covering 300 while portions of the external device 130 are disposed elsewhere, such as in a pocket of a garment or clipped to a conventional belt worn by the patient. In some embodiments, body covering 300 comprises a clip which can include an adhesive backing, such as a clip configured to adhesively attach to the patient's skin or a patient garment. In FIGS. 51A-D, body covering 300 includes an example clip configuration, including housing 391. Housing 391 includes bottom portion 396 and top portion 392, which collectively define a cradle portion or other cavity, cavity 395. An adhesive layer and/or backing, adhesive layer 393, can be attached to bottom portion 396. As shown in FIGS. 53C-D, an external device 130 can be inserted into and removed from cavity 395, such as an external device 130 comprising controls 131a-c (e.g. user input components such as buttons or other switches and/or user output components such as lights) as shown. In some embodiments, external device 130 comprises a centrally located button 131b as shown, and housing 392 comprises a centrally located hole, opening 394, which provides user (e.g. patient) access to control 131b when external device 130 is positioned within cavity 395. FIGS. 15A-15B illustrate an embodiment wherein an antenna 136 is positioned along a body covering 300 while the remainder of the external device 130 is tethered thereto by a wire (e.g. cable or interconnect 500). The tethered portion of the external device 130 may include components such as the power source 250 and controller 260, along with an optional user interface. In this embodiment, the body covering 300 comprises a strap 400 and the antenna 136 is removably positionable within a pocket 450 in the strap 400. The pocket 450 holds the antenna 136 in a desirable position relative to the implantable device 110 when the body covering 300 is appropriately worn by the patient. The wire 500 is typically routed along the body covering 300 to the remainder of the external device 130 so as to minimize interaction or entwinement with the wire 500 by the patient. FIG. 15A illustrates the wire 500 extending along an exterior portion of the body covering 300, particularly lengthwise along the strap 400. The wire 500 is held in place by openings 452 in the strap 400 which function similarly to belt loops. FIG. 15B illustrates the wire 500 extending along an interior portion of the body covering 300, again lengthwise along the strap 400. In this instance, slack in the wire 500 is maintained within the body covering 300. In either case, the antenna 136 may be removed from the pocket 450 in the strap 400 by disconnecting the wire 500 from the antenna 136, or otherwise untethering the components, as illustrated in FIG. 16. Likewise, the remainder of the external device 130 may be removed from the body covering 300. This may be desired to, for example, launder or clean the body covering 300, or to change out any of the components.

Figure 17:
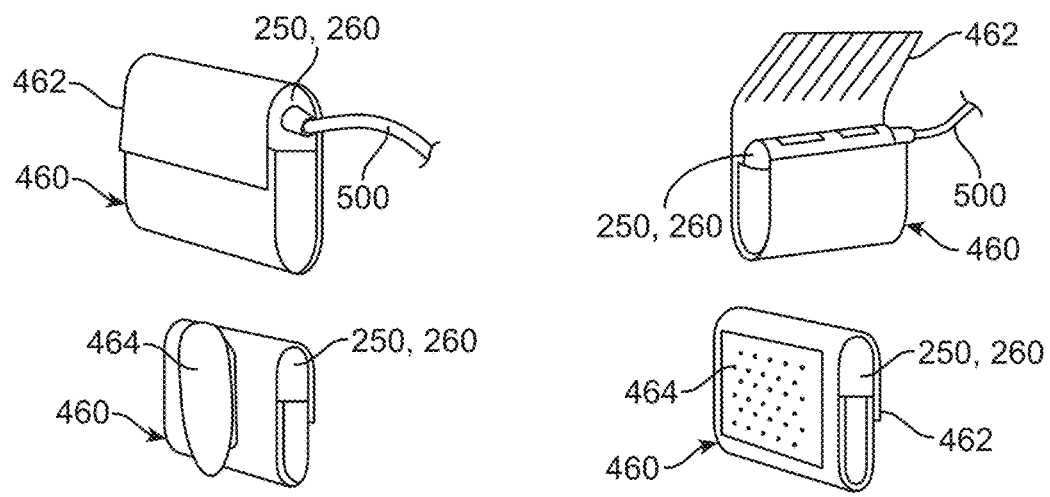
FIG. 17 illustrates various holding apparatuses for holding the remainder of the external device when not included in the body covering.
Figures 18A, 18B:
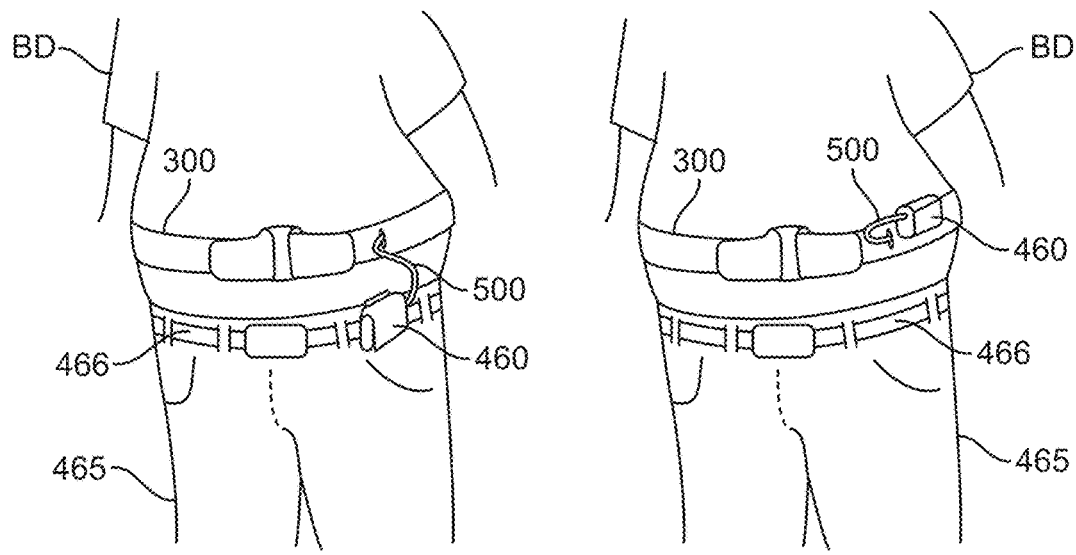
FIG. 18A illustrates an embodiment of an external device and body covering worn by a patient wherein the body covering is positioned around the waist of the patient, above the patient's pants, and the external device is disposed on the patient's waistband.
FIG. 18B illustrates an embodiment of an external device and body covering worn by a patient such that the body covering is positioned around the waist of the patient, above the patient's pants, and the external device is disposed outside of the body covering but attached thereto.
Figure 19:
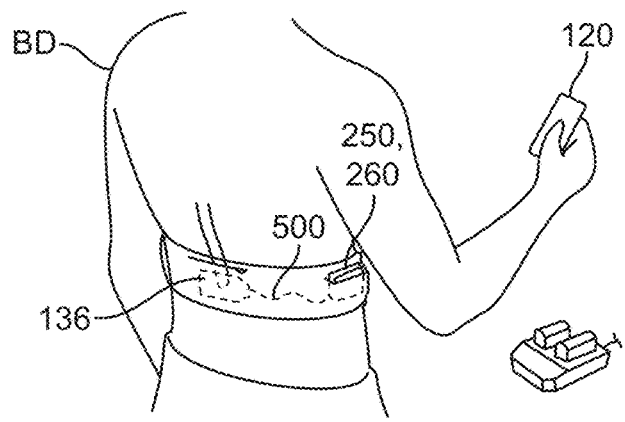
FIG. 19 illustrates a similar embodiment, wherein the external device extends throughout the body covering yet is removable from the body covering.

FIG. 17 illustrates various holding apparatuses 460 for holding the remainder of the external device 130 when not included in the body covering 300. For example, the components of the remainder of the external device 130, such as the power source 250 and controller 260, may be housed in an enclosure which is positionable in an apparatus 460. In some embodiments, the apparatus 460 has a flap 462 which is pulled back to reveal an internal cavity for placing the enclosure within. The flap 462 then covers the enclosure to hold it therein. Accessories, such as wires 500 may extend from the enclosure while in the holding apparatus 460. Optionally, the apparatus 460 may include an attachment mechanism 464, such as a clip, clasp, fastener, adhesive, or Velcro®, to name a few, for attachment to another article. In some embodiments, a clip comprises an adhesive portion for adhesively attaching the clip to the patient's body or a patient garment. FIG. 18A illustrates an embodiment of an external device 130 and body covering 300 (such as in FIG. 16) worn by a patient. Here, the body covering 300 is positioned around the waist of the patient, above the patient's pants 465. As shown, a portion of the external device 130 is disposed within the body covering 300 and a portion is disposed within a holding apparatus 460, the portions tethered together by a wire 500. The holding apparatus 460 is attached to a conventional belt 466 positioned along the patient's pants 465. FIG. 18B illustrates a similar embodiment of an external device 130 and body covering 300 worn by a patient such that the body covering 300 is positioned around the waist of the patient, above the patient's pants 465. However, in this embodiment, a portion of the external device 130 is disposed within the body covering 300 and a portion is disposed outside of the body covering 300 but attached thereto. Again, the portions tethered together by a wire 500. FIG. 19 illustrates a similar embodiment, wherein the external device 130 extends throughout the body covering 300 yet is removable from the body covering 300. Here, the antenna 136 of the external device 130 is shown in a pocket 450 within the body covering 300 while the remainder of the external device 130 (e.g. the power supply 250 and controller 260) are disposed in another pocket within the body covering 300, the portions joined together by a wire 500. In this embodiment, the antenna 136 is positioned along the patient's back while the remainder of the external device 130 is positioned along the patient's side. This layout may provide more comfort and convenience for the patient.

Figure 20A:
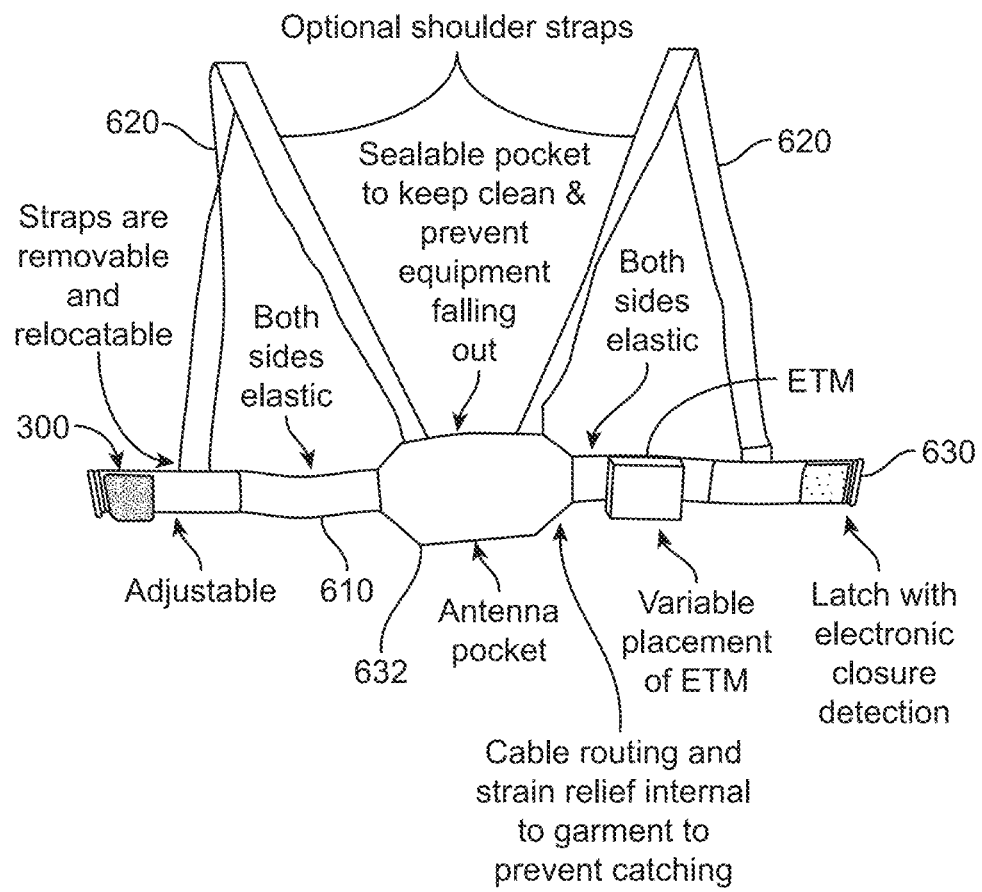
FIGS. 20A-20B illustrate an embodiment of an external device and body covering having various features to increase the usability and comfort for the patient while maintaining desired positioning and alignment for maximum link integrity with the internal implant.
Figure 20B:
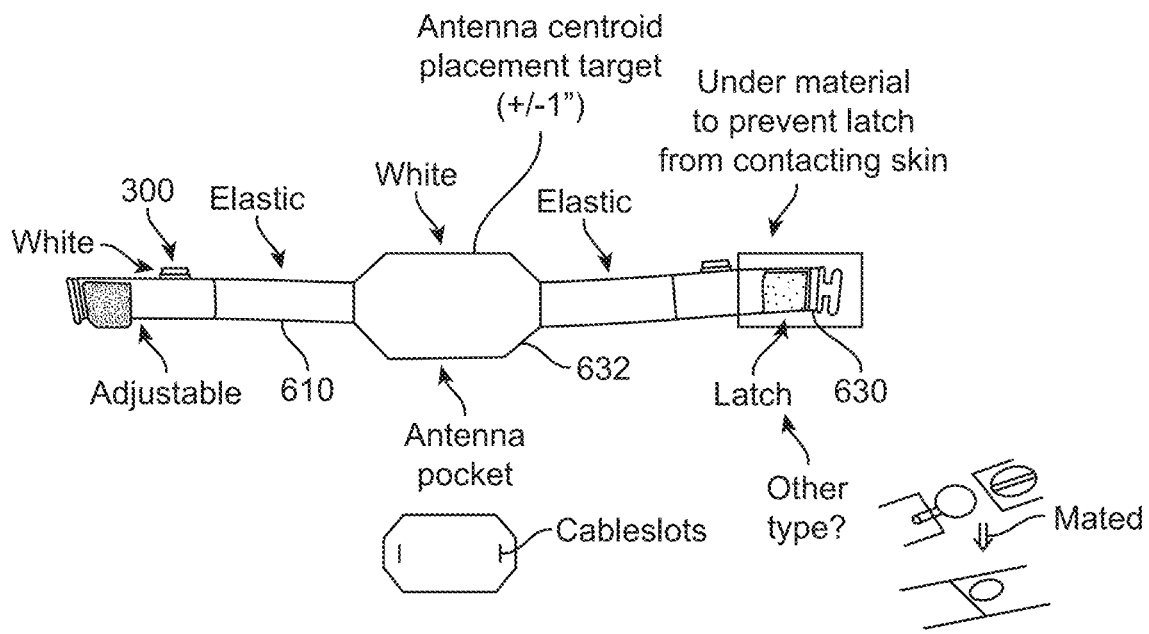

FIGS. 20A-20B illustrate an embodiment of an external device 130 and body covering 300 having various features to increase the usability and comfort for the patient while maintaining desired positioning and alignment for maximum link integrity with the internal implantable device 110. In this embodiment, the body covering 300 is similar to that which is described and illustrated in relation to FIGS. 7A-7B, wherein the body covering 300 is in the form of a harness positionable over the torso of the patient. As illustrated in FIG. 20A, the body covering 300 includes a chest strap 610 that extends around the circumference of the chest of the patient's body BD and two shoulder straps 620 configured to extend over the shoulders of the patient's body BD when worn by the patient. The chest strap 610 clasps with a latch 630 disposed thereon. In this embodiment, the body covering 300 includes a pocket 632 for holding a portion of the external device 130, such as an antenna 136. The pocket 632 is disposed along the chest strap 610 so as to reside on the patient's back when worn appropriately. In this embodiment, the chest strap 610 includes elastic portions to provide a snug fit to the patient's body BD, reducing movement of the body covering 300 in relation to the body BD. In addition, the shoulder straps 620 can be lengthened or shortened to adjust the position of the body covering 300 relative to the body BD and to maintain such position. Optionally, the shoulder straps 620 can be relocated along the chest strap 610 to optimize fit. Alternatively, the shoulder straps 620 may be removed, as illustrated in FIG. 20B.

To electrically interconnect external device 130 subcomponents (e.g. transmitter and battery, transmitter and antenna) in any of the embodiments described herein, various means may be used. Discrete wires or cables or lengths of flex circuits may be employed to interconnect modules. To route and retain such wires, options include: tubes, channels, knots, clips, button flaps, periodically spaced holes to weave through, Velcro® loops, zip ties, twist ties, magnetic clasps, etc. Conversely, garment integrated conductors may be employed that are tapped into at the ends or along the conductor to allow for devices to be positioned optimally for patient comfort while still making desired electrical connection. Features such as those described herein are desired to ensure easy maintenance of the external accessory which may require daily disassembly, cleaning and reassembly with the same or substitute components. Means to facilitate this in a reliable and convenient manner are important and may include design attributes such as fabric socks or sleeves that are machine washable or disposable/replaceable that slide over and interlock with electronics to form a comfort layer between the housing and the skin while ensuring the antenna and the electronics are robustly held and positioned during normal use. Furthermore, in other embodiments, electrical connections in such washable components may be permanent by way of conductive materials, fibers or wires that are woven, stitched, ironed or manually threaded into the material forming permanently prewired body coverings.

It may be appreciated that although the embodiments of the external devices and body coverings illustrated herein have primarily been shown to be positioned around the torso of the patient's body, many of these same embodiments can be positioned around other parts of the body for communication with implantable devices 110 in these other locations. For example, a belt or strap as described and illustrated to fit around a torso can alternatively be fit around an arm, leg, wrist, hand, finger, ankle, foot, neck or head, to name a few. Likewise, the body covering 300 can have the form of a sock, glove or the base features of a variety of conventional garments, wherein aspects of the covering 300 are specific to the present invention and ultimate methods of use.

Figure 21A:
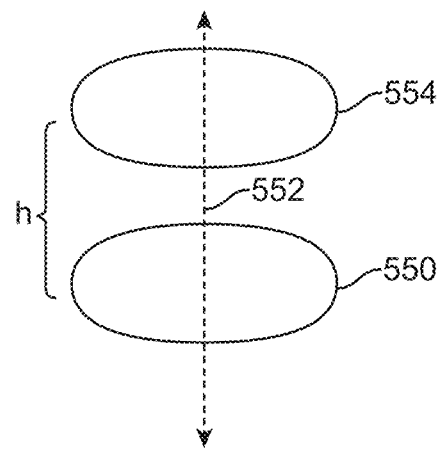
FIGS. 21A-21C schematically illustrate examples of alignment and misalignment of an antenna.
Figure 21B:
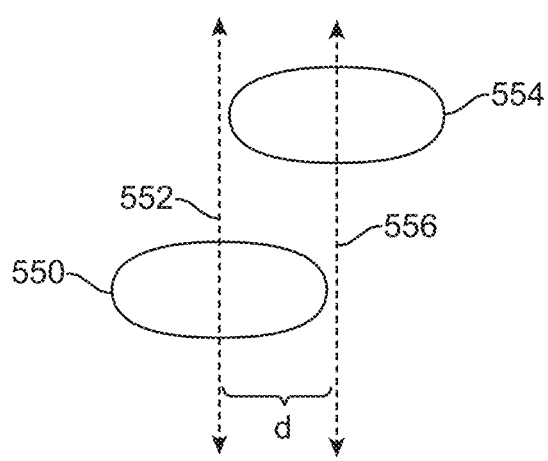
Figure 21C:
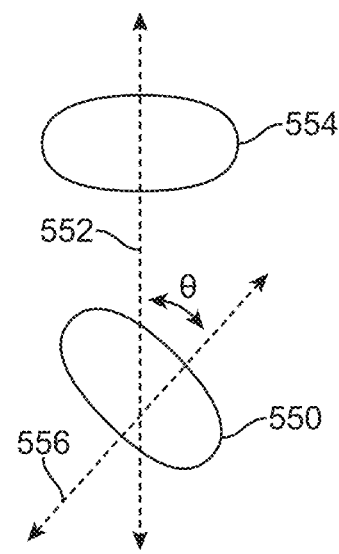

In some instances, the body covering 300 can be easily positioned so as to align the antenna 136 of the external device 130 with the implantable device 110. However, in other instances, the implantable device 110 may be difficult to locate, positioned within the anatomy at an inconvenient location, or otherwise more difficult to locate, align an external antenna 136 thereto and maintain such alignment, such as with the use of a body covering 300. A well aligned antenna 136 optimizes link integrity and thereby provides precise, controlled modulation of specific nerves or tissues via the implantable device 110 to induce sufficient physiological effects for effective therapies. However, a misaligned antenna 136 can lead to inefficient and/or ineffective therapy for the patient and ultimate therapy failure. FIGS. 21A-21C schematically illustrate examples of alignment and misalignment. FIG. 21A illustrates an external antenna represented by a circular shape 550 having a central axis 552 coaxial to the circular shape 550. The circular shape 550 is shown aligned with an antenna of an implanted device represented by another circular shape 554 so that the central axis 552 is also coaxial to the another circular shape 554. In this regard, the antennas are desirably aligned. The antennas are also desirably spaced apart by a distance h which may vary according to surgical site, surgical approach, clinical indication or patient anatomy between a few millimeters (just beneath the skin) to a few centimeters (deeper tissue). FIG. 21B illustrates an example of misalignment. Here, an external antenna is again represented by a circular shape 550 having a central axis 552 coaxial to the circular shape 550. However, the circular shape 550 is shown misaligned with an antenna of an implanted device represented by another circular shape 554 so that the central axis 552 is not coaxial to the another circular shape 554. A central axis 556 coaxial to the another circular shape 554 is offset from the central axis 552 by a distance d which may vary in the range of the diameter(s) of the respective antenna. A small antenna, beneath a larger antenna may allow more flexibility in d before performance is notably degraded. Conversely, two very small antenna may be more susceptible to degradation with smaller displacements. Thus, the antennas are not desirably aligned leading to suboptimal or insufficient performance. FIG. 21C illustrates another example of misalignment. Here, an external antenna is again represented by a circular shape 550 having a central axis 552 coaxial to the circular shape 550. However, the circular shape 550 is shown misaligned with an antenna of an implanted device represented by another circular shape 554 so that the central axis 552 is not coaxial to the another circular shape 554. A central axis 556 coaxial to the another circular shape 554 is tilted or rotated from the central axis 552 by θ degrees. Thus, the antennas are not desirably aligned leading to suboptimal or insufficient performance. Different antenna configurations will have different sensitivities to h, d, and θ. For a loop to loop configuration, a larger transmitting antenna will accommodate some variation in the offset d while maintaining link integrity. For reasonably sized devices, the antennas could accommodate variations in d of 1-5 cm and variations in θ of 45 degrees. The use of an array of antennas (e.g. antennas of the external device or implantable device) can further reduce the sensitivity to these parameters, allowing for even larger variations. If the implant falls outside of the acceptable range, it can alert the user that an adjustment is necessary. In some embodiments, the user can be notified (e.g. via a feedback element) that an adjustment is desirable via visual feedback (e.g. via an LED or other light), sound feedback (e.g. via a buzzer), tactile feedback (e.g. via a haptic transducer), or modified stimulation (e.g. stimulation configured to cause paresthesia). In general, the performance will degrade as h increases, and the h required for an application will determine the external transmitter power required to operate the system.

To assist in desirably aligning the external antenna 136 of the external device 130 with the implanted device 110 a variety of alignment aids can be used. In some embodiments, the alignment aid comprises a positioning device 600 that is affixed temporarily or permanently to the exterior of the patient's body BD, such as to the skin. It may be appreciated that in each of these embodiments, the positioning device 600 may optionally send electronic signals to the external device 130 indicating that the antenna 136 is desirably aligned and that stimulation should commence. Further, in some instances, the positioning device 600 is also used to verify that desired alignment is maintained over time. For example, the positioning device 600 electronically signals to the external device 130 to enable a power down feature or an alarm feature when the positioning device is not in proper use thereby indicating misalignment.

Figure 22:
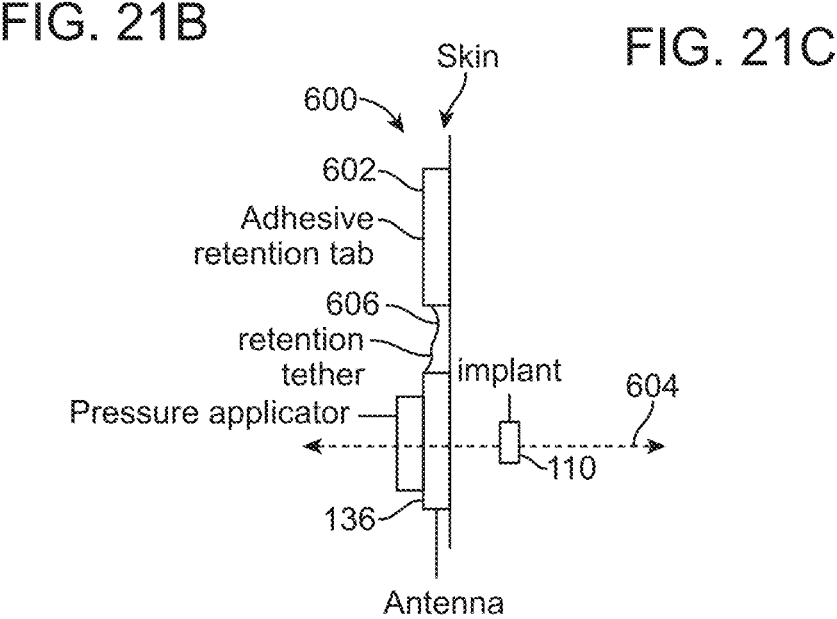
FIG. 22 illustrates an embodiment of a positioning device comprising a retention tab that is affixed to the skin near the implanted device.

FIG. 22 illustrates an embodiment of a positioning device 600 comprising a retention tab 602 that is affixed to the skin near the implantable device 110. The tab 602 can be affixed with any suitable adhesive, such as an adhesive gel, tape or film. The adhesive may be single-use and disposable, such as the type contained on a Band-Aid®, or the adhesive may be multiple-use and used several times before disposal, such as the type found on 3M™ Kind Removal Silicone Tape which causes minimal epidermal cell stripping and less pain. Or, the adhesive may be reusable indefinitely, such as the type found on 3M™ Stick-to-Skin Wearable Devices. To assist in the longevity of a positioning device 600 being affixed to the skin, the device 600 may be covered with a protective material, optionally a waterproof protective material, to protect the device 600 and its adhesive. An example protective material includes Glad GripTex™ seal-wrap. Referring back to FIG. 22, the tab 602 is affixed to the skin so that attachment of the external antenna 136 to the tab 602 desirably aligns the antenna 136 with the implantable device 110. As depicted, the central axis 604 of the antenna 136 is coaxially aligned with the implantable device 110. In this embodiment, the antenna 136 is attached to the tab 602 by a retention tether 606. The retention tether 606 may attach to the tab 602 by a variety of mechanisms, such as a hook, latch, knot, magnet, electrostatics, Velcro® tape, or adhesive, to name a few. In addition, the antenna 136 may further be held in place by a pressure applicator, such as a body covering 300. In addition, the pressure applicator may comprise a sterile bandage that may include an integrated or underlying antenna that can be applied over an implant incision site to allow therapy immediately following surgery.

Figure 23A:
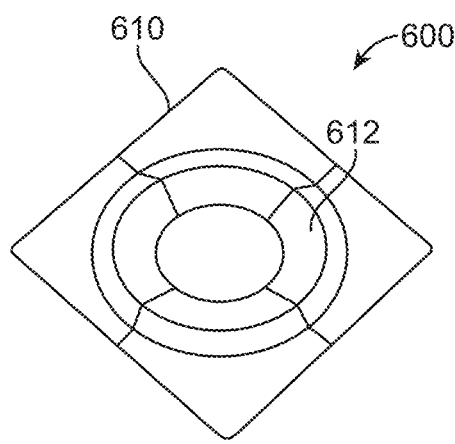
FIGS. 23A-23B illustrate another embodiment wherein the alignment aid comprises a positioning device that is affixed temporarily or permanently to the exterior of the patient's body, such as to the skin.
Figure 23B:
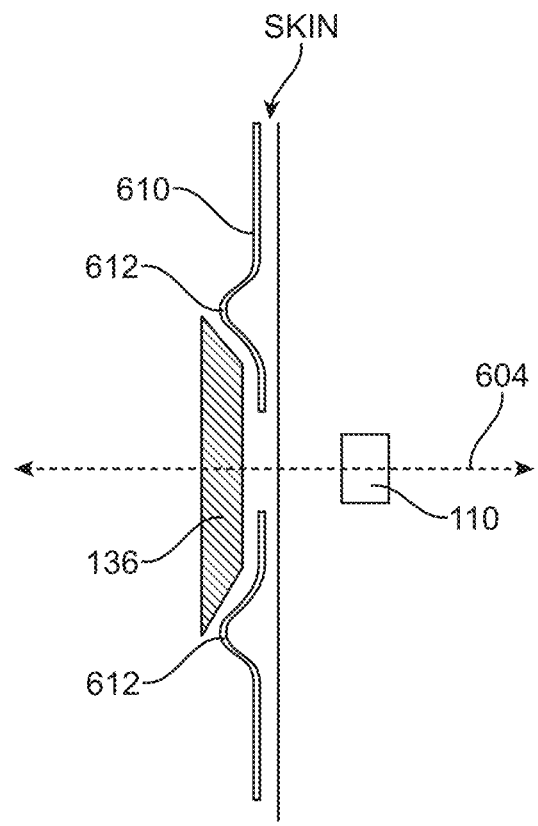

FIGS. 23A-23B illustrate another embodiment wherein the alignment aid comprises a positioning device 600 that is affixed temporarily or permanently to the exterior of the patient's body BD, such as to the skin. FIG. 23A illustrates an embodiment of a positioning device 600 comprising a shaped wafer 610, such as a colostomy wafer. The wafer 610 is shaped so as to be mateable with the antenna 136. In this embodiment, the wafer 610 has a ring shaped portion delineated by raised edges 612 (e.g. for guiding placement of the antenna). The wafer 610 can be affixed to the skin with any suitable adhesive, such as an adhesive gel, tape or film. The adhesive may be single-use and disposable, such as the type contained on a Band-Aid®, or the adhesive may be multiple-use and used several times before disposal, such as the type found on 3M™ Kind Removal Silicone Tape which causes minimal epidermal cell stripping and less pain. Or, the adhesive may be reusable indefinitely, such as the type found on 3M™ Stick-to-Skin Wearable Devices. To assist in the longevity of a positioning device 600 being affixed to the skin, the device 600 may be covered with a protective material, optionally a waterproof protective material, to protect the device 600 and its adhesive. An example protective material includes Glad GripTex™ seal-wrap. Referring to FIG. 23B, the wafer 610 is affixed to the skin so that attachment of the external antenna 136 to the wafer 610 desirably aligns the antenna 136 with the implantable device 110. The raised edges 612 of the wafer 610 guide the placement of the antenna 136 within the ring shaped portion so it is desirably aligned for communication with the implantable device 110. In this embodiment, mating occurs over the site of the implantable device 110 due to the shape of the wafer 610. Thus, as illustrated, when the antenna 136 is desirably attached, the central axis 604 of the antenna 136 is coaxially aligned with the implantable device 110. The antenna 136 may attach to the wafer 610 adhesively, by mechanical latches, by slots or by magnets to name a few mechanisms.

Figure 24A:
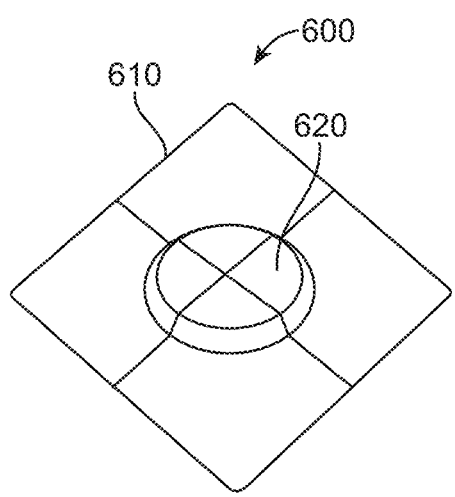
FIGS. 24A-24B illustrate an embodiment of a positioning device comprising a shaped wafer.
Figure 24B:
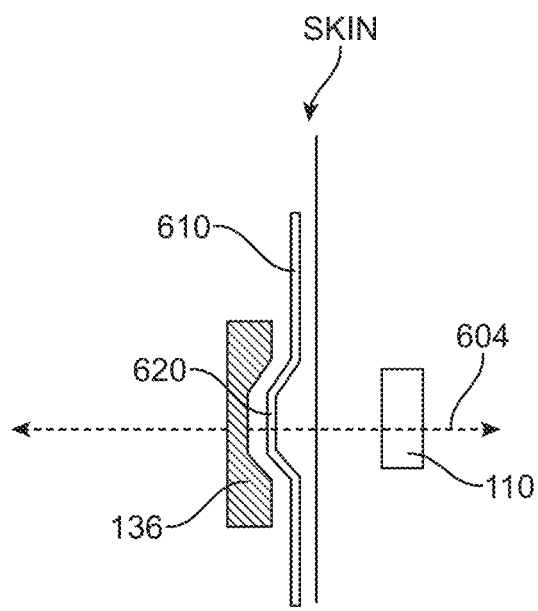

FIGS. 24A-24B illustrate another embodiment of a positioning device 600 comprising a shaped wafer 610. Again, the wafer 610 is shaped so as to be mateable with an antenna 136. In this embodiment, the wafer 610 has a raised disc shaped portion 620 (e.g. over which an antenna is placed). The wafer 610 can be affixed to the skin with any suitable adhesive, such as an adhesive gel, tape or film. The adhesive may be single-use and disposable, such as the type contained on a Band-Aid®, or the adhesive may be multiple-use and used several times before disposal, such as the type found on 3M™ Kind Removal Silicone Tape which causes minimal epidermal cell stripping and less pain. Or, the adhesive may be reusable indefinitely, such as the type found on 3M™ Stick-to-Skin Wearable Devices. To assist in the longevity of a positioning device 600 being affixed to the skin, the device 600 may be covered with a protective material, optionally a waterproof protective material, to protect the device 600 and its adhesive. An example protective material includes Glad GripTex™ seal-wrap. Referring to FIG. 24B, the wafer 610 is affixed to the skin so that attachment of the external antenna 136 to the wafer 610 desirably aligns the antenna 136 with the implantable device 110. The raised disc shaped portion 620 of the wafer 610 guides the placement of the antenna 136 over the disc shaped portion 620 so it is desirably aligned for communication with the implantable device 110. In this embodiment, mating occurs over the site of the implantable device 110 due to the shape of the wafer 610. Thus, as illustrated, when the antenna 136 is desirably attached, the central axis 604 of the antenna 136 is coaxially aligned with the implantable device 110.

Figure 25:
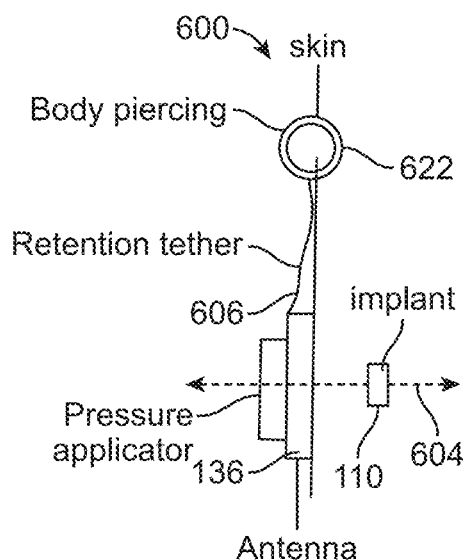
FIG. 25 illustrates a positioning device comprising a transcutaneous anchor, such as a body piercing, that is affixed to the skin near the implanted device.

FIG. 25 illustrates another embodiment of an alignment aid comprising a positioning device 600 that is affixed temporarily or permanently to the exterior of the patient's body BD, such as to the skin. Here, the FIG. 25 positioning device 600 comprises a transcutaneous anchor 622, such as a body piercing that is affixed to the skin near the implantable device 110. The anchor 622 is affixed to the skin so that attachment of the external antenna 136 to the anchor 622 desirably aligns the antenna 136 with the implantable device 110. In some embodiments, anchor 622 comprises suture (e.g. biodegradable suture) such as when anchor 622 is configured as a temporary anchor (e.g. in temporary trial use of system 100). As depicted, the central axis 604 of the antenna 136 is coaxially aligned with the implantable device 110. In this embodiment, the antenna 136 is attached to the anchor 622 by a retention tether 606. The retention tether 606 may attach to the anchor 622 by a variety of mechanisms, such as a hook, latch, knot, magnet, electrostatics, Velcro® tape, or adhesive, to name a few. In addition, the antenna 136 may be further held in place by a pressure applicator, such as a body covering 300.

Figure 26:
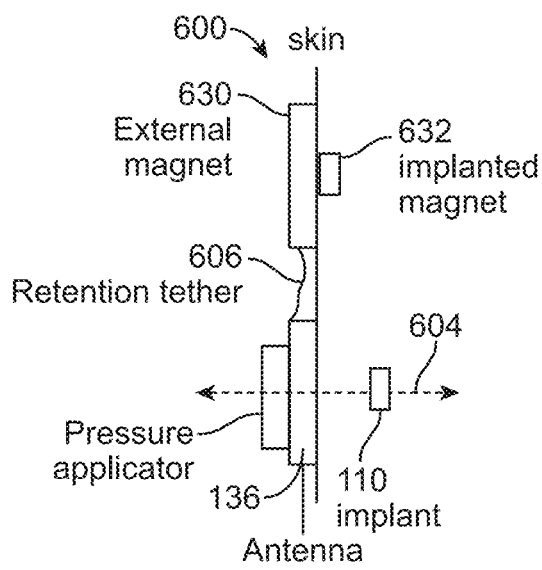
FIG. 26 illustrates an embodiment wherein the positioning device comprises a retention tab and a separate internally implantable magnet.

In other embodiments, some (e.g. one or more portions) or all of the positioning device 600 is implanted within the patient's body, such as under the skin to aid in aligning the external device 130. For example, FIG. 26 illustrates an embodiment wherein the positioning device 600 comprises a retention tab 630 and a separate internally implantable magnet 632. The retention tab 630 is comprised of or includes a magnet or a magnetically polarizable material. The implantable magnet 632 is implanted on, in (e.g. in an overmold) and/or near the implantable device 110 so that when the retention tab 630 is positioned over the skin covering the implanted magnet 632, the retention tab 630 can be used to desirably align the antenna 136. The retention tab 630 is held in place by magnetic force between the retention tab 630 and the implanted magnet 632. In this embodiment, the antenna 136 is attached to the retention tab 630 by a retention tether 606. The retention tether 606 may attach to the retention tab 630 by a variety of mechanisms, such as a hook, latch, knot, magnet, electrostatics, Velcro® tape, or adhesive, to name a few. As depicted, when the antenna 136 is desirably attached, the central axis 604 of the antenna 136 is coaxially aligned with the implantable device 110.

Figure 27:
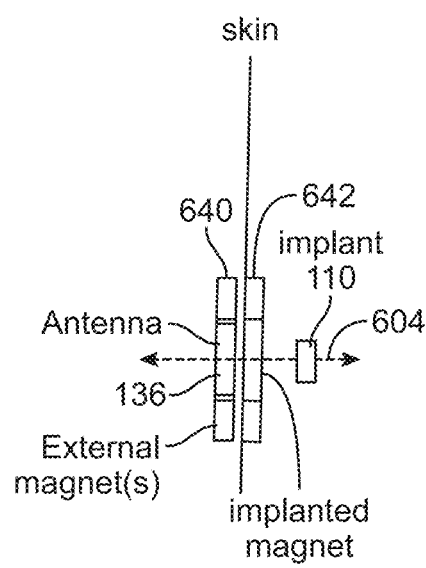
FIG. 27 illustrates an embodiment wherein the positioning device comprises a magnet mounted on the antenna and a separate internally implantable magnet.

FIG. 27 illustrates an embodiment wherein the positioning device 600 comprises a magnet 640 mounted on the antenna 136 and a separate internally implantable magnet 642. In this embodiment, the magnet 640 comprises a disc surrounding the antenna 136. The magnet 640 mates with a similarly shaped magnet 642 implanted beneath the skin. Due to the arrangement of the magnets 640, 642, mating occurs at the site of the implantable device 110. Thus, as illustrated, when the antenna 136 is desirably attached, the central axis 604 of the antenna 136 is coaxially aligned with both the internally implanted magnet 642 and the implantable device 110.

Figure 28A:
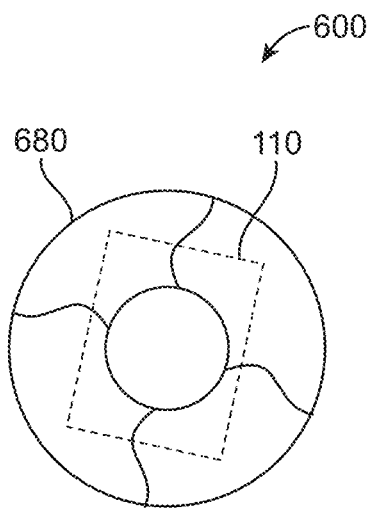
FIGS. 28A-28B illustrate an embodiment wherein the entire positioning device is implanted within the patient's body, such as subcutaneously, to aid in aligning the external device.
Figure 28B:
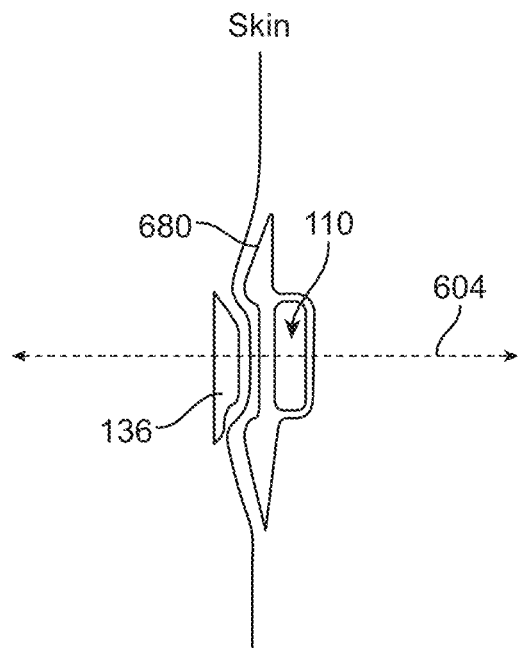

FIGS. 28A-28B illustrate an embodiment wherein the entire positioning device 600 is implanted within the patient's body, such as subcutaneously, to aid in aligning the external device 130. Such implanted positioning devices are typically comprised of soft passive materials and are implanted subcutaneously so as to be palpated by a patient or clinician to identify location and/or orientation of the implantable device 110. For example, FIG. 28A illustrates an embodiment wherein the positioning device 600 comprises a locating element, implantable guide 680, having a ring shape (as shown), and/or a cavity or dome geometry. The guide 680 may be comprised of any suitable implantable material, such silicone. In this embodiment, the guide 680 is attached to the implantable device 110, however it may be separately implanted. When the implantable device 110 is implanted beneath the skin, the guide 680 can be felt through the skin, indicating the location of the implantable device 110. The shape of the guide 680 assists in placement of the antenna 136 thereagainst, ensuring desired alignment, spacing and rotational orientation. In this embodiment, the guide 680 has a ring shape so as to mate with a ringed shaped portion of the antenna 136. The antenna 136 can be affixed to the skin with the use of an adhesive or other joining material. Alternatively, the antenna 136 can be held against the skin with the use of a body covering 300. As depicted, when the antenna 136 is desirably attached, the central axis 604 of the antenna 136 is coaxially aligned with the implantable device 110 for desired communication with the implantable device 110.

Figure 29A:
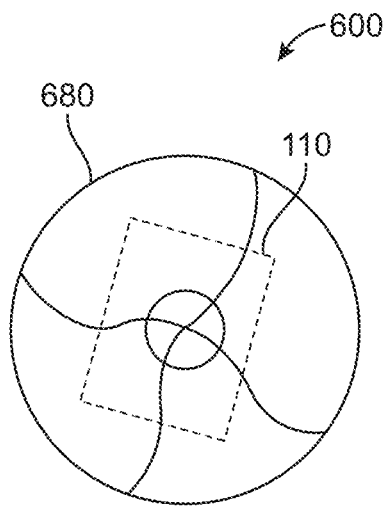
FIGS. 29A-29B illustrate another embodiment of an implantable guide.
Figure 29B:
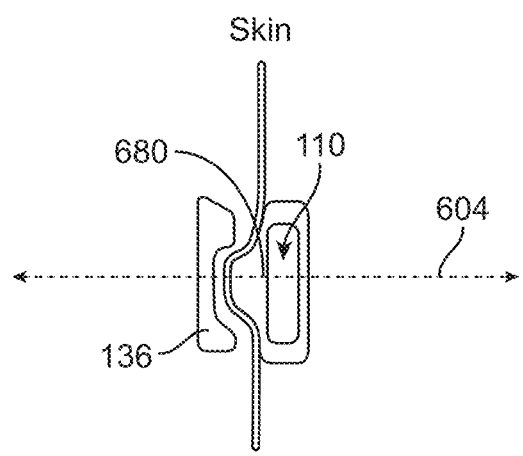

FIGS. 29A-29B illustrate another embodiment of an implantable guide 680. Here the implantable guide 680 has a dome shape. Again, the guide 680 may be comprised of any suitable implantable material, such silicone. In this embodiment, the guide 680 is attached to the implantable device 110. When the implantable device 110 is implanted beneath the skin, the guide 680 can be felt through the skin, indicating the location of the implantable device 110. The shape of the guide 680 assists in placement of the antenna 136 thereagainst ensuring desired alignment, spacing and rotational orientation. In this embodiment, the guide 680 has a dome shape so as to mate with an indented portion of an antenna 136. The antenna 136 is affixed to the skin with the use of an adhesive or other joining material. Alternatively, the antenna 136 can be held against the skin with the use of a body covering 300. As depicted, when the antenna 136 is desirably attached, the central axis 604 of the antenna 136 is coaxially aligned with the implantable device 110 for desired communication with the implantable device 110.

As mentioned, in some embodiments one or more devices, such as an antenna 136 and/or positioning device 600, are affixed to the skin. To reduce risk of adhesive induced skin irritation, a skin-attached component may be attached to a first skin location for a first time period, and at a second skin location for a second time period. In some embodiments, an adhesive coupling mechanism between the device and the skin may be used. The adhesive coupling mechanism allows the site of adhesive contact with the skin to be exposed, used, discarded and replaced or changed on a periodic basis to relieve skin previously exposed while adhering to a new skin site not previously exposed. Such a mechanism may be by way of sacrificial adhesive interposers that interlock to the external device, individual adhesive site tabs (e.g. like ECG contacts), a fixed set of adhesive sites, a rotating housing that exposes preassembled adhesive sites or accepts adhesive buttons along with means to maintain orientation can lead to distributing the potentially sensitive application of prolonged use skin adhesives.

Figure 30A:
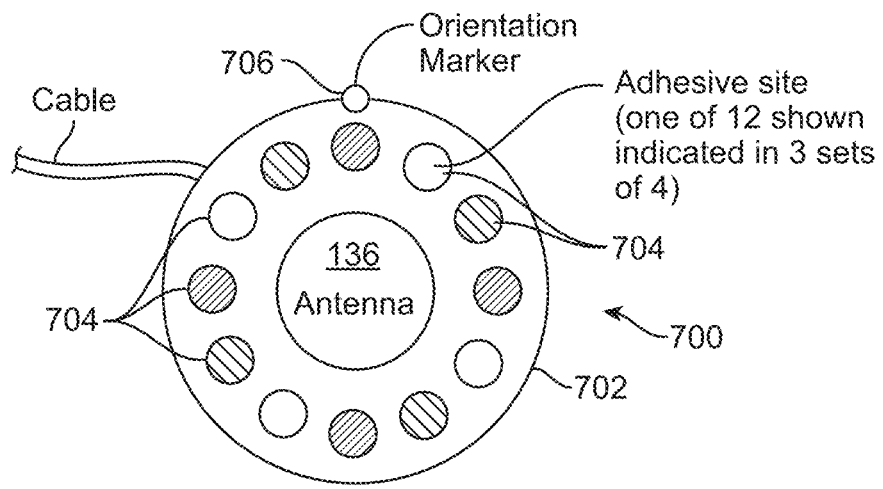
FIGS. 30A-30B illustrate an embodiment of an adhesive coupling mechanism comprising a planar element having a series of adhesive sites thereon.
Figure 30B:
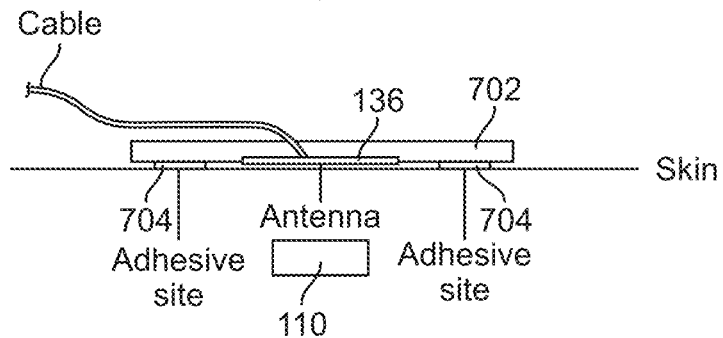

FIGS. 30A-30B illustrate an embodiment of an adhesive coupling mechanism 700. In this embodiment, the coupling mechanism 700 comprises a planar element 702 having a series of adhesive sites 704 thereon. The element 702 is sized and shaped to mate with the antenna 136 and the skin of the patient (or surface to which the antenna is to be adhered). In this embodiment, the element 702 has a ring shape wherein the center opening of the ring is configured to mate with the antenna 136. To adhere the element 702 and antenna 136 to the skin, one or more adhesive sites 704 are revealed, such as by removing a cover to expose an adhesive layer. Referring to FIG. 30A, each of the black shaded adhesive sites 704 may be revealed at a given time so as to balance the adhesion around the antenna 136. The planar element 702 is then pressed against the skin, as illustrated in FIG. 30B, holding the antenna 136 therebetween. In some embodiments, the element 702 includes an orientation marker 706 to assist in desirably orienting the element 702 and antenna 136 in relation to the implantable device 110. After a period of time has passed, the planar element 702 is adjusted to reduce the risk of adhesive induced skin irritation. In this embodiment, the previously exposed adhesive sites 704 are covered and new adhesive sites 704 are revealed. Referring back to FIG. 30A, the striped adhesive sites would now be revealed. The planar element 702 is again pressed against the skin, holding the antenna 136 therebetween. However, now, new areas of skin are exposed to the adhesive and the previous areas are able to rest. The orientation marker 706 can be used to maintain the original orientation of the element 702 to ensure that new areas of skin are being used for adhesion.

Figure 31:
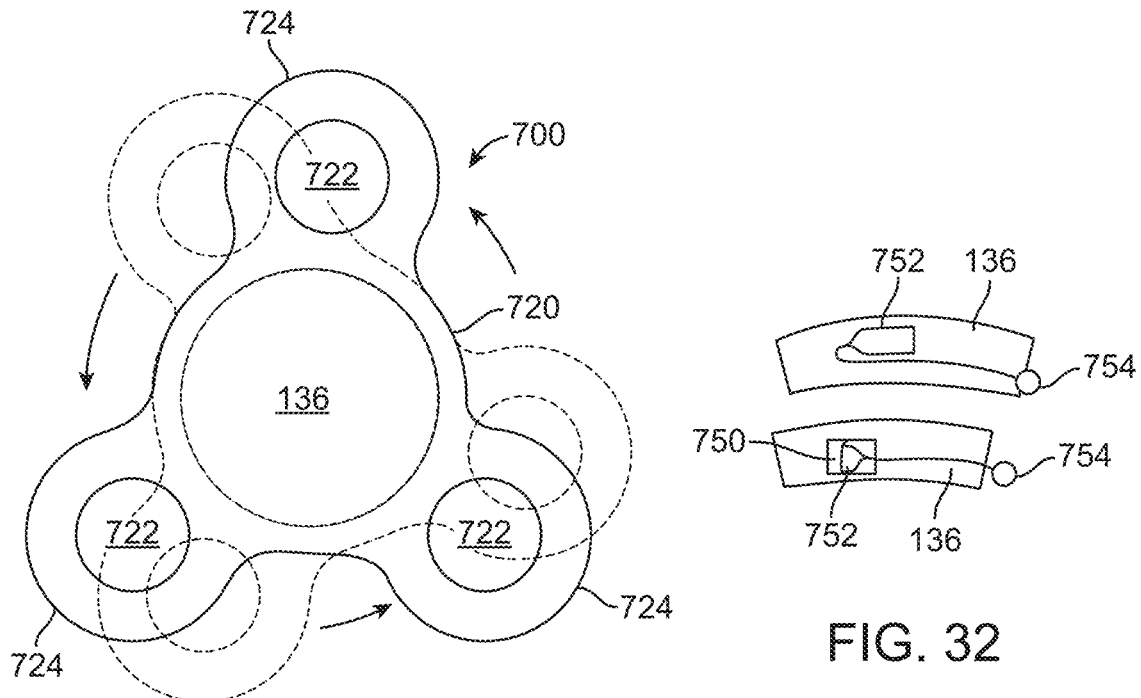
FIG. 31 illustrates an embodiment of an adhesive coupling mechanism wherein the coupling mechanism comprises a keyed element having a series of adhesive sites thereon.

FIG. 31 illustrates another embodiment of an adhesive coupling mechanism 700. In this embodiment, the coupling mechanism 700 comprises a keyed, planar element 720 having a series of adhesive sites 722 thereon. The element 702 is sized and shaped to mate with the antenna 136 and the skin of the patient (or surface to which the antenna is to be adhered). In this embodiment, the element 720 has a center opening configured to mate with the antenna 136 and three lobes 724 disposed around the center opening. Each lobe 724 has an adhesive site 722. To adhere the element 720 and antenna 136 to the skin, one or more adhesive sites 722 are revealed, such as by removing a cover to expose an adhesive layer. The element 720 is then pressed against the skin, holding the antenna 136 therebetween. After a period of time has passed, the element 720 is adjusted to reduce the risk of adhesive induced skin irritation. In this embodiment, the element 720 is rotated, as indicated by dashed outline and arrows in FIG. 31, so that the lobes 724 are offset from their original position. The element 720 is again pressed against the skin, holding the antenna 136 therebetween. However, now, new areas of skin are exposed to the adhesive and the previous areas are able to rest. It may be appreciated that in other embodiments, the circumference of the antenna is an adhesive site wherein only portions are revealed, such as by removing a cover, over time.

Figure 32:
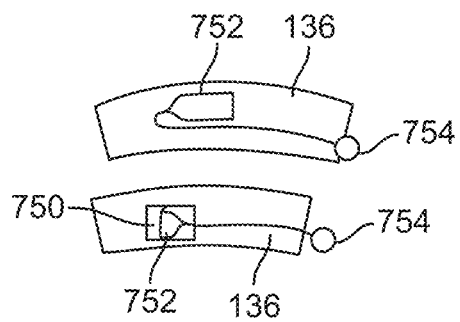
FIG. 32 illustrates an example device, such as an antenna, having an adhesive site and a cover.

It may be appreciated that in any of the above embodiments, an adhesive site can be covered while the external device is being desirably positioned. Once the external device is desirably aligned and positioned, the adhesive site can be revealed with the use of a tear-away adhesive strip. FIG. 32 illustrates an example device, such as an antenna 136 having an adhesive site 750 and a cover 752. A pull-cord 754 is attached to the cover 752. The pull-cord 754 allows the cover 752 to be removed (by pulling the pull-cord) without removing the antenna 136 from the surface to which it is being adhered. This maintains the desired alignment during the adhesive step.

In another embodiment, the alignment aid comprises one or more body markings such as by indelible ink or a tattoo applied to the skin. The body marking indicates the location of the implanted device or indicates the location on the skin at which a feature on the external system should be aligned to ensure that the antenna (elsewhere on the external system) is properly aligned relative to the implanted device.

Often, the alignment aids may be used in conjunction with body coverings 300. In some instances, the alignment aid is mounted on or built into the body covering. This may be particularly the case when the external antenna is mounted on or embedded into the body covering. In other instances, the alignment aid is separate from the body covering. This may be the case when the external antenna is tethered to the body covering, particularly when the alignment aid mates with or attaches to the tethered external antenna.

Figure 33A:
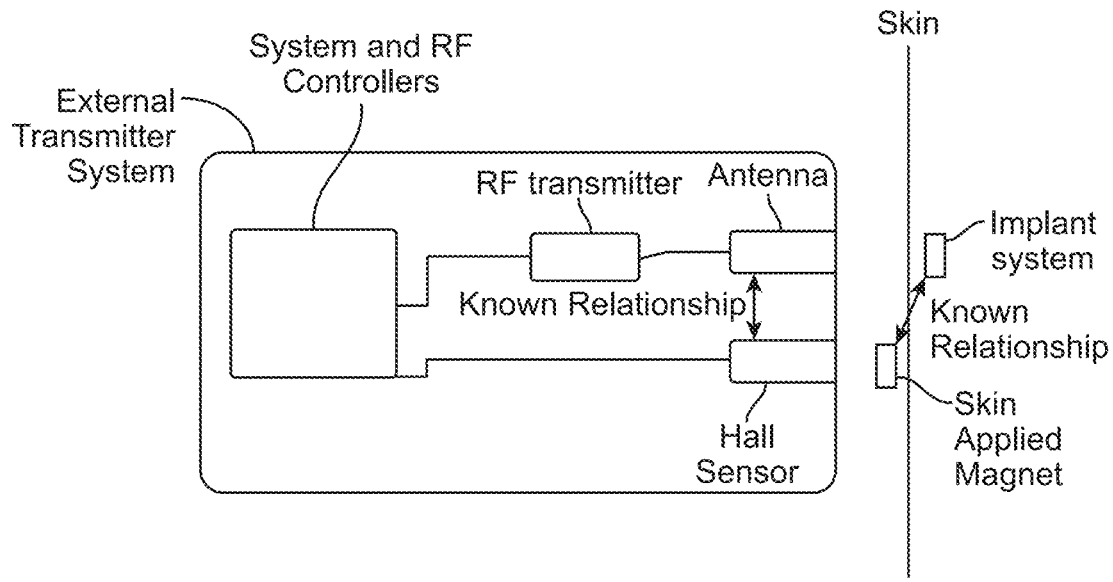
FIGS. 33A-33B illustrate scenarios wherein a positioning device can be used to locate the internally implanted device.
Figure 33B:
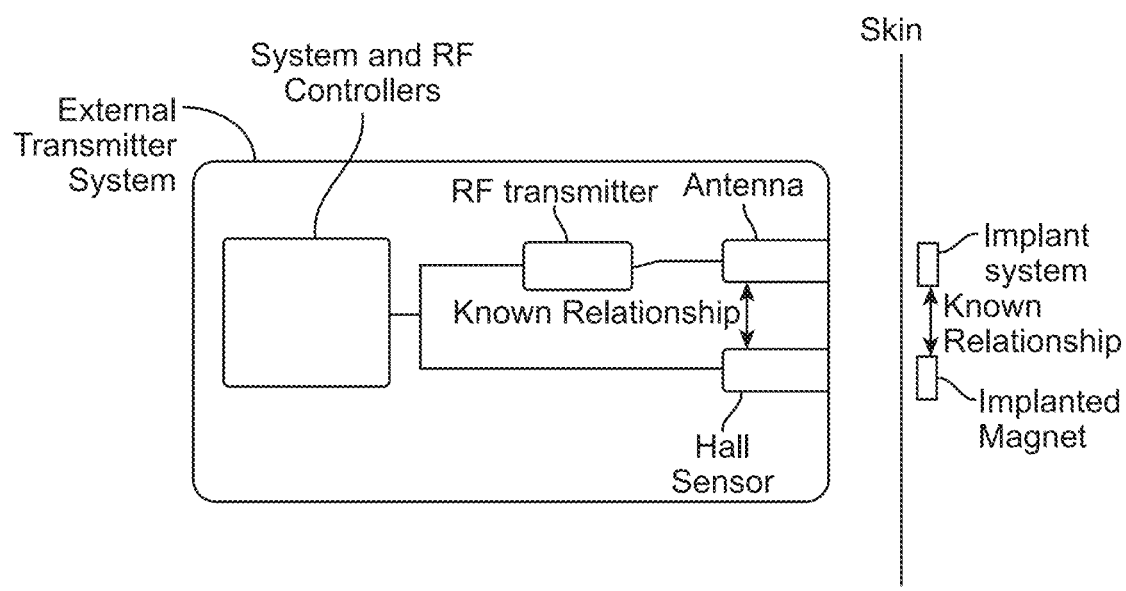

Referring to FIGS. 33A-33B, in all such scenarios wherein an implanted, semi-implanted or superficially applied element (such as a positioning device 600) can be used to locate the internally implantable device 110, the location of the implantable device 110 may be determined by electrical, magnetic (e.g. Hall, reed), mechanical, or other sensors and/or mechanisms external to the patient to determine the location of the implantable device 110. In some embodiments, power transfer parameters and/or coupling coefficients (Z-parameters, S-parameters, etc.) are used to determine the location of the implantable device 110 relative to the external system. These parameters can also include received power, RF signal strength, or supply voltage measurements made by the implanted system and communicated to the external system, through the data back channel. Alternatively or additionally, these parameters can be sensed by the external system by detecting changes in loading (that indicate received power of the internal system), mutual inductances, or backscattered electromagnetic fields. Such location or coupling information can thereby be used to ensure proper placement directly (e.g. engagement) or by informing the external system user where to place the transmitting antenna (e.g. guidance), or to inform the external system controller which antenna in an array to use for transmission to maximize the link (e.g. automatic selection), or to inform the external system controller which set of antenna in an array to activate in order to optimally steer energy towards the implanted system (e.g. dynamic optimization), or to adjust the amount of power transfer or other parameters associated with the link to ensure reliability, or simply to notify the user (e.g. tactile, acoustic, text message, email, visible, etc.) that adjustment is necessary and in what way to adjust the external assembly to improve link integrity via manipulations like up, down, right, left, rotation, pitch, roll, separation, etc. (e.g. user feedback).

Figure 34:
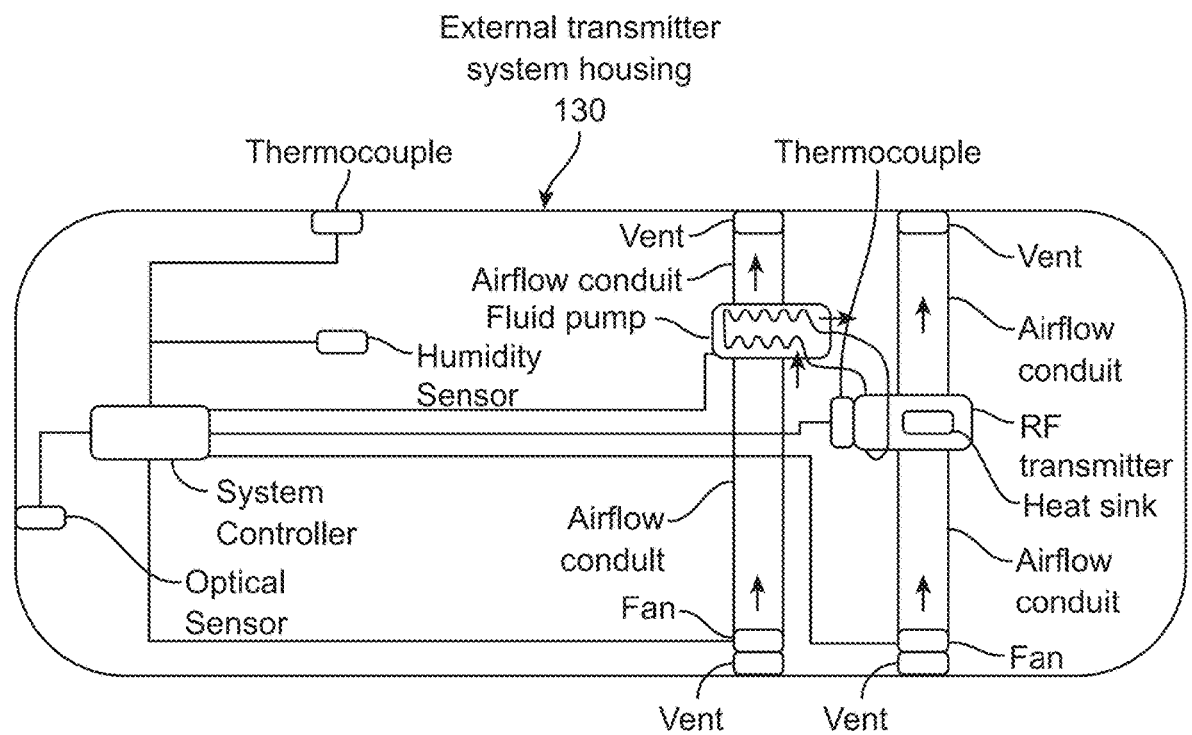
FIG. 34 illustrates a variety of thermal management elements provided in the component of the external device containing the transmitter.

Under certain circumstances, power requirements of the system 100 may be significant and demand notable power generation in the external transmitter which results in heat. As there are standards which pertain to the safe use of medical devices, the system controller is provided with sensors and controls which can be used to monitor or influence the environmental state of the system. Referring to FIG. 34, a variety of thermal management elements are provided in the component of the external device 130 containing the transmitter. Sensors may include thermal sensors, humidity sensors, optical sensors, microphones, etc. Controls to influence the environmental state may include fans, circulating fluid pumps, Peltier pumps, heat sinks, vents. Such controls may be actuated automatically or manually.

Figure 35:
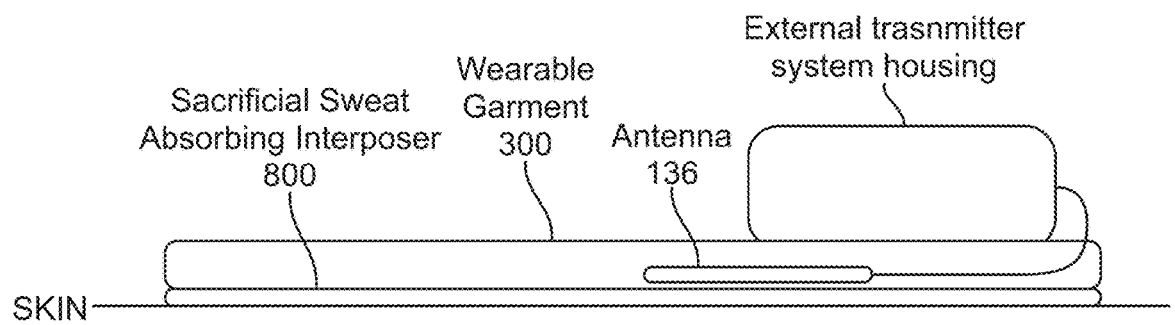
FIG. 35 illustrates an external device equipped with mechanisms to displace or eliminate sweat.

In addition to external environmental (e.g. humidity) or internal environmental (e.g. self-heating) factors, sweat from a patient can be present to varying degrees. Referring to FIG. 35, the external device 130 may be equipped with mechanisms to displace (e.g. airflow channels connected to a fan) and/or eliminate or at least reduce (e.g. sacrificial absorbent materials 800 between the transmitter and the patient's skin that are designed to wick sweat away) sweat. Such sacrificial absorbent materials 800 could be single use or washable, reconditionable or multi-use.

It may be appreciated that in some embodiments the body covering 300 is neither adhered to the body nor worn on the body like a garment or brace. In these embodiments, the body covering 300 has the form of an accessory and is positionable against the patient's body for a short period of time and then removed, such as for acute treatment or for special uses. Thus, the accessory temporarily covers a portion of the body having the implantable device 110 therein, so as to provide neuromodulation therapy for a prescribed period of time. This may be desired for treatments that only require short term periodic application of stimulation.

FIG. 36 illustrates an embodiment of a body covering 300 accessory having the form of a pillow, cushion or pad 900. The pad 900 houses the external device 130, including at least the antenna 136, for communication with the implantable device 110 within the patient's body BD. In this embodiment, the pad 900 includes a power cord 902 for plugging into a conventional outlet. However, it may be appreciated that the pad 900 may include a power supply, such as a battery, so as to be cordless. Typically, the pad 900 is comprised of a soft, pliable material within which the external device 130 is located in a manner so as to be undetected or comfortable for the patient to rest a body part against. FIG. 36 illustrates a patient's foot having an implantable device 110, wherein the foot is resting on such a pad 900. The pad 900 is configured so as to align the antenna 136 with the implantable device 110 for desirable communication. Thus, the patient receives an acute dose of therapy while resting upon the pad 900. In other embodiments, the patient rests their head against a similar pad 900 for treatment, such as for treating migraines, cluster headaches, or other acute treatments.

FIG. 37 illustrates another embodiment of a body covering 300 accessory having the form of a pillow, cushion or pad 950. In this embodiment, the pad 950 has the form of a lumbar support that is attachable to a chair 952. The pad 950 houses the external device 130, including at least the antenna 136, for communication with the implantable device 110 within the patient's body BD. In this embodiment, the pad 950 includes a power cord 954 for plugging into a conventional outlet. However, it may be appreciated that the pad 950 may include a power supply, such as a battery, so as to be cordless. Typically, the pad 950 is comprised of a soft, pliable material within which the external device 130 is located in a manner so as to be undetected or comfortable for the patient to rest a body part against. FIG. 36 illustrates a patient's back having an implantable device 110, wherein the back is resting against the pad 950. The pad 950 is configured so as to align the antenna 136 with the implantable device 110 for desirable communication. Thus, the patient receives an acute dose of therapy while resting against the pad 950. In other embodiments, the pad 950 may include a spring or other mechanism to provide some force in holding the pad 950 against the appropriate portion of the patient's body.

FIG. 38 illustrates an embodiment of a body covering 300 accessory having the form of a therapeutic chair 980. Such a chair may have the form of an armchair, sofa, recliner, lounger, office chair, car seat or other type of chair. The chair 980 is typically upholstered with soft, pliable padding, within which the external device 130 is located in a manner so as to be undetected or comfortable for the patient to rest a body part against. For example, the embodiment of FIG. 38 has the antenna 136 disposed along the back of the chair 980 while the remainder of the external device 130, such as the transmitter, is located on the side of the chair or tethered to the chair. When a patient sits in the chair 980, the patient's back rests against the back of the chair, and thus the antenna 136. A patient having an implantable device 110 in their back would therefore align the implantable device 110 with the antenna 136 and receive an acute dose of therapy while resting in the chair 980. The chair 980 may also include guides to seat the patient appropriately in the chair 980 to optimize alignment of the antenna 136 with the implantable device 110. It may be appreciated that a therapeutic chair 980 may have one or more antennas in other areas of the chair to provide therapy to any part of the body in contact with the chair, including simultaneously.

Figure 39:
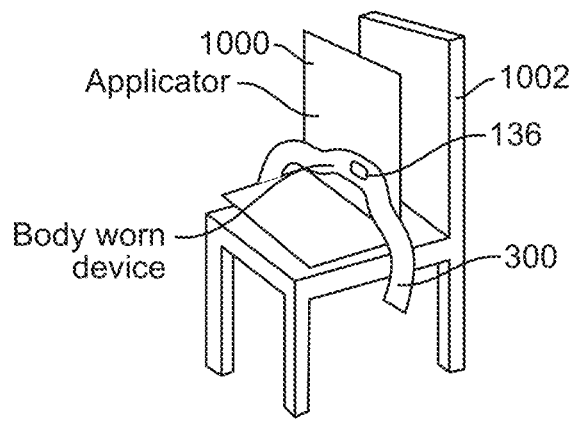
FIG. 39 illustrates an applicator that may be used in conjunction with a body covering, so as to assist in properly placing the body covering on the patient.

FIG. 39 illustrates an applicator 1000 that may be used in conjunction with a body covering 300, so as to assist in properly placing the body covering 300 on the patient. For example, desirably aligning a body covering 300 to communicate with an antenna disposed along a patient's back may be challenging for some patients. In this embodiment, the applicator 1000 is configured to be positioned on a chair 1002. The applicator 1000 includes features to pre-position the body covering 300 for optimal placement so that the patient need only sit down and lean against the applicator 1000 to desirably align the body covering 300 with an implantable device 110. The patient can then pull the belt straps around his/her body and latch the covering 300 to hold the covering in place.

Figure 40:
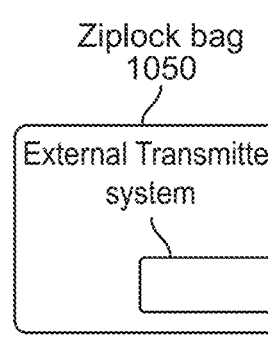
FIG. 40 illustrates an embodiment wherein the body covering is placed in a water resistant bag.
Figure 41:
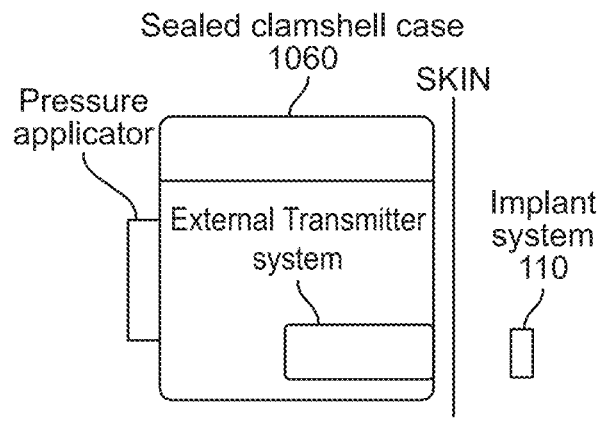
FIG. 41 illustrates an embodiment wherein a custom case is designed to house the external transmitter system during wet use cases.
Figure 42:
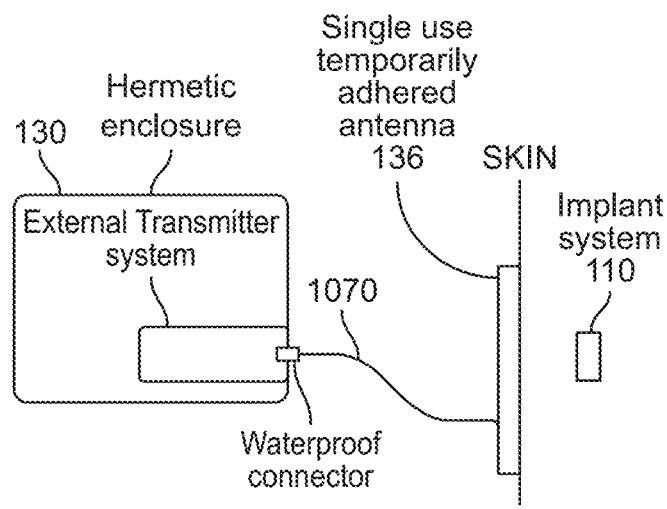
FIG. 42 illustrates an embodiment wherein an external device is hermetic and is designed to be interfaced, using a waterproof connector, to a single or multi-use temporary antenna.

To protect the body covering 300 or a body covering 300 accessory from the environment, such as wet environments, at least some of its components may be protected by a resistant layer. In some embodiments, the body covering 300, body covering 300 accessory or components thereof, are placed in a water resistant bag 1050, such as a plastic bag or Ziplock® bag or vacuum sealed bag, as illustrated in FIG. 40. In another embodiment, a custom case 1060 is designed to house the external transmitter system during wet use cases, as illustrated in FIG. 41. In another embodiment, illustrated in FIG. 42, an external device 130 may be produced that itself is hermetic and is designed to be interfaced, using a waterproof connector 1070, to a single or multi-use temporary antenna 136 (e.g. adhesively attached).

Power Supply Configurations

The external device can be powered through batteries or with direct connections to wall outlets. Batteries allow for portable systems and for most applications should operate for several days before requiring recharging. Some applications may be more power intensive and require more frequent recharging. A variety of battery options and power supply configurations are provided herein.

As mentioned, the system can operate from wall outlets when the patient is at home or in a place where this is convenient. The antenna 136 should be located in close proximity to the implantable device 110. Since the battery pack could significantly increase the size and weight of the external device 130, the ability to carry it in a different location could reduce patient discomfort. Thus, the power source can be located in a separate enclosure from the antenna 136 to increase the comfort of the overall system.

Figure 43:
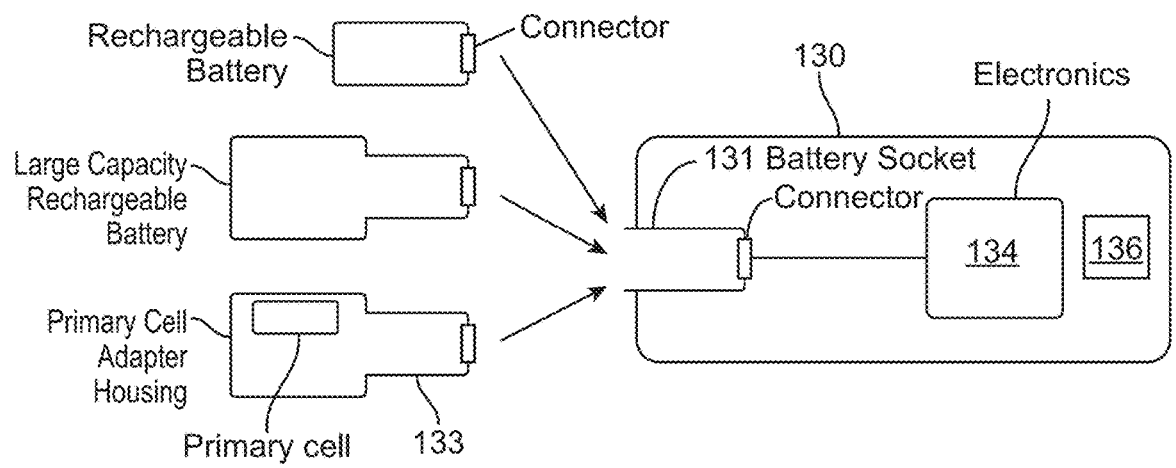
FIG. 43 illustrates an embodiment of an external device having battery socket that may receive a variety of rechargeable battery sizes.
Figure 44:
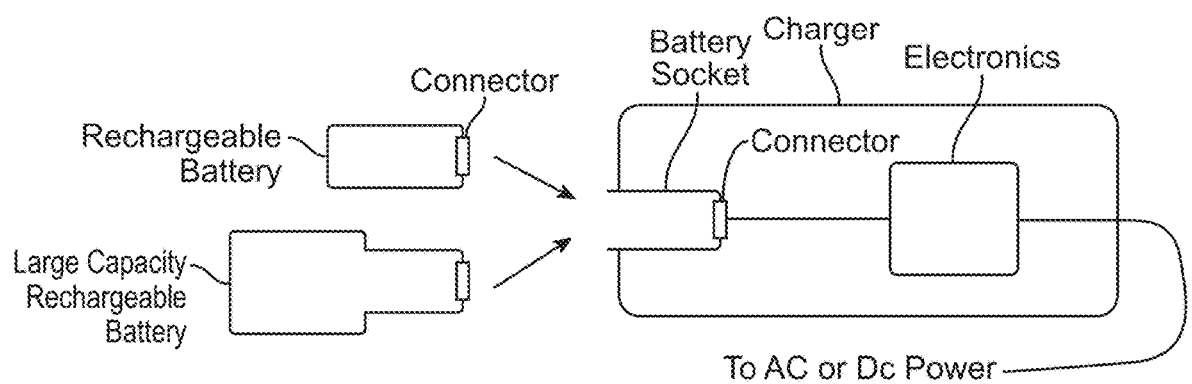
FIG. 44 illustrates an embodiment of a charger.

In an externally powered system, the user is able to replace the battery as needed. Commonly, such batteries may be rechargeable (e.g. Li-Ion, Li-Poly, NiMH, etc.) and may be removed from the external system and replaced with a fully charged battery while the discharged battery is then placed on a charger. FIG. 43 illustrates an embodiment of an external device 130 having a battery socket 131 that may operatively receive (e.g. electrically connect to) a variety (e.g. multiple different) battery sizes and/or types (e.g. rechargeable or otherwise). The battery size can be chosen to optimize battery life for a given patient against size of the external device 130. Alternatively, in the event that access to power to recharge a battery is not available, the socket 131 that accepts rechargeable batteries may also accept an adapter 133 equipped to accept primary cell batteries (e.g. AAA, AA, C, D, Zn-Air, etc.). In such cases, the socket 131 may be designed to require each battery type to present the same electrical interface (allowing the system to not be concerned with the type of connected battery), or it may also encode the type of the battery so that the system and RF controller modules can optimize the link for the given power source and monitor battery usage and remaining life so as to notify the user in a timely manner when the next battery change is required. FIG. 44 illustrates an embodiment of a charger.

Figure 45:
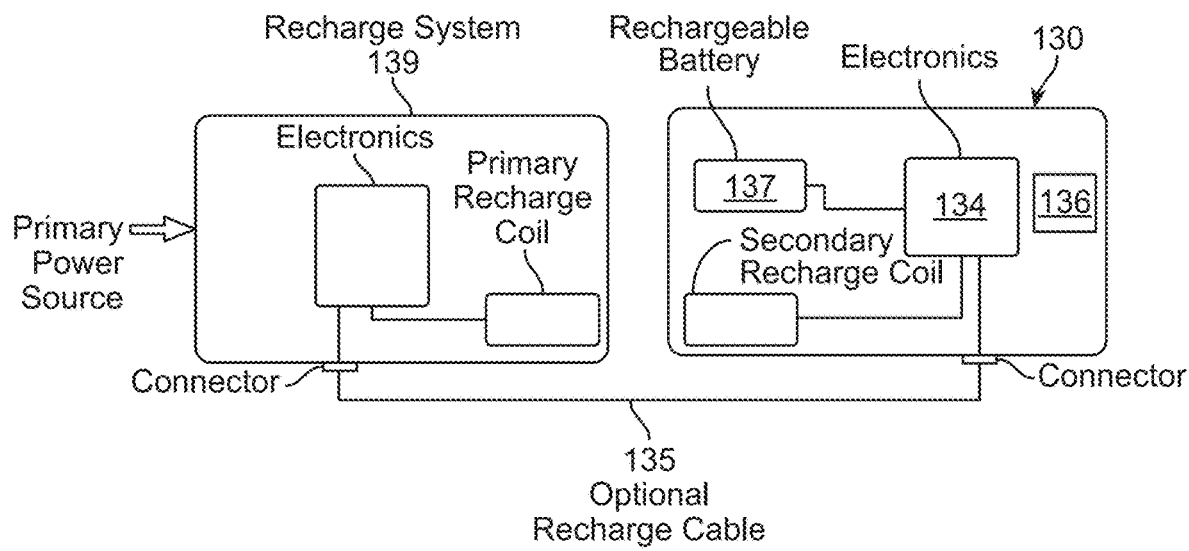
FIG. 45 illustrates an embodiment wherein a rechargeable battery is permanently installed in the external system.

Alternatively, in some embodiments, a rechargeable battery is permanently installed in the external device 130. An example of such an embodiment is illustrated in FIG. 45. Here, the entire external device 130 is removable for charging, or a cable 135 is connected to the external device 130 to recharge the integrated battery 137 from a separate external recharge system 139. Alternatively, a separate external system (e.g. a relatively small inductive charger configured to wirelessly transfer energy) may be brought into proximity of the external device 130 to recharge battery 137, or the external system may be brought into proximity of an inductive charger (e.g. a chair, a bed, or other large object similarly configured to wirelessly transfer energy) to similarly recharge battery 137. Alternatively, combinations of the above may be envisioned wherein a secondary accessory (e.g. an inductive receiver coil) is worn during sleep and directly or wirelessly connected to the normal external system or worn in place of the normal system and is responsible to harvest energy from a bedside or in-bed transmitter to charge or operate the system battery during sleep.

Figure 46:
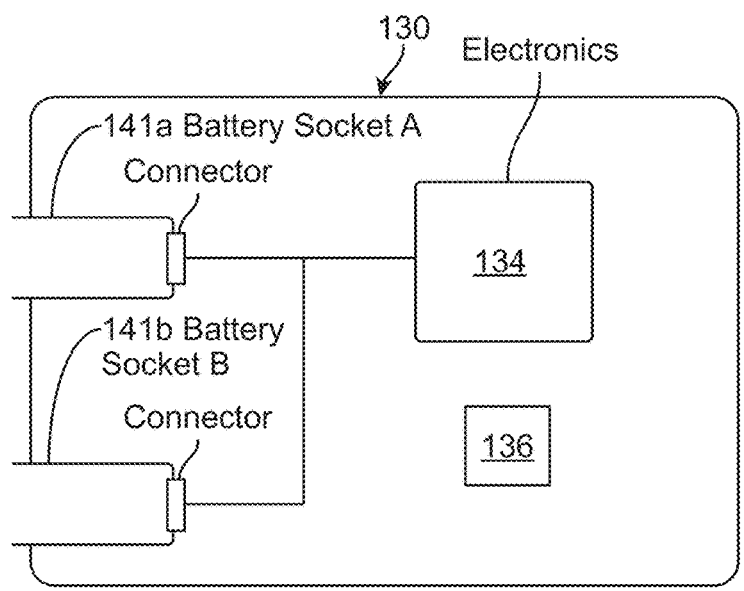
FIG. 46 illustrates an embodiment wherein two rechargeable battery sockets are integrated into the external device such that the presence of one or both charged batteries is sufficient to run the system.

Alternatively, as illustrated in FIG. 46, two rechargeable battery sockets 141a, 141b may be integrated into the external device 130 such that the presence of one or both charged batteries is sufficient to run the system. This mitigates stimulation stopping during battery swaps. In related embodiments, electrical, mechanical or electro-mechanical interlocks may be employed to ensure a replacement battery is present before the original battery can be removed so as to prevent interruption of therapy where possible. In other embodiments, interlocks may be employed to prevent a second battery from being connected or activated whenever an already connected battery is present and above an acceptable charge level. In other embodiments, the second battery socket may be populated by another compatible battery or accessory whereupon the second battery can charge the first battery or the first battery can charge the second battery or both batteries may be used in conjunction to deliver more power for therapy to the user. Alternatively, a USB connected, mains connected, automotive 12V connected, energy harvester connected, etc. power module may be coupled to a battery socket to operate the system, recharge the system or do both simultaneously.

In the above described embodiments and related similar extensions, means relying on electrical, mechanical or electro-mechanical interlocks to allow or prevent installation and removal of batteries, to allow or prevent charging of installed modules, or to allow or prevent simultaneous use are further designed to prevent locking out of the system (e.g. dead batteries with an inability to replace them) or to create any safety hazard (e.g. attempting to charge an installed primary battery module).

Figure 47:
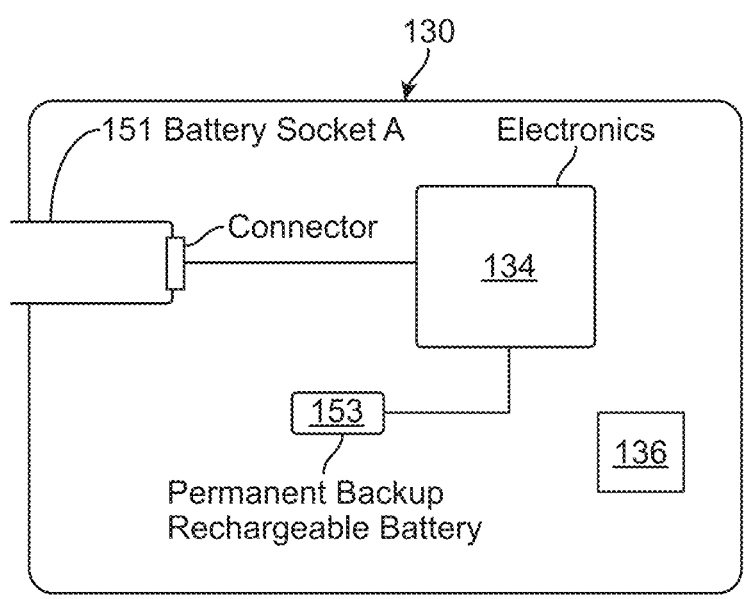
FIG. 47 illustrates an embodiment of a hybrid system, wherein a main battery socket is present but the system also includes a permanently integrated rechargeable power source.

In some embodiments, a hybrid system, an example of which is illustrated in FIG. 47, may be used wherein a main battery socket 151 (that may accept primary or rechargeable batteries of a known or unknown type) is present but the system also includes a permanently integrated rechargeable power source 153. In some embodiments, an integrated rechargeable power source may be a large capacity battery suitable for extended normal use operation. In other embodiments it may be a small rechargeable battery, a supercap or another less frequently replaced primary cell battery whose function is primarily to maintain system operation during periods of time when a main socketed battery has been removed to recharge and a new fully charged socketed battery is about to be installed. Such a momentary interruption time may be on the order of seconds to a minute and hence a reasonably sized cell can be envisioned to keep the system operational. In either event, once a new battery is installed, the system controller may ensure the permanently integrated battery is again charged so as to be ready to power the system during the next power outage due to socketed main battery removal. In some embodiments, this permanently integrated battery is the primary power source, and battery life can be extended with an additional battery connected to the battery socket. Such a system may be advantageous during periods of higher power therapy.

In any such multi-battery or multi-size battery scenario, utility of different configurations for different indications can be advantageous. For example, a low power stimulation therapy can be delivered with the system running in the smallest configuration whereas a high power stimulation therapy can be delivered with a larger battery or a dual battery configuration.

Antenna Arrays

As mentioned, the at least one external device is disposed outside of the patient body and is positioned in communication range with the implanted device. Appropriate positioning of the external device, particularly the external antenna, is critical for optimal communication. To assist in proper alignment of the external antenna with the implanted device, the external antenna or transmitter antenna may comprise an antenna array, an array of antennae actively used by the transmitter module and RF controller to enhance system performance.

Figure 48:
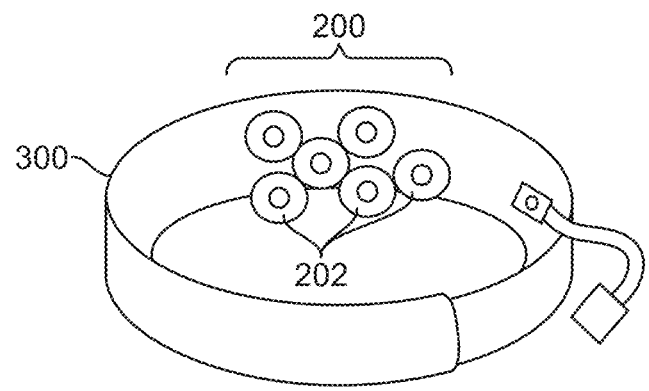
FIG. 48 illustrates an example embodiment of a body covering and an external device including an antenna array.

An example embodiment of a body covering 300 and an external device including an antenna array 200 is illustrated in FIG. 48. In this embodiment, the antenna array 200 is comprised of six antennae 202. Advantages may include reduced sensitivity to device or patient movement by allowing the system to select the optimal antenna 202 for communicating with and powering the implantable device 110. Antenna array 200 can be driven with independent transmitters per antenna 202, wherein one or many are activated as desired. Alternatively, a switch array may be employed to allow one or multiple transmitters to each deliver energy to one or multiple physical antennae 202 in isolation, in selected combinations, or in a time division multiplexed fashion.

In some embodiments, the switch array can play an integral role in the system performance. In the simplest instance, the switch matrix is responsible for directing all RF transmitter power to a selected antenna 202 under control of the RF controller. More complicated roles may include time or ratiometric multiplexing of RF power to two or more antennae, 202 including the possibility of a phase delay to one or more antenna 202, so as to enable the transmission of power towards the implantable device 110 from more than one antenna 202 simultaneously in order to optimize coupling to one or more implantable devices 110.

In other embodiments, the RF transmitter component may generate more than one output (same or different phase, same or different amplitude) and hence the switch matrix may become a many to many network, with requisite addition to overall system complexity. In other embodiments, the switch matrix is placed before power amplification, and directs signals with the desired magnitudes/phases to the proper RF transmission pathways.

In other embodiments, the switch array and means to connect one or multiple antennae to one or multiple RF transmitters can be achieved through electronics (e.g. integrated circuits) and use of smart antennae and cabling. A power and data bus, connecting an external transmitter module (ETM) and a multi-array antenna 200, is described wherein control data is sent over the RF power bus and used by the smart antenna to configure switches on the antenna array 200 thereby reducing the complexity and bulk of the cabling between the ETM and the antenna array 200. This has the advantage of reducing bulk of a cable connecting an ETM to a possible multitude of antenna.

It can be shown that power transfer insensitivity to lateral, rotational, or depth displacement of an implantable device 110 beneath an array of external transmitter can be improved by employing arrays with different drive configurations (e.g. phase, amplitude, and/or other transmission parameters). The optimal magnitudes and/or phases of each antenna 202 can be derived from coupling parameters or other measurements, such as the Z-parameter and/or S-parameter matrix, that describes the external antennas, the implant antennas, properties of the environment, or some combination of these. In some embodiments, the system is optimized to maximize power transfer efficiency, to minimize SAR, to minimize emissions, or some combination of these. The optimal point can be estimated from measurements, a lookup table, calculations, algorithms, weighted averages, or combinations of these. The Z-parameter or coupling matrix can be estimated from power transfer measurements, load modulation, antenna impedance measurements, or combinations of these.

In some embodiments, the transmitter can precisely control the magnitude and/or phase of the signals provided to each antenna 202. The system can deduce the proper drive signals by performing a scan and using a multi-dimensional gradient search technique to find the maximum. Alternatively or additionally, measurements of system data (such as those described above or information about power transfer, the relative position of the external and internal antennas, properties of the transmission medium, SAR, emissions, etc.) could be performed to estimate the proper drive signals, which can be accomplished through a calculation or from a lookup table. For example, the Z-parameter matrix could be estimated from a power transfer measurement, which could be used in an algorithm to calculate a drive configuration. In some embodiments, the algorithm involves solving a convex problem or an eigenvalue problem that relate voltage, current, and impedance matrices. In some embodiments, a fixed number of drive configurations are used, and the system can scan through all of them to select the configuration with the best performance, or it can use data to select the best configuration from a lookup table. The scanning and/or measurements can occur in real-time, at regular or irregular time intervals, on-demand, or combinations of these. In some embodiments, the scan and/or measurement is used to provide information about the location of the implant, which can be used to reposition the external antennas. The control of the drive configurations can be automated or it can involve some level of manual adjustment, either of which can update the configurations dynamically. In some embodiments, alternating through different drive configurations during operation can minimize SAR or external system heating. For example, by time division multiplexing among RF transmitters (idling some while one or others are active) local heating in the external can be spatially spread out to reduce maximum temperature rise of the system. Similarly, by sequencing through antenna, local energy delivery to regions of tissue directly beneath each antenna can be reduced thereby reducing measured SAR.

Figure 49:
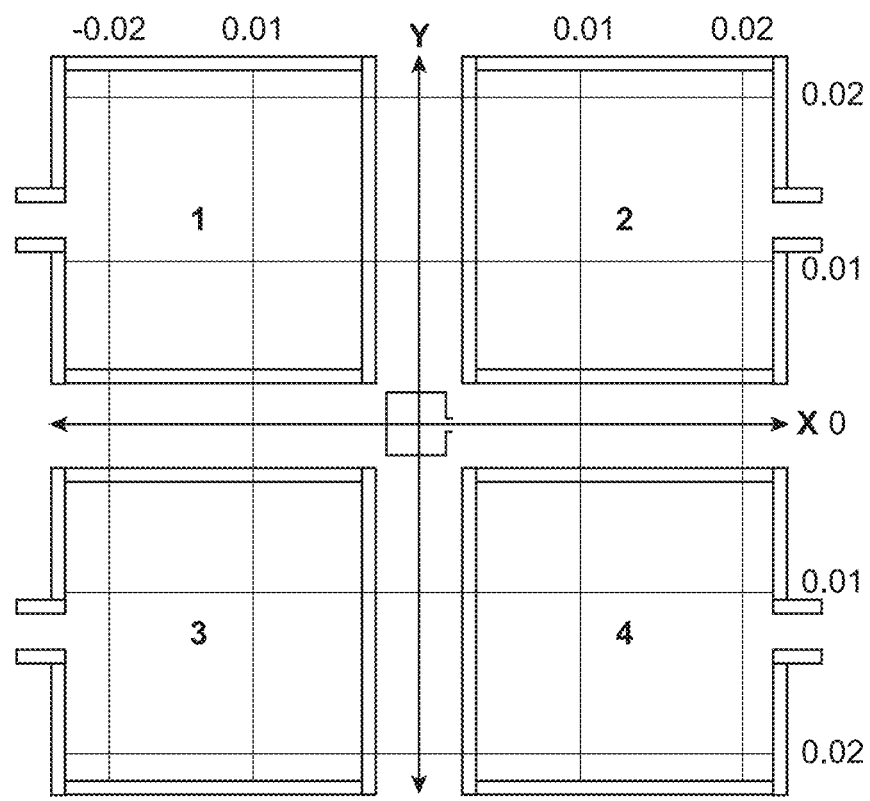
FIGS. 49-50 illustrate an example of an external antenna array in the configurations of 3, 4 or 5 loop antennae.
Figure 50:
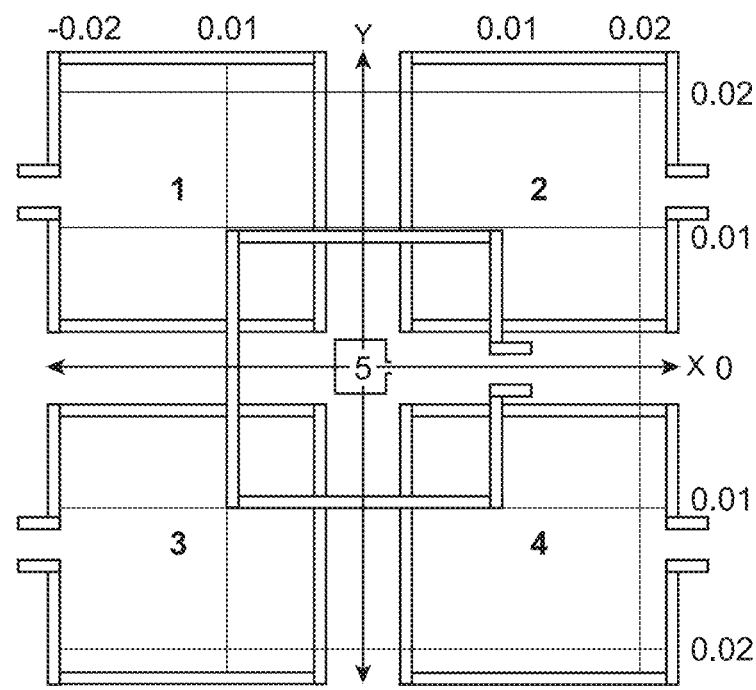
Figure 51:
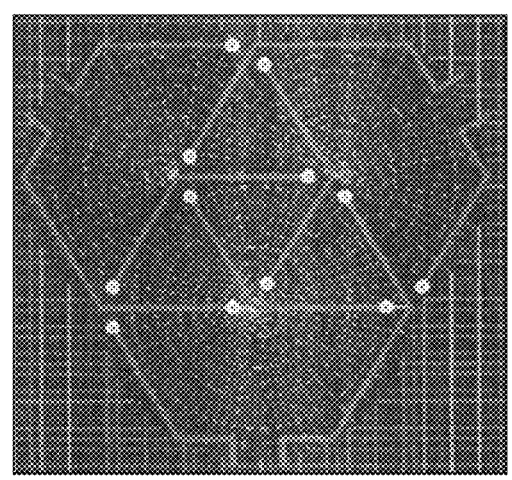
FIG. 51 illustrates a 3 antenna topography of a multi-antenna array.

Per techniques described herein, coupled with the implant receiver architecture, the external system can manage an array of external antennae communicating to one or more internal antennae. One example of an external antenna array is the configurations of 3, 4 or 5 loop antennae illustrated in FIGS. 49-50, which could be fabricated on a flexible substrate to conform to the body contours or built as flexible conductors woven into a fabric material, among other possible instantiations. Other numbers of loop, patch, slot, stub or spiral antennae (not an exhaustive list of possible antenna types) in overlapping or non-overlapping arrangements may also be envisioned. FIG. 51 illustrates a 3 antenna topography of a multi-antenna array. In any case, the implant antenna array may be a single planar loop antenna, a pair of planar loop antennae coupled to individual rectifiers, a pair of orthogonal loop antennae coupled to individual rectifiers, one loop and one dipole antenna, two antiparallel dipole antennae, two orthogonal dipole antennae, one dipole antenna, etc. Each such instantiation of the implant antenna topology will influence desirable attributes or necessary construction and arrangement of any viable external transmitter (e.g. number of external antennae, their optimal orientation, their relative placement, their size, their topology, etc.).

Additionally, elements of the antenna, matching network and requisite cabling may routinely find themselves in situations of use by patients wherein significant repetitive motion is presented to the assembly (e.g. walking). Techniques to stabilize assemblies and ensure robustness against mechanical fatigue and/or electrical detuning may include strain reliefs (loops, sheaths, zig zag placement, reels, overmolding), mechanical reinforcement (backings, frames, subassembly housings), redundancy (multiple antennae on a flexible circuit replicated top/bottom so as to create a detectable, albeit still functional, intermediate mode of operation in the event of a single point failure on one antenna).

To minimize sensitivity of an antenna to environmental detuning (e.g. sitting on a metal backed chair, swimming, etc. and even human touch, during repositioning) impedance matching structures built into the antenna array 200 may be fabricated to ensure the optimally matched impedance of the antenna is tuned by structure (e.g. backing materials) and further optimized for the state when the antenna is coupled to the patient. For example, a magnetic material can be used as a backing for the antenna, which allows for magnetic coupling while shielding electric fields. This reduces sensitivity to metallic materials that may be located behind the material during use. Alternatively or additionally, these matching networks can have elements that can be tuned dynamically, such as a variable capacitance. Such techniques, enable the automatic detection of states where the external system and the implant system are decoupled in which case the external system can notify the user and/or reduce power consumption as it searches for the implant at a reduced power via periodic checking. Such techniques also ensure reliable system operation as users go about their daily activities by minimizing the sensitivity of the link to normal and reasonable motion.

Figure 52:
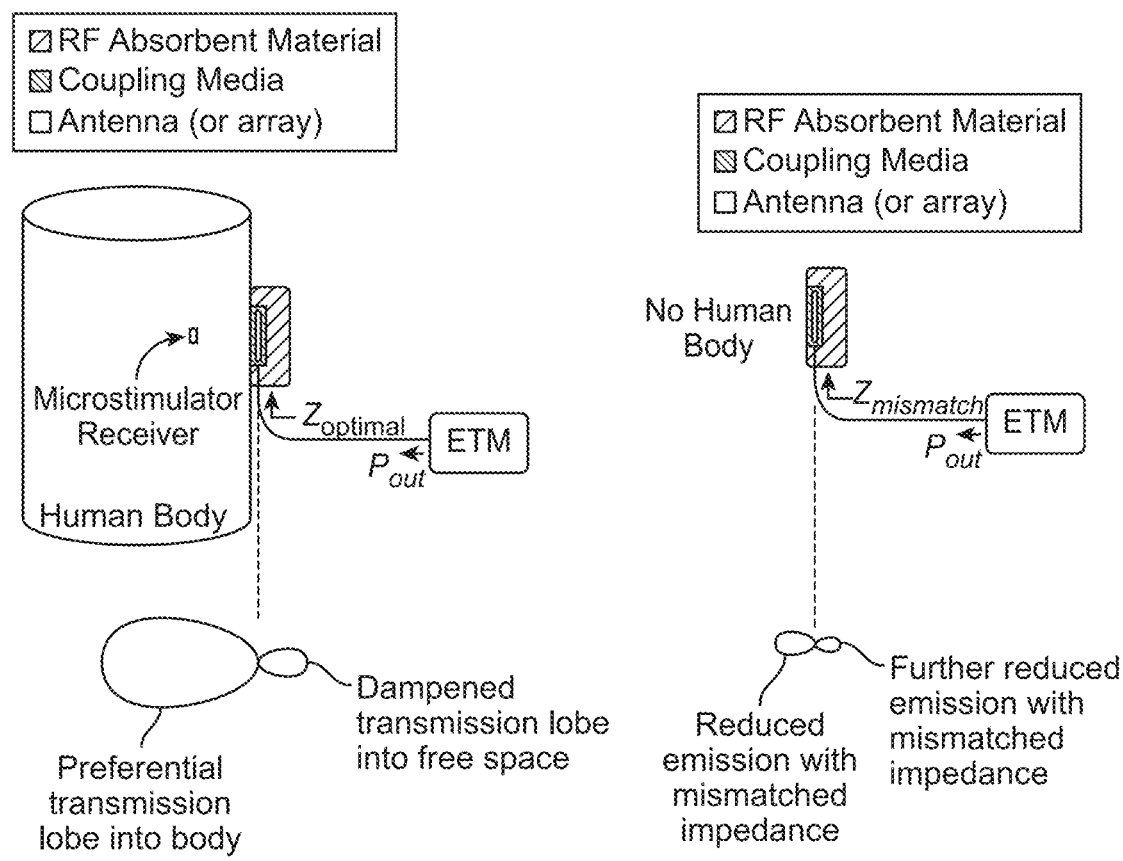
FIG. 52 depicts a coupled system with an antenna, coupled to a body with various matching and/or absorptive materials placed in the vicinity of the antenna.

Additionally, as the antenna are intended to radiate energy preferentially into the body and not into free space for reasons of regulatory compliance and power efficiency, techniques designed to improve the match of the transmitter plus antenna system to a patient are employed. FIG. 52 depicts a coupled system with an antenna, coupled to a body with various matching and/or absorptive materials placed in the vicinity of the antenna. In particular, as mentioned above, the magnetic material or an RF Absorbent Material would not only prevent the antenna from radiating into free space (away from the human body), but also shield the antenna from being de-tuned by contact or proximity to RF conductive materials, e.g. human touch, the back of a chair, and other conducting walls/surfaces/physical objects which can be envisioned to detune the antenna if an intervening RF shield or absorber was not present. Referring to FIG. 52, the external transmitter module or ETM comprises those part of the RF system that may be distinct from the antenna assembly.

The purpose of this structure is to maximize power delivery to the receiver implanted in the body and to minimize transmission into free space beyond the body. Such an approach introduces antenna gain (or loss) to the system defined as the difference between an isotropic radiator and an antenna under test. The goal is to shape coupling fields to be large into the human with a small amount of radiation into free space. Such techniques enable the delivery of suitably high levels of RF power efficiently to implanted receivers without exceeding stringent worldwide free space emission regulations. Additionally, the ETM can detect the presence of tissue based on information about the antenna tuning or implant coupling and shut off when not near tissue, saving power and mitigating electromagnetic emissions.

Techniques for absorbing RF radiation preferentially include lightly conductively doped foams, lossy magnetic materials coupled to ground planes, lossy dielectric materials, high magnetic permeability materials, mu-metals, ferrite materials, combinations of such materials, stacked hybrids of such materials, etc. In some embodiments, magnetic materials included in the implantable device to absorb RF radiation and further configured to secure an external device (e.g. a positioning device comprising a magnetic as described herein).

Beyond their role in managing emissions, formed or cast or bonded layer of materials such as those described herein may also be used to ensure conformance of an antenna to the patient's anatomy by forcing a flexible antenna to follow the hollow of a patient's back or the curvature of a patient's wrist or ankle.

Single External Antenna

In some embodiments, insensitivity to lateral, rotational, or depth displacement is accomplished by using an antenna system comprising a single external antenna 1136 and one or more implant antennas 1110 wherein the external antenna 1136 is larger than the one or more implant antennas 1110 associated with the implantable device 110. In these embodiments, the implanted antenna 1110 maintains suitable performance when covered by the larger external antenna 1136. An example of such an arrangement is an external antenna 1136 having a large circular or square loop that transmits to an implanted antenna 1110 having a smaller receiving loop that functions as long it is underneath and enclosed by the larger loop of the external antenna 1136. These antennas 1136, 1110 perform best when the size of the loops and distance between them is less than ⅕ of the wavelength of the frequency of operation, and other factors such as tissue absorption and antenna construction may also be considered in selecting the operating frequency. In the more general case, the best operating point is derived by the Z-parameter matrix describing the system. The maximum efficiency depends not only on the cross terms that represent coupling, but also to the impedances of the transmitter and receiver. These impedances vary with frequency, and the coupling terms vary with the relative position, transmission medium, and characteristics of the antenna structures themselves. Therefore, a multi-variable optimization is used to determine the preferred design parameters for a specific system.

The efficiency of such communication between the antennas 1136, 1110 is dictated by Z-parameter matrix, which captures the antenna impedances and their quality factors (Q) as well as coupling relationships. Near-field inductive power transfer functions like a transformer, and medical devices that use this implementation typically use a coupling coefficient (k) that is essentially the cross coupling term in the Z-parameter matrix. With this coupling coefficient k, an optimal coupling point it determined, usually referred to as critical coupling in the literature, that results from reflecting the load on the receiver to the primary transmitter. In doing this, the power transfer efficiency can be represented and analyzed by the voltage transfer, which results in designs that use multiple turns, ferrite cores, and other optimizations around a specific coupling point (which is most strongly influenced by separation distance)—and results in reduced performance as coupling is altered (such as lateral, rotational, or depth displacement). More turns also tend to increase the quality factor (Q), which results in reduced bandwidth in the link between the transmitter and receiver. These additional loops improve efficiency when power can be related to voltage transfer to a fixed load. Essentially, these systems function as a transformer, meaning that the additional loops do not fundamentally improve efficiency, instead they improve efficiency for a fixed loading condition by altering the voltage transformation and the coil impedance. In contrast to this approach, the antenna system considers all the variables in the Z-parameter matrix and the variation of the matrix (that can be due to lateral, rotational, or depth displacement, as well as changes in the transmission medium itself) and optimizes over the range. As part of maximizing power transfer efficiency, the antenna impedances, input and output impedances both affect power transfer efficiency and vary with frequency at a given relative position. With a near-field design, it would be expected that decreasing the frequency would always offer advantages to power transfer efficiency as long as the appropriate number of coils can be used to achieve the ideal voltage transfer. However, an approach that considers the effect of these impedances in addition to the coupling relationships shows that higher efficiencies can be achieved at a specific frequency for a single turn antenna. Additionally, it is apparent that the antenna structures are not behaving as a transformer—the power transfer efficiency is higher than would be expected by pure analyzing the magnetic flux captured by the receiver, suggesting the behavior is more antenna-like with resonant effects. Achieving the desired efficiencies for a given application introduces considerations in the implementations of both the transmitter and receiver, such as methods for adjusting transferred power or receiving low-voltage RF signals. These are further described in, for example, PCT/US2015/020808 and PCT/US2016/016888, both incorporated herein by reference.

Furthermore, the antenna system can be de-sensitized to coupling, which includes lateral, rotational, or depth displacement by using an appropriate impedance transformation of a transmitter and receiver along with an appropriate power harvesting circuit. A single loop external antenna 1136 allows for maximum available bandwidth, and can optimize efficiency over the widest range of operating conditions with adjustable resonant tuning or resonant tuning at a desired operating point. The receiver antenna 1110 utilizes a power harvesting mechanism that has the ability to efficiently recover low voltage signals and also has variable loading as described in, for example, PCT/US2015/020808 and PCT/US2016/016888, both incorporated herein by reference. As coupling increases, the impedances of the transmitting antenna 1136 and receiving antenna 1110 affect each other more strongly, and affect the antenna matching or tuning. For an antenna system with a fixed network for antenna tuning, the network can be selected to achieve the best performance for the anticipated operating range. For example, if the implantation depth is anticipated to range from 0.5 cm to 1.0 cm, a simple conjugate match to the antenna impedances will result in degraded performance as depth decreases and coupling increases (however it would be optimal for operating ranges with low coupling). Alternatively, tuning the coupled impedances at a depth of 0.5 cm may result in degraded performance as depth increases to 1.5 cm, limiting the range. However, tuning at a depth of 1.0 cm can outperform the conjugate match and improve the overall operating range of the antenna system. Depending on the antenna size and construction as well as the intended application, this operating point can be different, and so analysis of the efficiency over the operating range (including all the parameters affecting the link, such as tissue type, depth, alignment, rotation, etc.) with different tuning points is desired. The tuning should be co-designed with the antenna structure as well, particularly because the operating point will likely be affected by tissue absorption and the wavelength relative to the antenna size and separation distance. Alternatively or additionally, the tuning can be adjustable at one or both of the transmitter and the receiver. Usually, the larger antenna will be more sensitive the tuning, and therefore implementing adjustable tuning at the transmitter will have the largest benefit.

The bandwidth of the antenna link will influence the ability to transfer data, and depends on the operating frequency and the quality factor of the transmitter and receiver. In some embodiments, data is transmitted (e.g. data is transferred between the external device and the implantable device) some fraction of the time that the power is being transferred. In these embodiments, the quality factors can be adjusted (e.g. decreased) during data transmission to achieve higher data rates. This adjustment will degrade power transfer efficiency, though will have a small impact because of the relative infrequency of data transmission. When data transfer is not being performed, the quality factor can be re-adjusted (e.g. increased) to increase power transfer efficiency (e.g. restore maximum power transfer efficiency).

In some embodiments, the single transmitting loop of the external antenna 1136 has a long dimension (e.g. a major axis) in the range of 2.0 cm-10.0 cm, such as in the range of 4.0 cm-7.0 cm. In some embodiments, the receiving antenna 1110 has a long dimension (e.g. a major axis) less than 2.0 cm, such as less than 1.2 cm. In some embodiments, the receiving antenna 1110 is elongated so that its long dimension and short dimensions are asymmetric in order to ease implantation. In some embodiments, the transmitting antenna 1136 is elongated in one dimension to reduce sensitivity or improve efficiency in a desirable way. In some embodiments, the operating frequency is in the range of 1 MHz-1 GHz, such as in the range of 30 MHz-300 MHz, such as in the range of 35 MHz-50 MHz. In some embodiments, the carrier frequency is in the range of 40.66 MHz-40.7 MHz, or approximately 40.68 MHz.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:
1. A stimulation system for a patient comprising:
 at least one implantable device comprising at least one implantable antenna;
 an external device comprising at least one external antenna, wherein the at least one external antenna transfers power to the at least one implantable antenna; and
 a positioning device configured to desirably position the at least one external antenna in relation to the patient;
 wherein the positioning device comprises a clip with an adhesive portion, wherein the clip comprises a housing comprising:
(a) a first portion;
(b) a second portion opposite the first portion; and
(c) a cavity defined by the first portion and the second portion, the cavity shaped to receive at least a portion of the external device, wherein the adhesive portion is coupled to the second portion of the housing and adapted to adhere the clip to the patient's skin, and wherein the at least one implantable device delivers therapy to the patient, wherein the external device comprises a first external device, wherein the system further comprises at least a second external device comprising at least one external antenna, and wherein the multiple external devices are configured to automatically make a patient-position based therapy adjustment and/or a situation-based therapy adjustment.

2. The stimulation system according to claim 1, wherein the cavity is constructed and arranged to slidingly receive the at least the portion of the external device.

3. The stimulation system according to claim 1, wherein the external device comprises at least one control, and wherein the first portion of the housing of the clip including an opening, and wherein the housing is adapted to orient the external device to align the at least one control with the opening when the at least the portion of the external device is received by the housing, thereby providing access to the at least one control.

4. The stimulation system according to claim 1, wherein the cavity of the clip is at least partially shaped to complement an outer contour of the external device, allow the external device and the housing to removably couple to one another.

5. The stimulation system according to claim 1, further comprising a sensor configured to produce a signal related to patient location and/or position, wherein the system is configured to make a therapy adjustment based on the signal.

6. The stimulation system according to claim 5, wherein the sensor comprises a sensor selected from the group consisting of: accelerometer; GPS sensor; a wirelessly connectable low energy sensor; and a combination thereof.

7. The stimulation system according to claim 1, wherein the at least one external antenna comprises multiple antennas, and wherein the external device comprises a transmitter operatively connected to the multiple antennas.

8. The stimulation system according to claim 1, wherein the at least one external antenna and/or the at least one implantable antenna comprises an array of antennas configured to reduce sensitivity to alignment and/or rotation between the at least one external antenna and the at least one implantable antenna.

9. The stimulation system according to claim 1, further comprising a feedback element configured to notify the patient that repositioning of the at least one external antenna is desired.

10. The stimulation system according to claim 9, wherein the feedback element comprises an element selected from the group consisting of: a visual feedback element; an LED; an acoustic feedback element; a buzzer; a tactile feedback element; a haptic transducer; modified stimulation; paresthesia-causing stimulation; and combinations thereof.

11. The stimulation system according to claim 1, wherein the at least one implantable device comprises a locating element.

12. The stimulation system according to claim 11, wherein the locating element comprises an element selected from the group consisting of: a ring-shaped element; a cavity; a dome; and combinations thereof.

13. The stimulation system according to claim 1, further comprising an external sensor and/or mechanism configured to determine the implantable device implant location.

14. The stimulation system according to claim 13, wherein the external sensor and/or mechanism comprises an electrical, magnetic, and/or mechanical sensor.

15. The stimulation system according to claim 13, wherein the external sensor and/or mechanism is configured to determine the implantable device implant location using power transfer parameters and/or coupling coefficients.

16. The stimulation system according to claim 13, wherein the external sensor and/or mechanism is configured to determine the implantable device implant location using received power, RF signal strength, and/or supply voltage measurements made by the implanted system and communicated to the external device, through a data back channel.

17. The stimulation system according to claim 13, wherein the external sensor and/or mechanism is configured to determine the implantable device implant location using parameters sensed by the external device by detecting changes in loading that indicate received power of the internal system, mutual inductances, and/or backscattered electromagnetic fields.

18. The stimulation system according to claim 1, wherein the external device comprises at least two batteries, and wherein the external device is configured to operate using energy from a single battery.

19. The stimulation system according to claim 1, wherein the at least one external antenna comprises a single loop antenna with a first size, wherein the at least one implantable antenna comprises a single loop antenna with a second size, and wherein the first size is greater than the second size.

20. The stimulation system according to claim 1, wherein the at least one external antenna comprises a major axis with a length between 2 cm and 10 cm, and wherein the at least one implantable antenna comprises a major axis with a length less than 2 cm.

21. The stimulation system according to claim 20, wherein the at least one external antenna comprises a major axis with a length between 4 cm and 7 cm, and wherein the at least one implantable antenna comprises a major axis with a length less than 1.2 cm.

22. The stimulation system according to claim 1, wherein the at least one external antenna comprises multiple external antennas that communicate with the at least one implantable antenna, and wherein the multiple external antennas are constructed and arranged based on the at least one implantable antenna.

23. The stimulation system according to claim 1, wherein the at least one external antenna further transfers data to the at least one implantable antenna, and wherein the power and data are transferred in combination and/or asynchronously.

24. The stimulation system according to claim 1, wherein the positioning device is configured to allow further adjustment of the position of the at least one external antenna once the at least one external antenna is desirably positioned by the positioning device.

\* \* \* \* \*